US005714596A

United States Patent [19]

Houghton et al.

[11] Patent Number: 5,714,596
[45] Date of Patent: Feb. 3, 1998

[54] NANBV DIAGNOSTICS: POLYNUCLEOTIDES USEFUL FOR SCREENING FOR HEPATITIS C VIRUS

[75] Inventors: Michael Houghton, Danville; Qui-Lim Choo, El Cerrito; George Kuo, San Francisco; Amy J. Weiner, Oakland; Jang Han, Lafayette; Michael Steven Urdea, Alamo; Bruce Duncan Irvine, Concord; Janice A. Kolberg, Richmond, all of Calif.

[73] Assignee: Chiron Corporation, Emeryville, Calif.

[21] Appl. No.: 40,564

[22] Filed: Mar. 31, 1993

Related U.S. Application Data

[63] Continuation of Ser. No. 566,209, Aug. 8, 1990, abandoned, which is a continuation-in-part of Ser. No. 505,435, Apr. 4, 1990, abandoned, which is a continuation-in-part of Ser. No. 456,637, Dec. 21, 1989, abandoned, and a continuation-in-part of Ser. No. 355,002, May 18, 1989, abandoned, and a continuation-in-part of Ser. No. 355,961, May 18, 1989, abandoned, which is a continuation-in-part of Ser. No. 341,334, Apr. 20, 1989, abandoned, which is a continuation-in-part of Ser. No. 353,896, Apr. 21, 1989, abandoned, and a continuation-in-part of Ser. No. 325,338, Mar. 17, 1989, abandoned, which is a continuation-in-part of Ser. No. 271,450, Nov. 14, 1988, abandoned, which is a continuation-in-part of Ser. No. 263,584, Oct. 26, 1988, abandoned, which is a continuation-in-part of Ser. No. 191,263, May 6, 1988, abandoned, which is a continuation-in-part of Ser. No. 161,072, Feb. 26, 1988, abandoned, which is a continuation-in-part of Ser. No. 139,886, Dec. 30, 1987, abandoned, which is a continuation-in-part of Ser. No. 122,714, Nov. 18, 1987, abandoned.

[51] Int. Cl.⁶ .................. C07H 21/04; C12Q 1/70; C12Q 1/68; C12N 15/00

[52] U.S. Cl. .................. 536/23.72; 536/23.1; 536/24.3; 536/25.3; 536/25.32; 435/5; 435/6; 435/91.1; 435/91.33; 436/94; 935/1; 935/3; 935/5; 935/8; 935/19; 935/76; 935/77; 935/78

[58] Field of Search .................. 435/6, 5, 91.1, 435/23.1, 91.3, 91.33, 91.32, 320.1; 536/23.72, 24.3, 25.3, 25.32; 935/1, 5, 3, 8, 19, 76, 77, 78, 111

[56] References Cited

U.S. PATENT DOCUMENTS

| | | | |
|---|---|---|---|
| 4,659,678 | 4/1987 | Forrest et al. | 435/512 |
| 4,673,634 | 6/1987 | Seto et al. | 424/228.1 |
| 4,683,195 | 7/1987 | Mullis et al. | 435/6 |
| 4,683,202 | 7/1987 | Mullis et al. | 435/91.2 |
| 4,702,909 | 10/1987 | Villarejos et al. | 424/228.1 |
| 4,891,313 | 1/1990 | Berger et al. | 435/7.94 |
| 5,077,193 | 12/1991 | Mishiro et al. | 435/5 |
| 5,106,726 | 4/1992 | Wang | 435/5 |
| 5,191,064 | 3/1993 | Arima et al. | 530/324 |
| 5,218,099 | 6/1993 | Reyes et al. | 536/23.72 |
| 5,436,126 | 7/1995 | Wang | 435/5 |

FOREIGN PATENT DOCUMENTS

| | | |
|---|---|---|
| 36979/89 | 11/1989 | Australia . |
| 89/10967 | 11/1989 | Australia . |
| 58123/90 | 12/1990 | Australia . |
| 0061974 | of 1982 | European Pat. Off. . |
| 0194207 | of 1986 | European Pat. Off. . |
| 0279460 | of 1988 | European Pat. Off. . |
| 0263761 | 4/1988 | European Pat. Off. . |
| 0277437 | 8/1988 | European Pat. Off. . |
| 88400790.7 | 11/1988 | European Pat. Off. . |
| 0318216 | 5/1989 | European Pat. Off. . |
| 0388232 | 9/1990 | European Pat. Off. . |
| 0442394 A2 | 8/1991 | European Pat. Off. . |
| 0293274 | 9/1991 | European Pat. Off. . |
| 0468527 A2 | 1/1992 | European Pat. Off. . |
| 58-183629 | 10/1983 | Japan . |
| 2-500880 | 3/1990 | Japan . |
| 5-81600 | 11/1993 | Japan . |
| 77108060 | 7/1992 | Taiwan . |
| 2239245 | 6/1991 | United Kingdom . |
| 2212511 | 1/1992 | United Kingdom . |
| WO 82/00205 | of 1982 | WIPO . |
| WO 82/02774 | of 1982 | WIPO . |
| WO 82/03330 | of 1982 | WIPO . |
| WO 87/05930 | of 1987 | WIPO . |
| WO 88/03410 | 5/1988 | WIPO . |
| WO 89/04669 | 6/1989 | WIPO . |
| WO 89/05855-A | 6/1989 | WIPO . |
| WO 89/10967 | 11/1989 | WIPO . |
| WO 90/11089 | 10/1990 | WIPO . |
| WO 90/14436 | 11/1990 | WIPO . |
| WO 91/15516 | of 1991 | WIPO . |
| WO 93/00365 | 1/1993 | WIPO . |

OTHER PUBLICATIONS

Sommer and Tautz, Nucleic Acids Research, vol. 17, No. 16 (1989), p. 6749.

Schmale et al. *EMBO J.* vol. 3, pp. 3289–3293 (1984) Computer generated printout only.

Mezquita et al. *J. Mol. Evol.* vol. 21, pp. 209–219 (1985) computer generated printout only.

Sequence search RN 157179–22–1 (corresponds to pp. 4456–4465 of Cl. 11).

Sequence search, RN 157080–48–3 (corresponds to pp. 4381–4390 of Cl. 9).

Sequence search, RN 157178–85–3 (corresponds to pp. 318–308 of cl. 7).

Sequence Search, RN 156931–07–6 (corresponds to pp. 8041–8058 of cl. 6).

Sequence Search, RN 156888–41–4 (corresponds to pp. 4042–4051 of cl. 10).

(List continued on next page.)

*Primary Examiner*—Bradley L. Sisson
*Attorney, Agent, or Firm*—Kenneth M. Goldman; Robert P. Blackburn

[57] ABSTRACT

A new virus, Hepatitis C virus (HCV), which has proven to be the major etiologic agent of blood-borne NANBH, was discovered by Applicant. Reagents for isolating, amplifying, and detecting HCV polynucleotides are provided. These reagents are oligomers comprised of polynucleotide sequences which are capable of forming hybrid structures with HCV target polynucleotide sequences.

27 Claims, 35 Drawing Sheets

OTHER PUBLICATIONS

Arrand et al., "Molecular Cloning of the Complete Epstein–Barr Virus Genome as a Set of Overlapping Restriction Endonuclease Fragments," *Nucleic Acids Res.* 9(13):2999–3014 (1981).

Baer, et al., "DNA Sequence and Expression of the B95–8 Epstein–Barr Virus Genome," *Nature* 310:207–211 (1984).

Bankier, et al., "Sequence Analysis of the 17,166 Base–Pair Ecori Fragment C of B95–8 Epstein–Barr Virus," *Mol. Biol. Med.* 1:21–45 (1983).

Beck, et al., "Human Cytomegalovirus Encodes a Glycoprotein Homologous to MHC Class–I Antigens," *Nature* 331:269–272 (1988).

Mierendorf, et al., "Gene Isolation of Screening γgt11 Libraries With Antibodies," *Methods in Enzymology*, Ch. 51, Berger & Kimmel (Eds), Academic Press Ltd. (1987).

Biggin, et al., "Transcription and DNA Sequence of the Bamhi L Fragment of B95–8 Epstein–Barr Virus," *EMBO J.* 3(5):1083–1090 (1984).

Billeter, et al., "Cloning of DNA Corresponding to Four Different Measles Virus Genomic Regions," *Virology* 132:147–159 (1984).

Blumberg, "Australia Antigen and Biology of Hepatitis B," *Science* 197:17–25 (1977).

Bodescot, et al., "Clustered Alternative Splice Sites In Epstein–Barr Virus Rnas," *Nucleic Acids Res.* 15:5887 (1987).

Boss, et al., "Cloning and Sequence Analysis of the Human Major Histocompatibility Complex Gene DC–3∂," *Proc. Natl. Acad. Sci. USA* 81:5199–5203 (1984).

Bradley, "Research Perspectives in Posttransfusion Non–A, Non–B Hepatitis," *Infection, Immunity and Blood Transfusion*, (Dodd, R.Y. & Barker, L.F. (Eds.), Alan R. Liss Inc.) pp. 81–97 (1985).

Bradley, et al., "Transmission, Etiology and Pathogenesis of Viral Hepatitis Non–A, Non–B in Non–Human Primates," *Adv. Hepat. Res.* Ch.31 pp. 268–280 (1984).

Bradley, et al., "Posttransfusion Non–A, Non–B Hepatitis: Physicochemical Properties of Two Distinct Agents," *J. Infect. Dis.* 148(2):254–265 (1983).

Burrell, et al., "Expression in Escherichia Coli of Hepatitis B Virus DNA Sequences Cloned in Plasmid Pbr322," *Nature* 279:43–47 (1979).

Chan, et al., "Serological Responses to Infection with Three Different Types of Hepatitis C Virus," *The Lancet* 338:1391 (1991).

Charnay, et al., "Biosynthesis of Hepatitis B Virus Surface Antigen in Escherichia coli," *Nature* 286:893–895 (1980).

Daniels, et al., "A Second Major Class of Alu Family Repeated DNA Sequences in a Primate Genome," *Nucleic Acids Res.* 11(21):7595–7610 (1983).

Davies (ed.), *Amino Acids and Peptides*, (Chapman and Hall, London, 1985).

Davis, et al., "Isolation of cDNA Clones for Differentially Expressed Genes of the Human Parasite Schistosoma Mansoni," *Proc. Natl. Acad. Sci. USA* 83:5534–5538 (1986).

Davison, et al., "The Complete DNA Sequence of Varicella–Zoster Virus," *J. Gen. Virol.* 67:1759–1816 (1986).

Deininger, et al., "Sequence Analysis and in Vitro Transciption of Portions of the Epstein–Barr Virus Genome," *J. Cell Biochem.* 19:267–274 (1982).

Dull, et al., "Insulin–Like Growth Factor II Precursor Gene Organization in Relation to Insulin Gene Family," *Nature* 310:777–781 (1984).

Emtage, et al., "Influenza Antigenic Determinants Are Expressed From Haemagglutinin Genes Cloned in Escherichia coli," *Nature* 283:171–174 (1980).

Farci, et al., "A Long–Term Study of Hepatitis C Virus Replication In Non–A, Non–B Hepatitis," *New Eng. J. Med.* 325(2):96–104 (1991).

Farrell, et al., "Latent and Lytic Cycle Promoters of Epstein––Barr Virus," *EMBO J.* 2(8):1331–1338 (1983).

Farrell, et al., "Homologous Upstream Sequences Near Epstein–Barr Virus Promoters," *Proc. Natl. Acad. Sci. USA* 80:1565–1569 (1983).

Feinstone, et al., "Transfusion–Associated Hepatitis Not Due To Viral Hepatitis Type A Or B," *New England J. Med.* 292(15):767–770 (1975).

Forsgren, et al., "Molecular Cloning and Characterization of A Full–Length cDNA Clone for Human Plasminogen," *FEBS Lett.* 213(2):254–260 (1987).

Geysen, et al., "A Priori Delineation of A Peptide Which Mimics A Discontinuous Antigenic Determinant," *Mol. Immunol.* 23:709–715 (1986).

Gibson, et al., "Homology Between Two EBV Early Genes and HSV Ribonucleotide Reductase and 38K Genes," *Nucleic Acids Res.* 12(12):5087–5099 (1984).

Gilmore, et al., "The Nucleocapsid Gene of Infectious Hematopoietic Necrosis Virus, A Fish Rhabdovirus," *Virology* 167:644–648 (1988).

Glover (ed), *DNA Cloning 1: A Practical Approach*, (IRL Press, Washington DC, USA) (1985).

Gross, et al., (eds), *The Peptides*, (Academic Press, New York, 1983).

Habets, et al., *HCV Antibodies React with Ross River Virus Peptide*, (Aug. 25, 1994).

U.K. High Court Judgment in Chiron vs. Organon, Akzo Pharma, and UBI and Chiron vs. Murex (Nov. 2, 1995).

U.K. Appeals Court Judgment in Chiron vs. Organon, Akzo Pharma, and UBI and Chiron vs. Murex (Oct. 5, 1993).

Houghton, et al., "Molecular Biology of the Hepatitis C Viruses: Implications for Diagnosis, Development and Control of Viral Disease," *Hepatology* 14:381–388 (1991).

Ishida, et al., "Sequence of 2,617 Nucleotides From the 3' End of Newcastle Disease Virus Genome RNA and the Predicted Amino Acid Sequence of Viral NP Protein," *Nucleic Acids Res.* 14(16):6551–6564 (1986).

Jeang, et al., "Organization of the Epstein–Barr Virus DNA Molecule. III. Location of the P3hr–1 Deletion Junction and Characterization of the Noti Repeat Units That Form Part of the Template for An Abundant 12–O–Tetradecanoylphorbol–13–Acetate–Induced mRNA Transcript," *J. Virol.* 48(1):135–148 (1983).

Jones, et al., "The EB Virus Genome In Daudi Burkitt's Lymphoma Cells Has A Deletion Similar To That Observed In A Non–Transforming Strain (P3HR–1) of the Virus," *EMBO J.* 3(4):813–821 (1984).

Kemp, et al., "Direct Immunoassay for Detecting *Escherichia Coli* Colonies That Contain Polypeptides Encoded By Cloned DNA Segments," *Proc. Natl. Acad. Sci. USA* 78(7):4520–4524 (1981).

Kilejian, et al., "Histidine–Rich Domain of the Knob Protein of the Human Malaria Parasite *Plasmodium Falciparum*," *Proc. Natl. Acad. Sci. USA* 83:7938–7941 (1986).

Kozak, "Possible Role of Flanking Nucleotides In Recognition of the AUG Initiator Codon By Eukaryotic Ribosomes," *Nucleic Acids Res.* 9(20):5233–5252 (1981).

Krissansen, et al., "Primary Structure of T3 K Subunit of the T3/T Cell Antigen Receptor Complex Deduced From Cdna Sequences: Evolution of the T3 K and Λ Subunits," EMBO J. 5(8):1799–1808 (1986).

Ladin, et al., "Characterization of A cDNA Encoding Ricin E, A Hybrid Ricin–*Ricinus Communis* Agglutinin Gene From the Castor Plant *Ricinus Communis,*" *Plant Mol. Biol.* 9:287–295 (1987).

Laux, et al., "A Spliced Epstein–Barr Virus Gene Expressed In Immortalized Lymphocytes Is Created By Circularization of the Linear Viral Genome," *EMBO J.* 7(3):769–774 (1988).

Leguoy, et al., "Structure and Expression of the Murine L–Myc Gene," *EMBO J.* 6(11):3359–3366 (1987).

Malby, et al., "The Structure of A Complex Between the NC10 Antibody and Influenza Virus Neuraminidase and Comparison With the Overlapping Binding Site of the NC41 Antibody," *Structure* 2:733–746 (1994).

Maniatis, et al., *Molecular Cloning: A Laboratory Manual,* Cold Spring Harbour Press, Cold Spring Harbour, NY (1982).

Mason, et al., "Partial Nucleotide Sequence of the Japanese Encephalitus Virus Genome," *Virology* 158:348–360 (1987).

May, et al., "Significance of Similarities In Patterns: An Application To ζ Interferon–Related DNA On Human Chromosome 2," *Proc. Natl. Acad. Sci. USA* 82:4090–4094 (1985).

McOmish, et al., "Detection of Three Types of Hepatitis C Virus In Blood Donors: Investigation of Type–Specific Differences In Serologic Reactivity and Rate of Alanine Aminotransferase Abnormalities", *Transfusion* 33(1):7–13 (1993).

McOmish, et al., "Geographical Distribution of Hepatitis C Virus Genotypes In Blood Donors: An International Collaborative Survey," *J. Clin. Microbiol.* 32(4):884–892 (1994).

Kemp, et al., *Methods of Enzymology,* 79:622–630 (1981), published by Academic Press Inc.

Molenaar, et al., "Structure and Organization of Two Linked Ribosomal Protein Genes In Yeast," *Nucl. Acids Res.* 12(19):7345–7358 (1984).

Murray, et al., "The Expression of Hepatitis B Virus Antigen Genes In Escherichia Coli," *Hepatitis B. Vaccine, INSERM Symposium No. 18* (Maupas, et al. eds.), pp. 289–304 (1981).

Ogasawara, et al., "Genes and their Organization In the Replication Origin Region of the Bacterial Chromosome," *Mol. Microbiol.* 6(5):629–634 (1992).

Oram, et al., "Use of Recombinant Plasmids To Investigate the Structure of the Human Cytomegalovirus Genome," *J. Gen. Virol.* 59:111–129 (1982).

Pasek, et al., "Hepatitis B Virus Genes & their Expression In *E. Coli,*" *Nature* 282:575–579 (1979).

Prince, et al., *Viral Hepatitis* pp. 633–640 (The Franklin Press, 1978).

Prince, et al., "Long–Incubation Post–Transfusion Hepatitis Without Serological Evidence of Exposure To Hepatitis–B Virus," *The Lancet* pp. 241–246 (Aug. 3, 1974).

Prince, et al., "Inactivation of Hepatitis B and Hutchinson Strain Non–A, Non–B Hepatitis Viruses By Exposure To Tween 80 and Ether," *Vox Sang* 46:36–43 (1984).

Reyes, et al., "Molecular Biology of Non–A, Non–B Hepatitis Agents: Hepatitis C and Hepatitis E Viruses," *Advances in Virus Research* 40:57–102 (1991).

Rice, et al., *Proc. Natl. Acad. Sci. USA* 78:2062–2066 (1981).

Sagar, et al., "Interferon–∂–Related DNA Is Dispersed In the Human Genome," *Science* 223:1312–1315 (1984).

Seguin, et al., "DNA Sequence and Transcription of Bamhi Fragment B Region of B95–8 Epstein–Barr Virus," *Mol. Biol. Med.* 1:369–392 (1983).

Sehgal, et al., "Isolation of Novel Human Genomic DNA Clones Related To Human Interferon–∂₁ Cdna," *Proc. Natl. Acad. Sci. USA* 80:3632–3636 (1983).

Shine, et al., "The 3'–Terminal Sequence of *Escherichia Coli* 16S Ribosomal RNA: Complementarity To Nonsense Triplets and Ribosome Binding Sites," *Proc. Natl. Acad. Sci. USA* 71(4):1342–1346 (1974).

Simmonds, et al., "Mapping of Serotype–Specific, Immunodominant Epitopes In the NS–4 Region of Hepatitis C Virus (HCV): Use of Type–Specific Peptides To Serologically Differentiate Infections With HCV Types 1, 2 and 3," *J. Clin. Microbiol.* 31(6):1493–1503 (1993).

Sprengel, et al., "Comparative Sequence Analysis of Defective and Infectious Avian Hepadnaviruses," *Nucleic Acids. Res.* 19(15):4289 (1991).

Staden, "Measurements of the Effects That Coding for A Protein Has On A DNA Sequence and their Use for Finding Genes," *Nucleic Acids Res.* 12(1):551–567 (1984).

Strauss, et al., "Complete Nucleotide Sequence of the Genomic RNA of Sindbis Virus," *Virology* 133:92–110 (1984).

Strauss, et al., "Sequence Coding for the Alphavirus Nonstructural Proteins Is Interrupted By An Opal Termination Codon," *Proc. Natl. Acad. Sci. USA* 80:5271–5275 (1983).

Sudhof, et al., "cDNA and Derived Amino Acid Sequences for Rat and Human Synaptophysin," *Nucleic Acids Res.* 15(22):9607 (1987).

Sugitani, et al., "Sensitivity of Serological Assays To Identify Blood Donors With Hepatitis C Viraemia," *The Lancet* 339:1018–1019 (1992).

Takagi, et al., "Nucleotide Sequence and Promoter Region for the Neutral Protease Gene From *Bacillus Stearothermophilus,*" *J. Bacteriol.* 163(3):824–831 (1985).

Takahashi, et al., "Complete Nucleotide Sequence of the Human Corticotropin–∂–Lipotropin Precursor Gene," *Nucleic Acids Res.* 11(19):6847–6858 (1983).

Takkinen, "Complete Nucleotide Sequence of the Nonstructural Protein Genes of Semliki forest Virus," *Nucl. Acids Res.* 14(14):5667–5682 (1986).

Tamashiro, et al., "Structure of the Heterogeneous L–S Junction Region of Human Cytomegalovirus Strain AD169 DNA," *J. Virol.* 52(2):541–548 (1984).

"Mysterious Strain of Hepatitis Is Identified," *The Wall Street Journal,* Friday, 21 Apr. 1989.

Vallari, et al., "Serological Markers of Posttransfusional Hepatitis C Viral Infection," *J. Clin. Microbiol.* 30(3):552–556 (1992).

Weston, et al., "Sequence of the Short Unique Region, Short Repeats, and Part of the Long Repeats of Human Cytomegalovirus,"*J. Mol. Biol.* 192:177–208 (1986).

Yang, et al., "Human Dihydrofolate Reductase Gene Organization. Extensive Conservation of the G+C–Rich 5' Non–Coding Sequence and Strong Intron Size Divergence From Homologous Mammalian Genes," *J. Mol. Biol.* 176:169–187 (1984).

Yates, et al., "A *Cis*-Acting Element From the Epstein–Barr Viral Genome That Permits Stable Replication of Recombinant Plasmids In Latently Infected Cells," *Proc. Natl. Acad. Sci. USA* 81:3806–3810 (1984).

Young, et al., "Efficient Isolation of Genes By Using Antibody Probes," *Proc. Natl. Sci. USA* 80:1194–1198 (1983).

Suzuki, et al., "Characterization of a cDNA for Human Protein C Inhibitor," *J. Biol. Chem.* 262(2):611–616 (1987).

First Opposition to Chiron Japanese Patent Application No. 01–500565, filed by Steven Woodsmall (and translation) with supporting documents.

Reply to First Opposition to Chiron Japanese Patent Application No. 01–500565.

Second Opposition to Chiron Japanese Patent Application No. 01–500565, filed by Akira Yamamoto (and translation) with supporting documents.

Reply to Second Opposition to Chiron Japanese Patent Application No. 01–500565.

Third Opposition to Chiron Japanese Patent Application No. 01–500565, filed by Asako Sudo (and translation) with supporting documents.

Reply to Third Opposition to Chiron Japanese Patent Application No. 01–500565.

Fourth Opposition to Chiron Japanese Patent Application No. 01–500565, filed by Yashimi Tawara (and translation) with supporting documents.

Reply to Fourth Opposition to Chiron Japanese Patent Application No. 01–500565.

Fifth Opposition to Chiron Japanese Patent Application No. 01–500565, filed by Tetsuo Nakamura (and translation).

Reply to Fifth Opposition to Chiron Japanese Patent Application No. 01–500565.

Sixth Opposition to Chiron Japanese Patent Application No. 01–500565, filed by Toren K.K. (and translation) with supporting documents.

Reply to Sixth Opposition to Chiron Japanese Patent Application No. 01–500565.

Seventh Opposition to Chiron Japanese Patent Application No. 01–500565, filed by Sumitomo Metal Industries, Ltd. (and translation) with supporting documents.

Reply to Seventh Opposition to Chiron Japanese Patent Application No. 01–500565.

Eighth Opposition to Chiron Japanese Patent Application No. 01–500565, filed by Hiroshi Iino (and translation) with supporting documents.

Reply to Eighth Opposition to Chiron Japanese Patent Application No. 01–500565.

Ninth Opposition to Chiron Japanese Patent Application No. 01–500565, filed by Kyokuto Seiyaki Kogyo, Inc. (and translation) with supporting documents.

Reply to Ninth Opposition to Chiron Japanese Patent Application No. 01–500565.

Tenth Opposition to Chiron Japanese Patent Application No. 01–500565, filed by United Biomedical, Inc. (and translation) with supporting documents.

Replay to Tenth Opposition to Chiron Japanese Patent Application No. 01–500565.

Eleventh Opposition to Chiron Japanese Patent Application No. 01–500565, filed by Kokusai Shiyaku (and translation) with supporting documents.

Reply to Eleventh Opposition to Chiron Japanese Patent Application No. 01–500565.

Twelfth Opposition to Chiron Japanese Patent Application No. 01–500565, filed by Shigeo Kimura (and translation) with supporting documents.

Reply to Twelfth Opposition to Chiron Japanese Patent Application No. 01–500565.

Thirteenth Opposition to Chiron Japanese Patent Application No. 01–500565, filed by Akzo Neamloze Vennootschap (and translation).

Reply to Thirteenth Opposition to Chiron Japanese Patent Application No. 01–500565.

Fourteenth Opposition to Chiron Japanese Patent Application No. 01–500565, filed by F. Hoffman la Roche AG (and translation) with supporting documents.

Reply to Fourteenth Opposition to Chiron Japanese Patent Application No. 01–500565.

Translation of Decision on Opposition Against Patent Application No. 01–500565, issued Dec. 22, 1995.

Statement of Grounds for Opposition to Australian Patent No. 640,920, filed by Hoffman La Roche with supporting documents.

Australian Litigation Bundle, for Chiron Australian Patent No. 624,105.

Murex Reply in the Litigation of Chiron Australian Patent No. 624,105.

First Opposition to Chiron European Application No. 0 318 216, filed by Akzo Pharma BV (Jan. 27, 1994) with supporting documents.

Second Opposition to Chiron European Application No. 0 318 216, filed by Murex Diagnostics Limited(Sep. 12, 1994) with supporting documents.

Third Opposition to Chiron European Application No. 0 318 216, filed by United Biomedical (Sep. 15, 1994) with supporting documents.

Fourth Opposition to Chiron European Application No. 0 318 216, filed by Beringwerke (Sep. 15, 1994).

Fifth Opposition to Chiron European Application No. 0 318 216, filed by The Research Foundation for Microbial Diseases (Sep. 14, 1994) with supporting documents.

Sixth Opposition to Chiron European Application No. 0 318 216, filed by F. Hoffman–La Roche AG(Sep. 15, 1994).

J.A. Kemp & Co.(Chiron): Response By Patentee To Notices of Opposition re EP 318 216, Jun. 1995.

Miscellaneous Documentation (believed to have been supplied to Prof. Donald Chisum by Dr. Bradley or the Center for Disease Control).

Daniel W. Bradley, v. Chiron Corporation, Civil Action No. 94–4342 Litigation Bundle, with supporting doucments.

[U.K. Litigation Bundle 1].
[U.K. Litigation Bundle 2].
[U.K. Litigation Bundle 5].
[U.K. Litigation Bundle 6].
[U.K. Litigation Bundle 7].
[U.K. Litigation Bundle 7a].
[U.K. Litigation Bundle 7b].
[U.K. Litigation Bundle 7c].
[U.K. Litigation Bundle 8].
[U.K. Litigation Bundle 9].
[U.K. Litigation Bundle 9.a.1].
[U.K. Litigation Bundle 9.a.2].
[U.K. Interlocutory Affidavits and Exhibits, vol. 1].
[U.K. Interlocutory Affidavits and Exhibits, vol. 2].
[U.K. Interlocutory Affidavits and Exhibits, vol. 3].
[U.K. Interlocutory Affidavits and Exhibits,vol. 4].
[U.K. Transcript Speeches and Evidence, vol. 4].

Bioindustry 3:302 (1986); (previously considered.

*Chiron News Release*, "Chiron Clones Hepatitis Non–A, Non–B Virus Which May Allow Screening for Previously Undetectable Disease," No. 21 (May 10, 1988).

Viral *Hepatitis and Liver Disease* 620 (1984).

Winnacker, "From Genes to Clones Introduction to Gene Technology," (publ., VCH Germany, 1987), pp. 39–41.

Aaskov, et al., "An Immunofluoroscence Assay For Human Antibodies to Ross River Virus," *J. Immu. Meth.* 25:37–41 (1979).

Alter, et al., "Detection of Antibody to Hepatitis C Virus in Prospetively Followed Transfusion Recipients with Acute and Chronic Non–A, Non–B Hepatitis," *N. Engl. J. of Med.* 321:1494–1500 (1989).

Arikan, et al., "Sequences of the E. coli evrB Gene and Protein," *Nucleic Acids Res.* 14(6):2637 (1986).

Arima, et al., "A Lambda gt11–cDNA Clone Specific for chronic Hepatitis C Generated from Pooled Clone Serum Presumably Infected by Hepatitis C Virus," *Gastroenterol. Jpn.* 24(5):545–548 (1989).

Arima, et al., "Cloning of a cDNA Associated with Acute and Chronic Hepatitis C Infection Generated from Patients Serum RNA," *Gastroenterol. Jpn.* 24(5):540–544 (1989).

Backendorf, et al., "Structure of the uvrB Gene of Escherichia coli. Homology with Other DNA Repair Enzymes and Characterization of the uvrB5 mutation," *Nucleic Acids Res.* 14(7):2877–2890 (1986).

Bankier, et al., "DNA Sequence Analysis of the *ECORI* Dhet Fragment of B95–8 Epstein–Barr Virus Containing the Terminal Repeat Sequences," *Mol. Biol. Med.* 1:425–445 (1983).

Mierendorf, et al., "Gene Isolation by Screening Σgt11 Libraries with Antibodies," *Methods of Enzymology,* Chpt. 51, vol. 152 (1987) Berger & Kimmel (eds).

Bradley, "The Agents of Non–A, Non–B Viral Hepatitis," *J. Virol. Meth.* 10:307–319 (1985).

Bradley, et al., "Posttransfusional Non–A, Non–B Hepatitis in chimpanzees. Physiochemical Evidence that the Tubule-forming Agent is a Small Enveloped Virus," *Gastroenterology* 88:773–779 (1985).

Bradley, et al., "Posttransfusion Non–A, Non–B Hepatitis: Physiochemical Properties of Two Distinct Agents," *J. Infect. Dis.* 148(2):254–265 (1983).

Bradley, et al., "Experimental Infection of Chimpanzees with Antihemophilic (Factor VIII) Materials: Recovery of Virus–Like Particles Associated with Non–A, Non–B Hepatitis," *J. Med. Virol.* 3:253–269 (1979).

Bradley, et al., "Enterically Transmitted Non–A, Non–B Hepatitis: Serial Passage of Disease in Cynomolgus Macaques and Tamarins and Recovery of Disease–Associated 27 to 37nm Virus like Particles," *Proc. Natl. Acad. Sci. USA* 84:6277–6281 (1987); (previously).

Bradley, et al., "Hepatitis Non–A, Non–B Viruses Become Identified as Hepatitis C and E Viruses," *Prog. Med. Virol.* 37:101–135 (1990).

Bradley, et al., "Etiology and Natural History of Post–Transfusion and Enterically–Transmitted Non–A, Non–B Hepatitis," *Seminars in Liver Disease* 6(1):56–66 (1986).

Bryan, "Viral Hepatitis. 1. Clinical and Laboratory Aspects and Epidermiology," *Interstate Postgrad. Med. USA* 68(5):66–86.

Burk, et al., "Detection of Non–A, Non–B Hepatitis Antigen by Immunocytochemical Staining," *Proc. Natl. Acad. Sci. USA* 81:3195–3199 (1984).

Burkhardt, et al., "Hepatitis Non–A, Non–B Associated Substance in Feces Identification and Cloning of a Partially Double–Stranded Circular DNA," *Immun. Infect.* 16(3):91–96 (1988).

Burkhardt, et al., "Hepatitis Non–A, Non–B–associated DNA–Demonstration of the DNA in a proven infectious anti–D–immunoglobulin," *Immun. Infect.* 16(3):97–99 (1988).

Butt (Ed.), *Practical Immunoassay: The State of the Art,* Chpt. 3, vol. 14 (1984).

Buttner, et al., "The Agarose Gene (dagA) of Streptomyces coelicor A3(2): Nucleotide Sequence and Transcriptional Analysis," *Mol. Gen. Genet.* 209:101–109 (1987).

Carman, et al., "Vaccine–Induced Escape Mutant of Hepatitis B Virus," *The Lancet* 336:325–329 (1990).

Cashdollar, et al., "Cloning the double–stranded RNA genes of reovirus: Sequence of the cloned S2 gene," *Proc. Natl. Acad. Sci. USA* 79:7644–7648 (1982).

Castle, et al., "Sequence Analysis of the Viral Core Protein and the Membrane–Associated Proteins V1 and NV2 of the Flavivirus West Nile Virus of and the Genome Sequence for these Proteins," *Virology* 145:227–236 (1985).

Cha, et al., "At Least Five Related, But Distinct, Hepatitis C Viral Genotypes Exist," *Proc. Natl. Acad. Sci. USA* 89:7144–7148 (1992).

Choo, et al., "Hepatitis C Virus: The Major Causative Agent of Viral Non–A, Non–B Hepatitis," *Brit. Med. Bulletin* 46(2):423–441 (1990).

Choo, et al., "Isolation of cDNA Clone Derived from a Blood–Borne Non–A, Non–B Viral Hepatitis Genome," *Science,* 244:359–362 (1989).

Coia, et al., "Nucleotide and Complete Amino Acid Sequences of Kunjin Virus: Definitive Gene Order and Characteristics of the Virus–specified Proteins," *J. Gen. Virol.* 69:1–21 (1988).

Coursaget, et al., "Virus–Like Particles Associated with Non–A, Non–B Hepatitis," *The Lancet,* 14 Jul. 1979, p. 92.

Dalgarno, et al., "Ross River Virus 26 S RNA: Complete Nucleotide Sequence and Deduced Sequence of the Encoded Structural Proteins," *Virology* 129:170–187 (1983).

Dalgarno, et al., "Partial nucleotide sequence of the Murray Valley encephalitis virus genome. Comparison of the encoded polypeptides with Yellow Fever virus structrual and non–structural proteins," *J. Mol. Biol.* 187:309–323 (1986).

Davis, et al., "Isolation of cDNA Clones for Differentially Expressed Genes of the Human Parasite *Schistosoma mansoni,*" *Proc. Natl. Acad. Sci. USA* 83:5534–5538 (1986).

Denniston, et al., "Cloned Fragment of the Hepatitis Delta Virus RNA Genome: Sequence and Diagnostic Application," *Science* 232:873–875 (1986).

Deubel, et al., "Nucleotide Sequence and Deduced Amino Acid Sequence of the Structural Proteins of Dengue Type 2 Virus, Jamaica Genotype," *Virology* 155:365–377 (1986).

Dienstag, et al., "Non–A, Non–B Hepatitis: Evolving Epidemiologic and Clinical Perspectives," *Seminars in Liver Disease* 6(1):67–81 (1986).

Dientag, et al., "Circulating Immune Complexes in Non–A, Non–B Hepatitis," *Lancet* 1:1265–1267 16 Jun. 1979.

Donelson, et al., "Construction of *Onchocerca volvulus* cDNA libraries and partial characterization of the cDNA for a major antigen," *Mol. Biochem. Parasitol.* 31:241–250 (1988), (previously considered in US 08/103,961, reference V.5).

Druilhe, et al., "Species–and Stage–specific antigens in exoerythrocytic stages of *Plasmodium falciparum,*" *Am. J. Trop. Med. Hyg.* 33(3):336–341 (1984); (previously considered in US 08/103,961, reference V.28).

Edwards, *Immunoassay: An Introduction* (London, 1985); (previously considered in US 08/103,961, reference I.A.32).

Ezzell, "Candidate Cause Identified of Non-A, Non-B Hepatitis," *Nature* 333:195 (1988); (previously considered in US 07/456,637, reference FP; and US 08/103,961, reference I.B.114).

Faragher, Ph.D. thesis, "Sequence Studies on Natural and Laboratory-Derived Virulence Variants of Ross River Virus," *Australian National University Lab* Mar. 1987; (previously considered in US 08/103,961, reference I.A.33, and VI.29).

Faragher, et al., "Analysis of Ross River Virus Genomic RNA Using *Hae*III Digests of Single-Stranded cDNA to Infected-Cell RNA and Virion RNA," *Virology* 141:248-256 (1985); (previously considered in US 08/103, 961, reference I.A.34).

Faragher, et al., "Genome Sequences of a Mouse-Avirulent and a Mouse-Virulent Strain of Ross River Virus," *Virology* 163:509-526 (1988); (previously considered in US 08/103, 961, reference I.A.35).

Feinstone, et al., "Evidence for Non-A, Non-B Viruses," *Viral Hepatitis and Delta Infection*, pp. 29-39 (1983); (previously considered in US 08/103,961, reference I.A.36).

Glover, (ed.), *DNA Cloning Techniques: A Practical Approach*, (1985), IRL Press, Oxford; (previously considered in US 08/103,961, reference I.A.41).

Goelet, et al., "Nucleotide sequence of tobacco mosaic virus RNA," *Proc. Natl. Acad. Sci. USA* 79:5818-5822 (1982); (previously considered in US 08/103,961, reference V.9).

Guerin-Marchand, "A Liver-Stage-Specific Antigen of *Plasmodium Falciparum* Characterized by Gene Cloning," *Nature* 329:164-167 (1987); (previously considered in US 07/456,637, reference FFN; and US 08/103,961, reference I.B.143).

Hakim, "Isolation and Functional Property of mRNA Coding for Hepatitis A, B and Non-A, Non-B Viral Particles from Human Sera," *Naturwissenschaften* 73:45-47 (1986); (previously considered in US 07/456,637, reference HS; and US 08/103,961, reference I.B.147).

Hahn, et al., "Nucleotide Sequence of Dengue 2 RNA and Comparison of the Encoded Proteins with Those of Other Flaviviruses," *Virology* 162:167-180 (1988); (previously considered in US 08/103,961, reference V.18).

Hardy, (ed.), *Plasmids: A Practical Approach*, (IRL Press, Oxford).

He, et al., "Determining the Size of Non-A, Non-B Hepatitus Virus by Filtration," *J. Infect. Dis.* 156(4):636-640 (1987).

Hollinger, et al., "Transfusion-Transmitted viruses study: Experimental evidence for Two Non-A, Non-B Hepatitis Agents," *J. Infect. Dis.* 142(3):400-407 (1980).

Houghton, et al., "Molecular Biology of the Hepatitis C Viruses: Implications for Diagnosis, Development and Control of Viral Disease," *Hepatology* 14(2):381 (1991).

Huyhn, et al., "Constructing and Screening cDNA Libraries in Σgt10 and Σgt11," *DNA Cloning: A Practical Approach*, vol. 1, Chpt. 2, pp. 49-78 (Glover, ed.).

Imai, et al., "Molecular cloning of double-stranded RNA virus genomes," *Proc. Natl. Acad. Sci. USA* 80:373-377 (1983).

Kemp, et al., "Expression of *Plasmodium falciparum* Blood- Stage Antigens in *Escherchia coli*: Detection with Antibodies from Immune Humans," *Proc. Natl. Acad. Sci. USA* 80:3787-3791 (1983).

Knodell, et al., "Development of Chronic Liver Disease After Acute Non-A, Non-B Post-Transfusion Hepatitis, Role of K-Globulin prophylaxis in its Prevention," *Gastroenterology* 72(5):902-909 (1977).

Kubo, et al., "A cDNA Fragment of Hepatitis C Virus Isolated from an Implicated Donor of post-transfusion non-A, non-B hepatitis in Japan," *Nucl. Acids Res.* 17(24):10367-10372 (1989).

Lopez, et al., "Cloning of the I Chain of Human Platelet Glycoprotein Ib: A Transmembrane Protein with Homology to Leucine-Rich I2-Glycoprotein," *Proc. Natl. Acad. Sci. USA* 84:5615-5619 (1987).

Mackow, et al., "The Nucleotide Sequence of Dengue Type 4 Virus: Analysis of Genes Coding for Nonstructural Proteins," *Virology* 159(2):217-228 (1987).

Mandl, et al., "Genome Sequence of Tick-Borne Encephalitis Virus (Western Subtype) and Comparative Analysis of Nonstructural Proteins with Other Flaviviruses," *Virology* 173:291-301 (1989).

Miller, et al., "Hepatitis C virus shares amino acid sequences similarity with pestiviruses and flaviviruses as well as members of two plant virus supergroups," *Proc. Natl. Acad. Sci. USA* 87:2057-2061 (1990); (previously considered in US 08/103,961, reference V. 27).

Molenaar, et al., "Structure and Organization of Two Links Ribosomal Protein Genes in Yeast," *Nucleic Acids Res.* 12(19):7345 (1984).

Nakada, et al., "Complete Nucleotide Sequence of the Influenza C/California/78 Virus Nucleoprotein," *Virus Res.* 1:433-441 (1984).

Neurath, et al., "Strategies for Detection of Transfusion-Transmitted Viruses Eluding Identification by Conventional Serologic Tests. II) Detection of Host DNA in Human Plasmas with Elevated Alanine Aminotransferase," *J. Virol. Meth.* 8:73-86 (1984).

Oellerich, "Enzyme-Immunoassay: A Review," *J. Clin. Chem. Clin. Biochem.* 22:895-904 (1984).

Okamoto, et al., "Full-Length Sequence of a Hepatitis C Virus Genome Having Poor Homology to Reported Isolates: Comparative Study of Four Distinct Genotypes," *Virol.* 188:331-341 (1992).

Old & Primrose, *Principles of* Old & Primrose, *Principles of Gene Manipulation*, 3rd Ed. (1985) Blackwell Scientific Publication, p. 113.

O'Sullivan, "Clinical and Biochemical Analysis," *Enzyme Immunoassay*, vol. 14, Chpt. 3 (1984).

Overby, "Serology of Liver Diseases," *Current Hepatology* 7:35-67 (1987).

Prince, et al., "Hepatitis C virus (HCV): Characterization of virus specific antigens and associated particles," *Gastroenterology* 77(5):A33 (1979).

Prince, "Non-A, Non-B Hepatitis Viruses," *Ann. Rev. Microbiol.* 37:217-232 (1983).

Rice, et al., "Nucleotide Sequence of Yellow Fever Virus: Implications for Flavivirus Gene Expression and Evolution," *Science* 229:726-733 (1985).

Rice, et al., "Nucleotide sequence of the 26S mRNA of Sindbis virus and deduced sequence of the encoded virus structural proteins," *Proc. Natl. Acad. Sci. USA*, 78(4):2062-2066 (1981).

Rice, et al., "Synthesis, Cleavage and Sequence Analysis of DNA Complementary to the 26 S Messenger RNA of Sindbis Virus," *J. Mol. Biol.* 150:315-340 (1981).

Robinson, et al., "The Enigma of Non-A, Non-B Hepatitis" *J. Infect. Dis.* 145(3):387-395 (1982).

Scallon, et al., "Cloning of a *Schistosoma japonicum* Gene Encoding a Major Immunogen Recognized by Hyperinfected Rabbits," *Mol. Biochem. Parasitol.* 24:237–245 (1987).

Schuurs, et al., "Enzyme Immunoassay," *Clin. Chim. ACTA* 81:1–40 (1977).

Seikagaku Jiten, "Antigen Determinant," *Dictionary of Biochemistry*, 1st Ed. p. 435 (1984).

Seto, et al., "Detection of Reverse Transciptase Activity in Association with the Non–A, Non–B Hepatitis Agent(s)," *The Lancet* 8409:941–943 (1984).

Shih, et al., "Non–A, Non–B Hepatitis: Advances and Unfulfilled Expectations of the First Decade," *Prog. in Liver Diseases*, vol. VIII (Grune & Stratton, publ.), Chpt. 24, pp. 433–452.

Shimizu, et al., "Non–A, Non–B Hepatitis: Ultrastructural Evidence for Two Agents in Experimentally Infected Chimpanzees," *Science* 205:197–200 (1979).

Shirachi, et al., "Hepatitis C" antigen in Non–A, Non–B post-transfusion hepatitis, *The Lancet* 8095:853–856 (1978).

Stahl, et al., "Differential Antibody Screening of Cloned *Plasmodium falciparum* Sequences Expressed in *Escherichia coli*: Procedure for Isolation of Defined Antigens and Analysis of Human Antisera," *Proc. Natl. Acad. Sci. USA* 81:2456–2460 (1984).

Strauss, et al., "Replication of Alphaviruses and Flaviviruses: Proteolytic Processing of Polyproteins," *Positive Strand RNA Viruses* (Alan Liss, Inc. 1987) pp. 209–225.

Sumiyoshi, et al., "Complete Nucleotide Sequence of the Japanese Encephalitis Virus Genome RNA," *Virology* 161:497–510 (1987); (reference V.16).

Tabor, et al., "Detection of an Antigen–Antibody System in Serum Associated with Human Non–A, Non–B Hepatitis," *J. Med. Virol.* 4:161–169 (1979).

Taylor, et al., "Efficient Transcription of RNA into DNA by avian sarcoma virus polymerase," *Biochim. Biophys. Acta* 442:324–330 (1976).

Trent, et al. "Partial Nucleotide Sequence of St. Louis Encephalitis Virus RNA: Structural Proteins, NSI, ns2a, and ns2b," *Virology* 156:293–304 (1987).

Van der Poel, et al., "Confirmation of Hepatitis C Virus Infected by New Four–Antigen Recombinant Immunoblot Assay," *The Lancet* 337:317–319 (1991).

Vogel, et al., "Production of a recombinant antigen of Echinococcus multilocularis with high immunodiagnostic sensitivity and specificity," *Mol. Biochem. Parasitol.* 31:117–126 (1988).

Vrati, et al., "Ross River Virus Mutant with a Deletion in the E2 Gene: Properties of the Virion, Virus–Specific Macromolecule Synthesis and Attenuation of Virulence for Mice," *Virology* 151:222–232 (1986).

Wang, et al., "Structure, sequence and expression of hepatitis delta (Λ) viral genome," *Nature* 323:508–514 (1986).

Weiner, et al., "Hepatitis Delta (Λ) cDNA Clones: Undetectable Hybridization to Nucleic Acids from Infectious Non–A, Non–B Hepatitis Materials and Hepatitis B DNA," *J. Med. Virol.* 21:239–247 (1987).

Weiner, et al., "HCV: Detection of Hepatitis C Viral Sequences in Non–A, Non–B Hepatitis," *The Lancet* 335:1–3 (1990).

Wengler, et al., "Analysis of Structural Properties which Possibly Are Characteristic for the 3'–Terminal Sequence of the Genome RNA of Flaviviruses," *J. Gen. Virol.* 67:1183–1188 (1986).

Yaegashi, et al., "Partial Sequence Analysis of Cloned Dengue Virus Type 2 Genome," *Gene* 46:257 (1986).

Young, et al., "Efficient Isolation of Genes by Using Antibody Probes," *Proc. Natl. Acad. Sci. USA* 80:1194–1198 (1983).

Young, et al., "Yeast RNA polymerase II genes: Isolation with antibody probes," *Science* 222:778–782 (1983).

*Newswatch* 5:8 (1985).

*The New York Times*, Friday, Apr. 21, 1989, p. 1.

Martin, et al., *Arch. of Virol.* 61:87–103 (1979) (ref. 52).

Sewell, et al., *Proc. Natl. Acad. Sci. USA* 83:8718–8722 (1986) (ref. 18).

Zhao, et al., *Virology* 155:77–88 (1986) (ref 31).

Letter dated Oct. 16, 1989, from Mr. Lanman at the NIH to Robert Blackburn at Chiron.

Opinion of Professor Donald Chisum Jun. 1991.

"Agreement of Settlement" dated Apr. 3, 1990, between Chiron Corporation and the Centers for Disease Control.

"Independent Legal Opinion Concerning Hepatitis C Inventorship Dispute", Jun. 1991.

Memorandum Re Interviews of Dr. Qui–Lim Choo and Dr. George Kuo dated May 8, 1991.

Memorandum Re Interview of Dr. Michael Houghton dated May 8, 1991.

Memorandum Re Interview of Dr. Daniel Bradley dated Apr. 11, 1991.

Memorandum Re Interviews of Dr. Amy Weiner and Dr. Gary Van Nest dated Apr. 30, 1993.

Memorandum Re Interview of Dr. Lacy Overby dated Jun. 21, 1991.

Memorandum dated Nov. 11, 1987 by Dr. Michael Houghton.

Memorandum by Dr. Michael Houghton (undated).

Chiron Laboratory Notebook #1298, pp. 184–190, 192 (Nov., 1986).

Memorandum by Dr. Houghton, dated Nov. 10, 1987.

Inventorship Opinion of Gladys Monroy dated Jun. 7, 1988.

Letter dated Oct. 16, 198 from Mr. Lanman of the NIH to Robert Blackburn of Chiron Corporation.

Bradley, et al., *Prog. Med. Virol.* 37:101–135 (1990).

Weiner, et al., *J. Virol.* 62(2):594–599 (1988).

Choo, et al., "Genetics, Organization and diversity of the Hepatitis C virus," *Proc. Natl. Acad. Sci. USA* 88:1–5 (1991).

*Proc. Japan Acad.*, 65,ser.V. No.9, pp.219–223 (1989).

*Methods in Enzymology* vol. 155, part F (1987).

Bradley, "Non–A/Non–B Hepatitus in Experimentally Infected Chimpanzees: Cross Challenge and Electron Microscopic Studies," *J Med Virol* 6:185–201 (1980).

Dialog Computer Printout.

Alter, "Transfusion–Associated Non–A, Non–B Hepatitis: The First Decade," *Viral Hepatitis and Liver Disease*, (Zuckermann, Ed.) p.537.

Arima, et al., "Cloning of Serum RNA Associated with Hepatitis C Infection Suggesting Heterogeneity of the Agent(s) Responsible for Infection," *Chemical Abstract*, 112(11):441 (1990).

Arima, "Cloning of a cDNA Associated with Acute and Chronic Hepatitis C Infection Generated from Patients Serum RNA," *Chem. Abstract*, 112(1):209 (1990).

Arima, "A Lambda gt11–cDNA Clone Specific for Chronic Hepatitis C Generated from Pooled Serum Presumably Infected by Hepatitis C Virus," *Chem. Abstract*, 112(7):169 (1990).

Boender, et al., "Fragmented Chromosomal DNA in Sera of Patients with Hepatitis A, B, and Non–A, Non–B," *Viral Hepatitis and Liver Disease* (Zuckerman, ed.) pp. 588–591 (1988).

Bradley, et al., "Non–A, Non–B Hepatitis in Experimentally Infected Chimpanzees:Comparative Morphology of Virus––Induced Ultrastructural Changes," *Hepatitis Viruses and Hepatocellular Carcinoma,* pp. 226–260 (1985).

Brotman, et al., "Interference Beween Non–A, Non–B and Hepatitis B Virus Infection in Chimpanzees," *J. Med. Vir.,* 11:191–205 (1983).

Neurath, et al., "An Antigen Detected Frequently in Human Sera with Elevated Levels of Alanine Aminotransferase: A Potential Marker for Non–A, Non–B Hepatitis," *J. Gen. Virol.,* 48:285–295 (1980).

Shimizu, et al., "Production of Antibody Associated with Non–A, Non–B Hepatitis In A Chimpanzee Lymphoblastoid Cell Line Established by in vitro Transformation with Epstein–Barr Virus," *Proc. Natl. Acad. Sci. USA* 82:2138–2142 (1985).

Shimizu, et al., "Further Studies by Immunofluorescence of the Monoclonal Antibodies Associated with Experimental Non–A, Non–B Hepatitis in Chimpanzees and Their Relation to Delta Hepatitis," *Hepatology,* 6:1329–1333 (1986).

Prince, et al., "Isolation of a Virus from Chimpanzee Liver Cell Cultures Inoculated with Sera Containing the Agent of Non–A, Non–B Hepatitis," *The Lancet,* 10 Nov. 1984, pp. 1071–1075.

Arima, et al., "Serum RNA Associated with Blood–Transmitted Non–A, Non–B Hepatitis," *Hepatology,* 8:1275 (1988).

Arima, et al., "Cloning of Serum RNA Associated with Hepatitis C Infection Suggesting Heterogeneity of the Agent(s) Responsible for Infection," *Gastroenterol. Jpn.,* 25(6):685–691 (1989).

Bradley, et al., "Non–A, Non–B Hepatitis in Experimentally Infected Chimpanzees: Comparative Morphology of Virus––Induced Ultrastructural Changes," *Academic Press Japan,* (1985).

Bradley, et al., "Non–A, Non–B Hepatitis:Research Progress and Current Perspectives," *Dev. Biol. Standard,* 54:63–73 (1983).

Bradley, et al., "Parenterally Transmitted Non–A, Non–B Hepatitis Virus–Specific Antibody Response Patters in Hepatitis C Virus–Infected Chimpanzees," *Gastroenterology,* 99:1054–1060 (1990).

Bradley, et al., "Transmission of Non–A, Non–B Hepatitis to Chimpanzees:Recovery of Virus–Like Particles," *Abstr. Ann. Mtg. Am. Soc. Microbiol.,* 79:267 (1979).

Bradley, et al., "Aetiological Agent of Enterically Transmitted Non–A, Non–B Hepatitis," *J. Gen. Virol.,* 69:731–7638 (1988).

Bradley, et al., "Non–A, Non–B, Hepatitis in Chimpanzees:Interference with Acute Hepatitis A Virus and Chronic Hepatitis B Virus Infectious," *J. Med. Virol.* 11:207–213 (1983).

Bradley, et al., "Persistant Non–A, Non–B Hepatitis in Experimentally Infected Chimpanzees," *J. Infect. Dis.,* 143:210–218 (1981).

Bradley, et al., "Viroids and Viral Hepatitis in Marmosets," *Nature,* 248:172 (1974).

Bradley, et al., "Guest Lecture: Recrudescence of Non–A, Non–B Hepatitis in Persistently Infected Chimpanzees," *Proc. Int'l Hepatitis Workshop* (undated).

Bradley, et al., "Virus of Enterically Transmitted Non–A, Non–B Hepatitis," *The Lancet* 9 Apr. 1988, p. 819.

Brotman, et al., "Non–A, Non–B Hepatitis:Is There More Than A Single Blood–Borne Strain?," *J. Infect. Dis.,* 151:618–625 (1985).

Dienstag, "Non–A, Non–B Hepatitis I Recognition, Epidemiology and Clinical Features," *Gastroenterology,* 85:439–462 (1983).

Dienstag, "Non–A, Non–B Hepatitis II Experimental Transmission, Putative Virus Agents and Markers, and Prevention," *Gastroenterology,* 85:743–768 (1983).

Hallam, "Non–A, Non–B Hepatitis:Reverse Transcriptase Activity?," *The Lancet,* 21 Sep. 1985, p. 665.

Itoh, et al., "Lack of Detectable Reverse–Transcriptase Activity in Human and Chimpanzee Sera with a High Infectivity for Non–A, Non–B Hepatitis," *J. Gen. Virol.,* 67:777 (1986)

Linke, et al., "Non–A, Non–B Hepatitis Infection Does Not Result in the Production of Abundant Poly–A–Containing Messenger RNAs," *Viral Hepatitis and Liver Disease* (Zuckerman, ed.) pp.564–567 (1988).

Alter, "Transfusion–Associated Non–A, Non–B Hepatitis-:The First Decade," *J. Med. Virol.,* 21:43A (1987).

Alter, et al., "Non–A, Non–B Hepatitis:Its Relationship to Cytomegalovirus, to Chronic Hepatitis and to Direct and Indirect Test Methods," *Viral Hepatits, 1981 Int'l Symposium,* pp. 279–294 (1981).

Feinstone, et al., "Non–A, Maybe–B Hepatitis," *New England J. Med.,* 311(3):185–189 (1973).

Fraenkel–Conrat, et al. (ed.), *The Viruses:The Togaviridae and Flaviviridae* (1986), Plenum Press).

Hellings, et al, "Transmission of Non–A, Non–B Hepatitis by Leucocyte Preparations," *Viral Hepatitis and Liver Disease (Zuckerman, ed.)* pp. 543–549 (1988).

Alter, et al., "Non–A, Non–B:Observations on the First Decade," *Viral Hepatitis and Liver Disease* (Vyas, et al. eds.) pp. 345–354 (1984).

Charney, et al., "Analysis by Hybridization with HBV DNA of Hepatocellular DNA from Patients with Chronic Non–A, Non–B Hepatitis," *Viral Hepatitis: 1981 International Symposium* (Szmuness, et al., eds. (pp. 656–657) 1985, Franklin Institute Press).

F. Hoffman LaRoche AG: Opposition to AUSTRALIAN Application No. 638719, Jan. 10, 1994.

Arnaout et al., "Amino Acid Sequence of the Alpha Subunit of Human Leukocyte Adhesion Receptor Mo1 (Complement Receptor Type 3)," *J. Cell. Biol.* 106:2153–2158 (1988).

Arnaout et al., "Molecular cloning of the alpha subunit of human and guinea pig leukocyte adhesion glycoprotein Mo1: Chromosomal localization and homology to the alpha subunits of integrins," *Proc. Natl. Acad. Sci. USA* 85:2776–2780 (1988).

Bensi et al., "Structure and expression of the human haptoglobin locus," *EMBO J.* 4:119–126 (1985).

Boelin et al., "The plasmid–encoded Yop2b protein of *Yersinia pseudotuberculosis* is a virulence determinant regulated by calcium and temperature at the level of transcription," *Mol. Microbiol.* 2:237–245 (1988).

Boss et al., "Sequence Analysis of the Human Major Histocompatibility Gene SXα," *Mol. Cell. Biol.* 5:2677–2683 (1985).

Broderick et al., "Comparative anatomy of the human APRT gene and enzyme: Nucleotide sequence divergence and conservation of a nonrandom CpG dinucleotide arrangement," *Proc. Natl. Acad. Sci. USA* 84:3349–3353 (1987).

Bzik et al., "Nucleotide Sequence Specifying the Glycoprotein Gene, gB, of Herpes Simplex Virus Type 1," *Virology* 133:301–314 (1984).

Bzik et al., "The Nucleotide Sequence of the gB Glycoprotein Gene of HSV-2 and Comparison with the Corresponding Gene of HSV-1," *Virology* 155:322–333 (1986).

Cheah et al., "Identification and characterization of the human type II collagen gene (COL2AI)," *Proc. Natl. Acad. Sci. USA* 82:2555–2559 (1985).

Comb et al., "Primary Structure of the Human Proenkephalin Gene," *DNA* 2:213–229 (1983).

Cool et al., "Characterization of Human Blood Coagulation Factor XII cDNA," *J. Biol. Chem.* 260:13666–13676 (1985).

Cool et al., "Characterization of the Human Blood Coagulation Factor XII Gene," *J. Biol. Chem.* 262:13662–13673 (1987).

Corbi et al., "The Human Leukocyte Adhesion Glycoprotein Mac-1 (Complement Receptor Type 3, CD11b) Alpha Subunit," *J. Biol. Chem.* 263:12403–12411 (1988).

Glasser et al., "Two SP–C Genes Encoding Human Pulmonary Surfactant Proteolipid," *J. Biol. Chem.* 263:10326–10331 (1988).

Hoefsloot et al., "Primary structure and processing of lysosomal alpha–glucosidase, homology with the intestinal sucrase–isomaltase complex," *EMBO J.* 7:1697–1704 (1988).

Knoll et al., "Nucleotide Sequence of the Human Placental Alkaline Phosphatase Gene," *J. Biol. Chem.* 263:12020–12027 (1988).

Kousarides et al., "Large–Scale Rearrangement of Homologous Regions in the Genomes of HCMV and EBV," *Virology* 157:397–413 (1987).

Luk et al., "Messenger RNA Encoding the Phosphoprotein (P) Gene of Human Parainfluenza Virus 3 Is Bicistronic," *Virology* 153:318–325 (1986).

Matsuo et al., "Persistence of the Entire Epstein–Barr Virus Genome Integrated into Human Lymphocyte DNA," *Science* 226:1322–1325 (1984).

McGeoch et al., "Complete DNA sequence of the short repeat region in the genome of herpes simplex virus type I," *Nucleic Acids Res.* 14:1727–1745 (1986).

McLafferty et al., "Nucleotide Sequence and Characterization of a Repetitive DNA Element from the Genome of *Bordetella pertussis* with Characteristics of an Insertion Sequence," *J. Gen. Microbiol.* 134:2297–2306 (1988).

Noda et al., "Isolation and structural organization of the human preproenkephalin gene," *Nature* 297:431–434 (1982).

Pohlner et al., "Nucleotide sequence of *ompV*, the gene for a major *Vibrio cholerae* outer membrane protein," *Mol. Gen. Genet.* 205:494–500 (1986).

Weiss et al., "Isolation and characterization of a human collagen alpha–1–like gene from a cosmid library," *Nucleic Acids Research.* 10:1981–1994 (1982).

```
                                              -341 GCCAGCCCCCTGATGGGGGCGA
                                                   CGGTCGGGGGACTACCCCCGCT

-319 CACTCCACCATGAATCACTCCCCTGTGAGGAACTACTGTCTTCACGCAGAAAGCGTCTAG
     GTGAGGTGGTACTTAGTGAGGGGACACTCCTTGATGACAGAAGTGCGTCTTTCGCAGATC

-259 CCATGGCGTTAGTATGAGTGTCGTGCAGCCTCCAGGACCCCCCCTCCCGGGAGAGCCATA
     GGTACCGCAATCATACTCACAGCACGTCGGAGGTCCTGGGGGGAGGGCCCTCTCGGTAT

-199 GTGGTCTGCGGAACCGGTGAGTACACCGGAATTGCCAGGACGACCGGGTCCTTTCTTGGA
     CACCAGACGCCTTGGCCACTCATGTGGCCTTAACGGTCCTGCTGGCCCAGGAAAGAACCT

-139 TCAACCCGCTCAATGCCTGGAGATTTGGGCGTGCCCCCGCAAGACTGCTAGCCGAGTAGT
     AGTTGGGCGAGTTACGGACCTCTAAACCCGCACGGGGGCGTTCTGACGATCGGCTCATCA

- 79 GTTGGGTCGCGAAAGGCCTTGTGGTACTGCCTGATAGGGTGCTTGCGAGTGCCCCGGGAG
     CAACCCAGCGCTTTCCGGAACACCATGACGGACTATCCCACGAACGCTCACGGGGCCCTC

- 19 GTCTCGTAGACCGTGCACC
     CAGAGCATCTGGCACGTGG
     ---                    Arg  Thr
     MetSerThrAsnProLysProGlnLysLysAsnLysArgAsnThrAsnArgArgProGln
  1  ATGAGCACGAATCCTAAACCTCAAAAAAAAAACAAACGTAACACCAACCGTCGCCCACAG
     TACTCGTGCTTAGGATTTGGAGTTTTTTTTTTGTTTGCATTGTGGTTGGCAGCGGGTGTC

AspValLysPheProGlyGlyGlyGlnIleValGlyGlyValTyrLeuLeuProArgArg
  61 GACGTCAAGTTCCCGGGTGGCGGTCAGATCGTTGGTGGAGTTTACTTGTTGCCGCGCAGG
     CTGCAGTTCAAGGGCCCACCGCCAGTCTAGCAACCACCTCAAATGAACAACGGCGCGTCC

GlyProArgLeuGlyValArgAlaThrArgLysThrSerGluArgSerGlnProArgGly
 121 GGCCCTAGATTGGGTGTGCGCGCGACGAGAAAGACTTCCGAGCGGTCGCAACCTCGAGGT
     CCGGGATCTAACCCACACGCGCGCTGCTCTTTCTGAAGGCTCGCCAGCGTTGGAGCTCCA

ArgArgGlnProIleProLysAlaArgArgProGluGlyArgThrTrpAlaGlnProGly
 181 AGACGTCAGCCTATCCCCAAGGCTCGTCGGCCCGAGGGCAGGACCTGGGCTCAGCCCGGG
     TCTGCAGTCGGATAGGGGTTCCGAGCAGCCGGGCTCCCGTCCTGGACCCGAGTCGGGCCC

TyrProTrpProLeuTyrGlyAsnGluGlyCysGlyTrpAlaGlyTrpLeuLeuSerPro
 241 TACCCTTGGCCCCTCTATGGCAATGAGGGCTGCGGGTGGCGGGATGGCTCCTGTCTCCC
     ATGGGAACCGGGGAGATACCGTTACTCCCGACGCCCACCCGCCCTACCGAGGACAGAGGG

ArgGlySerArgProSerTrpGlyProThrAspProArgArgArgSerArgAsnLeuGly
 301 CGTGGCTCTCGGCCTAGCTGGGGCCCCACAGACCCCCGGCGTAGGTCGCGCAATTTGGGT
     GCACCGAGAGCCGGATCGACCCCGGGGTGTCTGGGGCCGCATCCAGCGCGTTAAACCCA

LysValIleAspThrLeuThrCysGlyPheAlaAspLeuMetGlyTyrIleProLeuVal
 361 AAGGTCATCGATACCCTTACGTGCGGCTTCGCCGACCTCATGGGGTACATACCGCTCGTC
     TTCCAGTAGCTATGGGAATGCACGCCGAAGCGGCTGGAGTACCCCATGTATGGCGAGCAG

GlyAlaProLeuGlyGlyAlaAlaArgAlaLeuAlaHisGlyValArgValLeuGluAsp
 421 GGCGCCCCTCTTGGAGGCGCTGCCAGGGCCCTGGCGCATGGCGTCCGGGTTCTGGAAGAC
     CCGCGGGGAGAACCTCCGCGACGGTCCCGGGACCGCGTACCGCAGGCCCAAGACCTTCTG

Thr
     GlyValAsnTyrAlaThrGlyAsnLeuProGlyCysSerPheSerIlePheLeuLeuAla
 481 GGCGTGAACTATGCAACAGGGAACCTTCCTGGTTGCTCTTTCTCTATCTTCCTTCTGGCC
     CCGCACTTGATACGTTGTCCCTTGGAAGGACCAACGAGAAAGAGATAGAAGGAAGACCGG
```

FIG. 1A

```
         LeuLeuSerCysLeuThrValProAlaSerAlaTyrGlnValArgAsnSerThrGlyLeu
 541     CTGCTCTCTTGCTTGACTGTGCCCGCTTCGGCCTACCAAGTGCGCAACTCCACGGGGCTT
         GACGAGAGAACGAACTGACACGGGCGAAGCCGGATGGTTCACGCGTTGAGGTGCCCCGAA

TyrHisValThrAsnAspCysProAsnSerSerIleValTyrGluAlaAlaAspAlaIle
 601     TACCACGTCACCAATGATTGCCCTAACTCGAGTATTGTGTACGAGGCGGCCGATGCCATC
         ATGGTGCAGTGGTTACTAACGGGATTGAGCTCATAACACATGCTCCGCCGGCTACGGTAG

LeuHisThrProGlyCysValProCysValArgGluGlyAsnAlaSerArgCysTrpVal
 661     CTGCACACTCCGGGGTGCGTCCCTTGCGTTCGTGAGGGCAACGCCTCGAGGTGTTGGGTG
         GACGTGTGAGGCCCCACGCAGGGAACGCAAGCACTCCCGTTGCGGAGCTCCACAACCCAC

AlaMetThrProThrValAlaThrArgAspGlyLysLeuProAlaThrGlnLeuArgArg
 721     GCGATGACCCCTACGGTGGCCACCAGGGATGGCAAACTCCCCGCGACGCAGCTTCGACGT
         CGCTACTGGGGATGCCACCGGTGGTCCCTACCGTTTGAGGGGCGCTGCGTCGAAGCTGCA

HisIleAspLeuLeuValGlySerAlaThrLeuCysSerAlaLeuTyrValGlyAspLeu
 781     CACATCGATCTGCTTGTCGGGAGCGCCACCCTCTGTTCGGCCCTCTACGTGGGGGACCTA
         GTGTAGCTAGACGAACAGCCCTCGCGGTGGGAGACAAGCCGGGAGATGCACCCCCTGGAT

CysGlySerValPheLeuValGlyGlnLeuPheThrPheSerProArgArgHisTrpThr
 841     TGCGGGTCTGTCTTTCTTGTCGGCCAACTGTTCACCTTCTCTCCCAGGCGCCACTGGACG
         ACGCCCAGACAGAAAGAACAGCCGGTTGACAAGTGGAAGAGAGGGTCCGCGGTGACCTGC

ThrGlnGlyCysAsnCysSerIleTyrProGlyHisIleThrGlyHisArgMetAlaTrp
 901     ACGCAAGGTTGCAATTGCTCTATCTATCCCGGCCATATAACGGGTCACCGCATGGCATGG
         TGCGTTCCAACGTTAACGAGATAGATAGGGCCGGTATATTGCCCAGTGGCGTACCGTACC

Val
         AspMetMetMetAsnTrpSerProThrThrAlaLeuValMetAlaGlnLeuLeuArgIle
 961     GATATGATGATGAACTGGTCCCCTACGACGGCGTTGGTAATGGCTCAGCTGCTCCGGATC
         CTATACTACTACTTGACCAGGGGATGCTGCCGCAACCATTACCGAGTCGACGAGGCCTAG

ProGlnAlaIleLeuAspMetIleAlaGlyAlaHisTrpGlyValLeuAlaGlyIleAla
1021     CCACAAGCCATCTTGGACATGATCGCTGGTGCTCACTGGGGAGTCCTGGCGGGCATAGCG
         GGTGTTCGGTAGAACCTGTACTAGCGACCACGAGTGACCCCTCAGGACCGCCCGTATCGC

TyrPheSerMetValGlyAsnTrpAlaLysValLeuValValLeuLeuPheAlaGly
1081     TATTTCTCCATGGTGGGGAACTGGGCGAAGGTCCTGGTAGTGCTGCTGCTATTTGCCGGC
         ATAAAGAGGTACCACCCCTTGACCCGCTTCCAGGACCATCACGACGACGATAAACGGCCG

ValAspAlaGluThrHisValThrGlyGlySerAlaGlyHisThrValSerGlyPheVal
1141     GTCGACGCGGAAACCCACGTCACCGGGGGAAGTGCCGGCCACACTGTGTCTGGATTTGTT
         CAGCTGCGCCTTTGGGTGCAGTGGCCCCCTTCACGGCCGGTGTGACACAGACCTAAACAA

SerLeuLeuAlaProGlyAlaLysGlnAsnValGlnLeuIleAsnThrAsnGlySerTrp
1201     AGCCTCCTCGCACCAGGCGCCAAGCAGAACGTCCAGCTGATCAACACCAACGGCAGTTGG
         TCGGAGGAGCGTGGTCCGCGGTTCGTCTTGCAGGTCGACTAGTTGTGGTTGCCGTCAACC

HisLeuAsnSerThrAlaLeuAsnCysAsnAspSerLeuAspThrGlyTrpLeuAlaGly
1261     CACCTCAATAGCACGGCCCTGAACTGCAATGATAGCCTCAACACCGGCTGGTTGGCAGGG
         GTGGAGTTATCGTGCCGGGACTTGACGTTACTATCGGAGTTGTGGCCGACCAACCGTCCC

LeuPheTyrHisHisLysPheAsnSerSerGlyCysProGluArgLeuAlaSerCysArg
1321     CTTTTCTATCACCACAAGTTCAACTCTTCAGGCTGTCCTGAGAGGCTAGCCAGCTGCCGA
         GAAAAGATAGTGGTGTTCAAGTTGAGAAGTCCGACAGGACTCTCCGATCGGTCGACGGCT
```

FIG. 1B

```
      ProLeuThrAspPheAspGlnGlyTrpGlyProIleSerTyrAlaAsnGlySerGlyPro
1381  CCCCTTACCGATTTTGACCAGGGCTGGGGCCCTATCAGTTATGCCAACGGAAGCGGCCCC
      GGGGAATGGCTAAAACTGGTCCCGACCCCGGGATAGTCAATACGGTTGCCTTCGCCGGGG

AspGlnArgProTyrCysTrpHisTyrProProLysProCysGlyIleValProAlaLys
1441  GACCAGCGCCCTACTGCTGGCACTACCCCCCAAAACCTTGCGGTATTGTGCCCGCGAAG
      CTGGTCGCGGGGATGACGACCGTGATGGGGGGTTTTGGAACGCCATAACACGGGCGCTTC

SerValCysGlyProValTyrCysPheThrProSerProValValValGlyThrThrAsp
1501  AGTGTGTGTGGTCCGGTATATTGCTTCACTCCCAGCCCCGTGGTGGTGGGAACGACCGAC
      TCACACACACCAGGCCATATAACGAAGTGAGGGTCGGGGCACCACCACCCTTGCTGGCTG

ArgSerGlyAlaProThrTyrSerTrpGlyGluAsnAspThrAspValPheValLeuAsn
1561  AGGTCGGGCGCGCCCACCTACAGCTGGGGTGAAAATGATACGGACGTCTTCGTCCTTAAC
      TCCAGCCCGCGCGGGTGGATGTCGACCCCACTTTTACTATGCCTGCAGAAGCAGGAATTG

AsnThrArgProProLeuGlyAsnTrpPheGlyCysThrTrpMetAsnSerThrGlyPhe
1621  AATACCAGGCCACCGCTGGGCAATTGGTTCGGTTGTACCTGGATGAACTCAACTGGATTC
      TTATGGTCCGGTGGCGACCCGTTAACCAAGCCAACATGGACCTACTTGAGTTGACCTAAG

ThrLysValCysGlyAlaProProCysValIleGlyGlyAlaGlyAsnAsnThrLeuHis
1681  ACCAAAGTGTGCGGAGCGCCTCCTTGTGTCATCGGAGGGGCGGGCAACAACACCCTGCAC
      TGGTTTCACACGCCTCGCGGAGGAACACAGTAGCCTCCCCGCCCGTTGTTGTGGGACGTG

CysProThrAspCysPheArgLysHisProAspAlaThrTyrSerArgCysGlySerGly
1741  TGCCCCACTGATTGCTTCCGCAAGCATCCGGACGCCACATACTCTCGGTGCGGCTCCGGT
      ACGGGGTGACTAACGAAGGCGTTCGTAGGCCTGCGGTGTATGAGAGCCACGCCGAGGCCA

Ile
      ProTrpLeuThrProArgCysLeuValAspTyrProTyrArgLeuTrpHisTyrProCys
1801  CCCTGGATCACACCCAGGTGCCTGGTCGACTACCCGTATAGGCTTTGGCATTATCCTTGT
      GGGACCTAGTGTGGGTCCACGGACCAGCTGATGGGCATATCCGAAACCGTAATAGGAACA

ThrIleAsnTyrThrIlePheLysIleArgMetTyrValGlyGlyValGluHisArgLeu
1861  ACCATCAACTACACCATATTTAAAATCAGGATGTACGTGGGAGGGGTCGAACACAGGCTG
      TGGTAGTTGATGTGGTATAAATTTTAGTCCTACATGCACCCTCCCCAGCTTGTGTCCGAC

GluAlaAlaCysAsnTrpThrArgGlyGluArgCysAspLeuGluAspArgAspArgSer
1921  GAAGCTGCCTGCAACTGGACGCGGGGCGAACGTTGCGATCTGGAAGACAGGGACAGGTCC
      CTTCGACGGACGTTGACCTGCGCCCCGCTTGCAACGCTAGACCTTCTGTCCCTGTCCAGG

GluLeuSerProLeuLeuLeuThrThrThrGlnTrpGlnValLeuProCysSerPheThr
1981  GAGCTCAGCCCGTTACTGCTGACCACTACACAGTGGCAGGTCCTCCCGTGTTCCTTCACA
      CTCGAGTCGGGCAATGACGACTGGTGATGTGTCACCGTCCAGGAGGGCACAAGGAAGTGT

ThrLeuProAlaLeuSerThrGlyLeuIleHisLeuHisGlnAsnIleValAspValGln
2041  ACCCTACCAGCCTTGTCCACCGGCCTCATCCACCTCCACCAGAACATTGTGGACGTGCAG
      TGGGATGGTCGGAACAGGTGGCCGGAGTAGGTGGAGGTGGTCTTGTAACACCTGCACGTC

TyrLeuTyrGlyValGlySerSerIleAlaSerTrpAlaIleLysTrpGluTyrValVal
2101  TACTTGTACGGGGTGGGGTCAAGCATCGCGTCCTGGGCCATTAAGTGGGAGTACGTCGTT
      ATGAACATGCCCCACCCCAGTTCGTAGCGCAGGACCCGGTAATTCACCCTCATGCAGCAA

LeuLeuPheLeuLeuLeuAlaAspAlaArgValCysSerCysLeuTrpMetMetLeuLeu
2161  CTCCTGTTCCTTCTGCTTGCAGACGCGCGCGTCTGCTCCTGCTTGTGGATGATGCTACTC
      GAGGACAAGGAAGACGAACGTCTGCGCGCGCAGACGAGGACGAACACCTACTACGATGAG
```

FIG. 1C

```
           IleSerGlnAlaGluAlaAlaLeuGluAsnLeuValIleLeuAsnAlaAlaSerLeuAla
2221   ATATCCCAAGCGGAGGCGGCTTTGGAGAACCTCGTAATACTTAATGCAGCATCCCTGGCC
       TATAGGGTTCGCCTCCGCCGAAACCTCTTGGAGCATTATGAATTACGTCGTAGGGACCGG

GlyThrHisGlyLeuValSerPheLeuValPhePheCysPheAlaTrpTyrLeuLysGly
2281   GGGACGCACGGTCTTGTATCCTTCCTCGTGTTCTTCTGCTTTGCATGGTATTTGAAGGGT
       CCCTGCGTGCCAGAACATAGGAAGGAGCACAAGAAGACGAAACGTACCATAAACTTCCCA

LysTrpValProGlyAlaValTyrThrPheTyrGlyMetTrpProLeuLeuLeuLeuLeu
2341   AAGTGGGTGCCCGGAGCGGTCTACACCTTCTACGGGATGTGGCCTCTCCTCCTGCTCCTG
       TTCACCCACGGGCCTCGCCAGATGTGGAAGATGCCCTACACCGGAGAGGAGGACGAGGAC

LeuAlaLeuProGlnArgAlaTyrAlaLeuAspThrGluValAlaAlaSerCysGlyGly
2401   TTGGCGTTGCCCCAGCGGGCGTACGCGCTGGACACGGAGGTGGCCGCGTCGTGTGGCGGT
       AACCGCAACGGGGTCGCCCGCATGCGCGACCTGTGCCTCCACCGGCGCAGCACACCGCCA

ValValLeuValGlyLeuMetAlaLeuThrLeuSerProTyrTyrLysArgTyrIleSer
2461   GTTGTTCTCGTCGGGTTGATGGCGCTGACTCTGTCACCATATTACAAGCGCTATATCAGC
       CAACAAGAGCAGCCCAACTACCGCGACTGAGACAGTGGTATAATGTTCGCGATATAGTCG (Asn)
           TrpCysLeuTrpTrpLeuGlnTyrPheLeuThrArgValGluAlaGlnLeuHisValTrp
2521   TGGTGCTTGTGGTGGCTTCAGTATTTTCTGACCAGAGTGGAAGCGCAACTGCACGTGTGG
       ACCACGAACACCACCGAAGTCATAAAAGACTGGTCTCACCTTCGCGTTGACGTGCACACC

IleProProLeuAsnValArgGlyGlyArgAspAlaValIleLeuLeuMetCysAlaVal
2581   ATTCCCCCCCTCAACGTCCGAGGGGGGCGCGACGCCGTCATCTTACTCATGTGTGCTGTA
       TAAGGGGGGGAGTTGCAGGCTCCCCCCGCGCTGCGGCAGTAGAATGAGTACACACGACAT

HisProThrLeuValPheAspIleThrLysLeuLeuLeuAlaValPheGlyProLeuTrp
2641   CACCCGACTCTGGTATTTGACATCACCAAATTGCTGCTGGCCGTCTTCGGACCCCTTTGG
       GTGGGCTGAGACCATAAACTGTAGTGGTTTAACGACGACCGGCAGAAGCCTGGGGAAACC

IleLeuGlnAlaSerLeuLeuLysValProTyrPheValArgValGlnGlyLeuLeuArg
2701   ATTCTTCAAGCCAGTTTGCTTAAAGTACCCTACTTTGTGCGCGTCCAAGGCCTTCTCCGG
       TAAGAAGTTCGGTCAAACGAATTTCATGGGATGAAACACGCGCAGGTTCCGGAAGAGGCC

PheCysAlaLeuAlaArgLysMetIleGlyGlyHisTyrValGlnMetValIleIleLys
2761   TTCTGCGCGTTAGCGCGGAAGATGATCGGAGGCCATTACGTGCAAATGGTCATCATTAAG
       AAGACGCGCAATCGCGCCTTCTACTAGCCTCCGGTAATGCACGTTTACCAGTAGTAATTC

LeuGlyAlaLeuThrGlyThrTyrValTyrAsnHisLeuThrProLeuArgAspTrpAla
2821   TTAGGGGCGCTTACTGGCACCTATGTTTATAACCATCTCACTCCTCTTCGGGACTGGGCG
       AATCCCCGCGAATGACCGTGGATACAAATATTGGTAGAGTGAGGAGAAGCCCTGACCCGC

HisAsnGlyLeuArgAspLeuAlaValAlaValGluProValValPheSerGlnMetGlu
2881   CACAACGGCTTGCGAGATCTGGCCGTGGCTGTAGAGCCAGTCGTCTTCTCCCAAATGGAG
       GTGTTGCCGAACGCTCTAGACCGGCACCGACATCTCGGTCAGCAGAAGAGGGTTTACCTC

ThrLysLeuIleThrTrpGlyAlaAspThrAlaAlaCysGlyAspIleIleAsnGlyLeu
2941   ACCAAGCTCATCACGTGGGGGGCAGATACCGCCGCGTGCGGTGACATCATCAACGGCTTG
       TGGTTCGAGTAGTGCACCCCCCGTCTATGGCGGCGCACGCCACTGTAGTAGTTGCCGAAC
```

FIG. 1D

```
            ProValSerAlaArgArgGlyArgGluIleLeuLeuGlyProAlaAspGlyMetValSer
3001    CCTGTTTCCGCCCGCAGGGGCCGGGAGATACTGCTCGGGCCAGCCGATGGAATGGTCTCC
        GGACAAAGGCGGGCGTCCCCGGCCCTCTATGACGAGCCCGGTCGGCTACCTTACCAGAGG

LysGlyTrpArgLeuLeuAlaProIleThrAlaTyrAlaGlnGlnThrArgGlyLeuLeu
3061    AAGGGGTGGAGGTTGCTGGCGCCCATCACGGCGTACGCCCAGCAGACAAGGGGCCTCCTA
        TTCCCCACCTCCAACGACCGCGGGTAGTGCCGCATGCGGGTCGTCTGTTCCCCGGAGGAT

GlyCysIleIleThrSerLeuThrGlyArgAspLysAsnGlnValGluGlyGluValGln
3121    GGGTGCATAATCACCAGCCTAACTGGCCGGGACAAAAACCAAGTGGAGGGTGAGGTCCAG
        CCCACGTATTAGTGGTCGGATTGACCGGCCCTGTTTTTGGTTCACCTCCCACTCCAGGTC

IleValSerThrAlaAlaGlnThrPheLeuAlaThrCysIleAsnGlyValCysTrpThr
3181    ATTGTGTCAACTGCTGCCCAAACCTTCCTGGCAACGTGCATCAATGGGGTGTGCTGGACT
        TAACACAGTTGACGACGGGTTTGGAAGGACCGTTGCACGTAGTTACCCCACACGACCTGA

ValTyrHisGlyAlaGlyThrArgThrIleAlaSerProLysGlyProValIleGlnMet
3241    GTCTACCACGGGGCCGGAACGAGGACCATCGCGTCACCCAAGGGTCCTGTCATCCAGATG
        CAGATGGTGCCCCGGCCTTGCTCCTGGTAGCGCAGTGGGTTCCCAGGACAGTAGGTCTAC

Ser     Thr
            TyrThrAsnValAspGlnAspLeuValGlyTrpProAlaProGlnGlySerArgSerLeu
3301    TATACCAATGTAGACCAAGACCTTGTGGGCTGGCCCGCTCCGCAAGGTAGCCGCTCATTG
        ATATGGTTACATCTGGTTCTGGAACACCCGACCGGGCGAGGCGTTCCATCGGCGAGTAAC

ThrProCysThrCysGlySerSerAspLeuTyrLeuValThrArgHisAlaAspValIle
3361    ACACCCTGCACTTGCGGCTCCTCGGACCTTTACCTGGTCACGAGGCACGCCGATGTCATT
        TGTGGGACGTGAACGCCGAGGAGCCTGGAAATGGACCAGTGCTCCGTGCGGCTACAGTAA

ProValArgArgArgGlyAspSerArgGlySerLeuLeuSerProArgProIleSerTyr
3421    CCCGTGCGCCGGCGGGTGATAGCAGGGGCAGCCTGCTGTCGCCCCGGCCCATTTCCTAC
        GGGCACGCGGCCGCCCCACTATCGTCCCCGTCGGACGACAGCGGGGCCGGGTAAAGGATG

LeuLysGlySerSerGlyGlyProLeuLeuCysProAlaGlyHisAlaValGlyIlePhe
3481    TTGAAAGGCTCCTCGGGGGGTCCGCTGTTGTGCCCCGCGGGGCACGCCGTGGGCATATTT
        AACTTTCCGAGGAGCCCCCCAGGCGACAACACGGGGCGCCCCGTGCGGCACCCGTATAAA

ArgAlaAlaValCysThrArgGlyValAlaLysAlaValAspPheIleProValGluAsn
3541    AGGGCCGCGGTGTGCACCCGTGGAGTGGCTAAGGCGGTGGACTTTATCCCTGTGGAGAAC
        TCCCGGCGCCACACGTGGGCACCTCACCGATTCCGCCACCTGAAATAGGGACACCTCTTG

LeuGluThrThrMetArgSerProValPheThrAspAsnSerSerProProValValPro
3601    CTAGAGACAACCATGAGGTCCCCGGTGTTCACGGATAACTCCTCTCCACCAGTAGTGCCC
        GATCTCTGTTGGTACTCCAGGGGCCACAAGTGCCTATTGAGGAGAGGTGGTCATCACGGG

GlnSerPheGlnValAlaHisLeuHisAlaProThrGlySerGlyLysSerThrLysVal
3661    CAGAGCTTCCAGGTGGCTCACCTCCATGCTCCCACAGGCAGCGGCAAAAGCACCAAGGTC
        GTCTCGAAGGTCCACCGAGTGGAGGTACGAGGGTGTCCGTCGCCGTTTTCGTGGTTCCAG

ProAlaAlaTyrAlaAlaGlnGlyTyrLysValLeuValLeuAsnProSerValAlaAla
3721    CCGGCTGCATATGCAGCTCAGGGCTATAAGGTGCTAGTACTCAACCCCTCTGTTGCTGCA
        GGCCGACGTATACGTCGAGTCCCGATATTCCACGATCATGAGTTGGGGAGACAACGACGT
```

FIG. 1E

```
                                                                  Leu
        ThrLeuGlyPheGlyAlaTyrMetSerLysAlaHisGlyIleAspProAsnIleArgThr
3781    ACACTGGGCTTTGGTGCTTACATGTCCAAGGCTCATGGGATCGATCCTAACATCAGGACC
        TGTGACCCGAAACCACGAATGTACAGGTTCCGAGTACCCTAGCTAGGATTGTAGTCCTGG

GlyValArgThrIleThrThrGlySerProIleThrTyrSerThrTyrGlyLysPheLeu
3841    GGGGTGAGAACAATTACCACTGGCAGCCCCATCACGTACTCCACCTACGGCAAGTTCCTT
        CCCCACTCTTGTTAATGGTGACCGTCGGGGTAGTGCATGAGGTGGATGCCGTTCAAGGAA

AlaAspGlyGlyCysSerGlyGlyAlaTyrAspIleIleIleCysAspGluCysHisSer
3901    GCCGACGGCGGGTGCTCGGGGGGCGCTTATGACATAATAATTTGTGACGAGTGCCACTCC
        CGGCTGCCGCCCACGAGCCCCCCGCGAATACTGTATTATTAAACACTGCTCACGGTGAGG (Val)
        ThrAspAlaThrSerIleLeuGlyIleGlyThrValLeuAspGlnAlaGluThrAlaGly
3961    ACGGATGCCACATCCATCTTGGGCATCGGCACTGTCCTTGACCAAGCAGAGACTGCGGGG
        TGCCTACGGTGTAGGTAGAACCCGTAGCCGTGACAGGAACTGGTTCGTCTCTGACGCCCC

AlaArgLeuValValLeuAlaThrAlaThrProProGlySerValThrValProHisPro
4021    GCGAGACTGGTTGTGCTCGCCACCGCCACCCCTCCGGGCTCCGTCACTGTGCCCCATCCC
        CGCTCTGACCAACACGAGCGGTGGCGGTGGGGAGGCCCGAGGCAGTGACACGGGGTAGGG

AsnIleGluGluValAlaLeuSerThrThrGlyGluIleProPheTyrGlyLysAlaIle
4081    AACATCGAGGAGGTTGCTCTGTCCACCACCGGAGAGATCCCTTTTTACGGCAAGGCTATC
        TTGTAGCTCCTCCAACGAGACAGGTGGTGGCCTCTCTAGGGAAAAATGCCGTTCCGATAG

ProLeuGluValIleLysGlyGlyArgHisLeuIlePheCysHisSerLysLysLysCys
4141    CCCCTCGAAGTAATCAAGGGGGGGAGACATCTCATCTTCTGTCATTCAAAGAAGAAGTGC
        GGGGAGCTTCATTAGTTCCCCCCCTCTGTAGAGTAGAAGACAGTAAGTTTCTTCTTCACG

AspGluLeuAlaAlaLysLeuValAlaLeuGlyIleAsnAlaValAlaTyrTyrArgGly
4201    GACGAACTCGCCGCAAAGCTGGTCGCATTGGGCATCAATGCCGTGGCCTACTACCGCGGT
        CTGCTTGAGCGGCGTTTCGACCAGCGTAACCCGTAGTTACGGCACCGGATGATGGCGCCA

LeuAspValSerValIleProThrSerGlyAspValValValValAlaThrAspAlaLeu
4261    CTTGACGTGTCCGTCATCCCGACCAGCGGCGATGTTGTCGTCGTGGCAACCGATGCCCTC
        GAACTGCACAGGCAGTAGGGCTGGTCGCCGCTACAACAGCAGCACCGTTGGCTACGGGAG

Tyr
        MetThrGlyTyrThrGlyAspPheAspSerValIleAspCysAsnThrCysValThrGln
4321    ATGACCGGCTATACCGGCGACTTCGACTCGGTGATAGACTGCAATACGTGTGTCACCCAG
        TACTGGCCGATATGGCCGCTGAAGCTGAGCCACTATCTGACGTTATGCACACAGTGGGTC (Ser)
        ThrValAspPheSerLeuAspProThrPheThrIleGluThrIleThrLeuProGlnAsp
4381    ACAGTCGATTTCAGCCTTGACCCTACCTTCACCATTGAGACAATCACGCTCCCCCAGGAT
        TGTCAGCTAAAGTCGGAACTGGGATGGAAGTGGTAACTCTGTTAGTGCGAGGGGGTCCTA

AlaValSerArgThrGlnArgArgGlyArgThrGlyArgGlyLysProGlyIleTyrArg
4441    GCTGTCTCCCGCACTCAACGTCGGGGCAGGACTGGCAGGGGGAAGCCAGGCATCTACAGA
        CGACAGAGGGCGTGAGTTGCAGCCCCGTCCTGACCGTCCCCCTTCGGTCCGTAGATGTCT

PheValAlaProGlyGluArgProSerGlyMetPheAspSerSerValLeuCysGluCys
4501    TTTGTGGCACCGGGGGAGCGCCCCTCCGGCATGTTCGACTCGTCCGTCCTCTGTGAGTGC
        AAACACCGTGGCCCCCTCGCGGGGAGGCCGTACAAGCTGAGCAGGCAGGAGACACTCACG
```

FIG. 1F

```
         TyrAspAlaGlyCysAlaTrpTyrGluLeuThrProAlaGluThrThrValArgLeuArg
4561     TATGACGCAGGCTGTGCTTGGTATGAGCTCACGCCCGCCGAGACTACAGTTAGGCTACGA
         ATACTGCGTCCGACACGAACCATACTCGAGTGCGGGCGGCTCTGATGTCAATCCGATGCT

AlaTyrMetAsnThrProGlyLeuProValCysGlnAspHisLeuGluPheTrpGluGly
4621     GCGTACATGAACACCCCGGGGCTTCCCGTGTGCCAGGACCATCTTGAATTTTGGGAGGGC
         CGCATGTACTTGTGGGGCCCCGAAGGGCACACGGTCCTGGTAGAACTTAAAACCCTCCCG

ValPheThrGlyLeuThrHisIleAspAlaHisPheLeuSerGlnThrLysGlnSerGly
4681     GTCTTTACAGGCCTCACTCATATAGATGCCCACTTTCTATCCCAGACAAAGCAGAGTGGG
         CAGAAATGTCCGGAGTGAGTATATCTACGGGTGAAAGATAGGGTCTGTTTCGTCTCACCC

GluAsnLeuProTyrLeuValAlaTyrGlnAlaThrValCysAlaArgAlaGlnAlaPro
4741     GAGAACCTTCCTTACCTGGTAGCGTACCAAGCCACCGTGTGCGCTAGGGCTCAAGCCCCT
         CTCTTGGAAGGAATGGACCATCGCATGGTTCGGTGGCACACGCGATCCCGAGTTCGGGGA

ProProSerTrpAspGlnMetTrpLysCysLeuIleArgLeuLysProThrLeuHisGly
4801     CCCCCATCGTGGGACCAGATGTGGAAGTGTTTGATTCGCCTCAAGCCCACCCTCCATGGG
         GGGGGTAGCACCCTGGTCTACACCTTCACAAACTAAGCGGAGTTCGGGTGGGAGGTACCC

ProThrProLeuLeuTyrArgLeuGlyAlaValGlnAsnGluIleThrLeuThrHisPro
4861     CCAACACCCCTGCTATACAGACTGGGCGCTGTTCAGAATGAAATCACCCTGACGCACCCA
         GGTTGTGGGGACGATATGTCTGACCCGCGACAAGTCTTACTTTAGTGGGACTGCGTGGGT

ValThrLysTyrIleMetThrCysMetSerAlaAspLeuGluValValThrSerThrTrp
4921     GTCACCAAATACATCATGACATGCATGTCGGCCGACCTGGAGGTCGTCACGAGCACCTGG
         CAGTGGTTTATGTAGTACTGTACGTACAGCCGGCTGGACCTCCAGCAGTGCTCGTGGACC

ValLeuValGlyGlyValLeuAlaAlaLeuAlaAlaTyrCysLeuSerThrGlyCysVal
4981     GTGCTCGTTGGCGGCGTCCTGGCTGCTTTGGCCGCGTATTGCCTGTCAACAGGCTGCGTG
         CACGAGCAACCGCCGCAGGACCGACGAAACCGGCGCATAACGGACAGTTGTCCGACGCAC

ValIleValGlyArgValValLeuSerGlyLysProAlaIleIleProAspArgGluVal
5041     GTCATAGTGGGCAGGGTCGTCTTGTCCGGGAAGCCGGCAATCATACCTGACAGGGAAGTC
         CAGTATCACCCGTCCCAGCAGAACAGGCCCTTCGGCCGTTAGTATGGACTGTCCCTTCAG

LeuTyrArgGluPheAspGluMetGluGluCysSerGlnHisLeuProTyrIleGluGln
5101     CTCTACCGAGAGTTCGATGAGATGGAAGAGTGCTCTCAGCACTTACCGTACATCGAGCAA
         GAGATGGCTCTCAAGCTACTCTACCTTCTCACGAGAGTCGTGAATGGCATGTAGCTCGTT

GlyMetMetLeuAlaGluGlnPheLysGlnLysAlaLeuGlyLeuLeuGlnThrAlaSer
5161     GGGATGATGCTCGCCGAGCAGTTCAAGCAGAAGGCCCTCGGCCTCCTGCAGACCGCGTCC
         CCCTACTACGAGCGGCTCGTCAAGTTCGTCTTCCGGGAGCCGGAGGACGTCTGGCGCAGG

ArgGlnAlaGluValIleAlaProAlaValGlnThrAsnTrpGlnLysLeuGluThrPhe
5221     CGTCAGGCAGAGGTTATCGCCCCTGCTGTCCAGACCAACTGGCAAAAACTCGAGACCTTC
         GCAGTCCGTCTCCAATAGCGGGGACGACAGGTCTGGTTGACCGTTTTTGAGCTCTGGAAG

TrpAlaLysHisMetTrpAsnPheIleSerGlyIleGlnTyrLeuAlaGlyLeuSerThr
5281     TGGGCGAAGCATATGTGGAACTTCATCAGTGGGATACAATACTTGGCGGGCTTGTCAACG
         ACCCGCTTCGTATACACCTTGAAGTAGTCACCCTATGTTATGAACCGCCCGAACAGTTGC

LeuProGlyAsnProAlaIleAlaSerLeuMetAlaPheThrAlaAlaValThrSerPro
5341     CTGCCTGGTAACCCCGCCATTGCTTCATTGATGGCTTTTACAGCTGCTGTCACCAGCCCA
         GACGGACCATTGGGGCGGTAACGAAGTAACTACCGAAAATGTCGACGACAGTGGTCGGGT

LeuThrThrSerGlnThrLeuLeuPheAsnIleLeuGlyGlyTrpValAlaAlaGlnLeu
5401     CTAACCACTAGCCAAACCCTCCTCTTCAACATATTGGGGGGTGGGTGGCTGCCCAGCTC
         GATTGGTGATCGGTTTGGGAGGAGAAGTTGTATAACCCCCCCACCCACCGACGGGTCGAG
```

FIG. 1G

```
                AlaAlaProGlyAlaAlaThrAlaPheValGlyAlaGlyLeuAlaGlyAlaAlaIleGly
       5461     GCCGCCCCCGGTGCCGCTACTGCCTTTGTGGGCGCTGGCTTAGCTGGCGCCGCCATCGGC
                CGGCGGGGGCCACGGCGATGACGGAAACACCCGCGACCGAATCGACCGCGGCGGTAGCCG

SerValGlyLeuGlyLysValLeuIleAspIleLeuAlaGlyTyrGlyAlaGlyValAla
       5521     AGTGTTGGACTGGGGAAGGTCCTCATAGACATCCTTGCAGGGTATGGCGCGGGCGTGGCG
                TCACAACCTGACCCCTTCCAGGAGTATCTGTAGGAACGTCCCATACCGCGCCCGCACCGC (Gly)
                GlyAlaLeuValAlaPheLysIleMetSerGlyGluValProSerThrGluAspLeuVal
       5581     GGAGCTCTTGTGGCATTCAAGATCATGAGCGGTGAGGTCCCCTCCACGGAGGACCTGGTC
                CCTCGAGAACACCGTAAGTTCTAGTACTCGCCACTCCAGGGGAGGTGCCTCCTGGACCAG

AsnLeuLeuProAlaIleLeuSerProGlyAlaLeuValValGlyValValCysAlaAla
       5641     AATCTACTGCCCGCCATCCTCTCGCCCGGAGCCCTCGTAGTCGGCGTGGTCTGTGCAGCA
                TTAGATGACGGGCGGTAGGAGAGCGGGCCTCGGGAGCATCAGCCGCACCAGACACGTCGT

IleLeuArgArgHisValGlyProGlyGluGlyAlaValGlnTrpMetAsnArgLeuIle
       5701     ATACTGCGCCGGCACGTTGGCCCGGGCGAGGGGGCAGTGCAGTGGATGAACCGGCTGATA
                TATGACGCGGCCGTGCAACCGGGCCCGCTCCCCCGTCACGTCACCTACTTGGCCGACTAT

AlaPheAlaSerArgGlyAsnHisValSerProThrHisTyrValProGluSerAspAla
       5761     GCCTTCGCCCTCCGGGGGAACCATGTTTCCCCCACGCACTACGTGCCGGAGAGCGATGCA
                CGGAAGCGGAGGGCCCCCTTGGTACAAAGGGGGTGCGTGATGCACGGCCTCTCGCTACGT (HisCys)
                AlaAlaArgValThrAlaIleLeuSerSerLeuThrValThrGlnLeuLeuArgArgLeu
       5821     GCTGCCCGCGTCACTGCCATACTCAGCAGCCTCACTGTAACCCAGCTCCTGAGGCGACTG
                CGACGGGCGCAGTGACGGTATGAGTCGTCGGAGTGACATTGGGTCGAGGACTCCGCTGAC

HisGlnTrpIleSerSerGluCysThrThrProCysSerGlySerTrpLeuArgAspIle
       5881     CACCAGTGGATAAGCTCGGAGTGTACCACTCCATGCTCCGGTTCCTGGCTAAGGGACATC
                GTGGTCACCTATTCGAGCCTCACATGGTGAGGTACGAGGCCAAGGACCGATTCCCTGTAG

TrpAspTrpIleCysGluValLeuSerAspPheLysThrTrpLeuLysAlaLysLeuMet
       5941     TGGGACTGGATATGCGAGGTGTTGAGCGACTTTAAGACCTGGCTAAAAGCTAAGCTCATG
                ACCCTGACCTATACGCTCCACAACTCGCTGAAATTCTGGACCGATTTTCGATTCGAGTAC

ProGlnLeuProGlyIleProPheValSerCysGlnArgGlyTyrLysGlyValTrpArg
       6001     CCACAGCTGCCTGGGATCCCCTTTGTGTCCTGCCAGCGCGGGTATAAGGGGGTCTGGCGA
                GGTGTCGACGGACCCTAGGGGAAACACAGGACGGTCGCGCCCATATTCCCCCAGACCGCT (Val)
                GlyAspGlyIleMetHisThrArgCysHisCysGlyAlaGluIleThrGlyHisValLys
       6061     GTGGACGGCATCATGCACACTCGCTGCCACTGTGGAGCTGAGATCACTGGACATGTCAAA
                CACCTGCCGTAGTACGTGTGAGCGACGGTGACACCTCGACTCTAGTGACCTGTACAGTTT

AsnGlyThrMetArgIleValGlyProArgThrCysArgAsnMetTrpSerGlyThrPhe
       6121     AACGGGACGATGAGGATCGTCGGTCCTAGGACCTGCAGGAACATGTGGAGTGGGACCTTC
                TTGCCCTGCTACTCCTAGCAGCCAGGATCCTGGACGTCCTTGTACACCTCACCCTGGAAG

ProIleAsnAlaTyrThrThrGlyProCysThrProLeuProAlaProAsnTyrThrPhe
       6181     CCCATTAATGCCTACACCACGGGCCCCTGTACCCCCCTTCCTGCGCCGAACTACACGTTC
                GGGTAATTACGGATGTGGTGCCCGGGGACATGGGGGGAAGGACGCGGCTTGATGTGCAAG
```

FIG. 1H

```
             AlaLeuTrpArgValSerAlaGluGluTyrValGluIleArgGlnValGlyAspPheHis
      6241   GCGCTATGGAGGGTGTCTGCAGAGGAATATGTGGAGATAAGGCAGGTGGGGGACTTCCAC
             CGCGATACCTCCCACAGACGTCTCCTTATACACCTCTATTCCGTCCACCCCCTGAAGGTG

TyrValThrGlyMetThrThrAspAsnLeuLysCysProCysGlnValProSerProGlu
      6301   TACGTGACGGGTATGACTACTGACAATCTCAAATGCCCGTGCCAGGTCCCATCGCCCGAA
             ATGCACTGCCCATACTGATGACTGTTAGAGTTTACGGGCACGGTCCAGGGTAGCGGGCTT

PhePheThrGluLeuAspGlyValArgLeuHisArgPheAlaProProCysLysProLeu
      6361   TTTTTCACAGAATTGGACGGGGTGCGCCTACATAGGTTTGCGCCCCCTGCAAGCCCTTG
             AAAAAGTGTCTTAACCTGCCCCACGCGGATGTATCCAAACGCGGGGGACGTTCGGGAAC

LeuArgGluGluValSerPheArgValGlyLeuHisGluTyrProValGlySerGlnLeu
      6421   CTGCGGGAGGAGGTATCATTCAGAGTAGGACTCCACGAATACCCGGTAGGGTCGCAATTA
             GACGCCCTCCTCCATAGTAAGTCTCATCCTGAGGTGCTTATGGGCCATCCCAGCGTTAAT

ProCysGluProGluProAspValAlaValLeuThrSerMetLeuThrAspProSerHis
      6481   CCTTGCGAGCCCGAACCGGACGTGGCCGTGTTGACGTCCATGCTCACTGATCCCTCCCAT
             GGAACGCTCGGGCTTGGCCTGCACCGGCACAACTGCAGGTACGAGTGACTAGGGAGGGTA

IleThrAlaGluAlaAlaGlyArgArgLeuAlaArgGlySerProProSerValAlaSer
      6541   ATAACAGCAGAGGCGGCCGGGCGAAGGTTGGCGAGGGGATCACCCCCCTCTGTGGCCAGC
             TATTGTCGTCTCCGCCGGCCCGCTTCCAACCGCTCCCCTAGTGGGGGGAGACACCGGTCG

SerSerAlaSerGlnLeuSerAlaProSerLeuLysAlaThrCysThrAlaAsnHisAsp
      6601   TCCTCGGCTAGCCAGCTATCCGCTCCATCTCTCAAGGCAACTTGCACCGCTAACCATGAC
             AGGAGCCGATCGGTCGATAGGCGAGGTAGAGAGTTCCGTTGAACGTGGCGATTGGTACTG

SerProAspAlaGluLeuIleGluAlaAsnLeuLeuTrpArgGlnGluMetGlyGlyAsn
      6661   TCCCCTGATGCTGAGCTCATAGAGGCCAACCTCCTATGGAGGCAGGAGATGGGCGGCAAC
             AGGGGACTACGACTCGAGTATCTCCGGTTGGAGGATACCTCCGTCCTCTACCCGCCGTTG

IleThrArgValGluSerGluAsnLysValValIleLeuAspSerPheAspProLeuVal
      6721   ATCACCAGGGTTGAGTCAGAAAACAAAGTGGTGATTCTGGACTCCTTCGATCCGCTTGTG
             TAGTGGTCCCAACTCAGTCTTTTGTTTCACCACTAAGACCTGAGGAAGCTAGGCGAACAC

AlaGluGluAspGluArgGluIleSerValProAlaGluIleLeuArgLysSerArgArg
      6781   GCGGAGGAGGACGAGCGGGAGATCTCCGTACCCGCAGAAATCCTGCGGAAGTCTCGGAGA
             CGCCTCCTCCTGCTCGCCCTCTAGAGGCATGGGCGTCTTTAGGACGCCTTCAGAGCCTCT

PheAlaGlnAlaLeuProValTrpAlaArgProAspTyrAsnProProLeuValGluThr
      6841   TTCGCCCAGGCCCTGCCCGTTTGGGCGCGGCCGGACTATAACCCCCCGCTAGTGGAGACG
             AAGCGGGTCCGGGACGGGCAAACCCGCGCCGGCCTGATATTGGGGGCGATCACCTCTGC

TrpLysLysProAspTyrGluProProValValHisGlyCysProLeuProProProLys
      6901   TGGAAAAAGCCCGACTACGAACCACCTGTGGTCCATGGCTGTCCGCTTCCACCTCCAAAG
             ACCTTTTTCGGGCTGATGCTTGGTGGACACCAGGTACCGACAGGCGAAGGTGGAGGTTTC

SerProProValProProProArgLysLysArgThrValValLeuThrGluSerThrLeu
      6961   TCCCCTCCTGTGCCTCCGCCTCGGAAGAAGCGGACGGTGGTCCTCACTGAATCAACCCTA
             AGGGGAGGACACGGAGGCGGAGCCTTCTTCGCCTGCCACCAGGAGTGACTTAGTTGGGAT (Ser)
             SerThrAlaLeuAlaGluLeuAlaThrArgSerPheGlySerSerSerThrSerGlyIle
      7021   TCTACTGCCTTGGCCGAGCTCGCCACCAGAAGCTTTGGCAGCTCCTCAACTTCCGGCATT
             AGATGACGGAACCGGCTCGAGCGGTGGTCTTCGAAACCGTCGAGGAGTTGAAGGCCGTAA
```

FIG. 1I

```
         ThrGlyAspAsnThrThrThrSerSerGluProAlaProSerGlyCysProProAspSer
7081     ACGGGCGACAATACGACAACATCCTCTGAGCCCGCCCCTTCTGGCTGCCCCCCGACTCC
         TGCCCGCTGTTATGCTGTTGTAGGAGACTCGGGCGGGGAAGACCGACGGGGGGCTGAGG (PheAla)
         AspAlaGluSerTyrSerSerMetProProLeuGluGlyGluProGlyAspProAspLeu
7141     GACGCTGAGTCCTATTCCTCCATGCCCCCCCTGGAGGGGGAGCCTGGGGATCCGGATCTT
         CTGCGACTCAGGATAAGGAGGTACGGGGGGGACCTCCCCCTCGGACCCCTAGGCCTAGAA

SerAspGlySerTrpSerThrValSerSerGluAlaAsnAlaGluAspValValCysCys
7201     AGCGACGGGTCATGGTCAACGGTCAGTAGTGAGGCCAACGCGGAGGATGTCGTGTGCTGC
         TCGCTGCCCAGTACCAGTTGCCAGTCATCACTCCGGTTGCGCCTCCTACAGCACACGACG

SerMetSerTyrSerTrpThrGlyAlaLeuValThrProCysAlaAlaGluGLuGlnLys
7261     TCAATGTCTTACTCTTGGACAGGCGCACTCGTCACCCCGTGCGCCGCGGAAGAACAGAAA
         AGTTACAGAATGAGAACCTGTCCGCGTGAGCAGTGGGGCACGCGGCGCCTTCTTGTCTTT

LeuProIleAsnAlaLeuSerAsnSerLeuLeuArgHisHisAsnLeuValTyrSerThr
7321     CTGCCCATCAATGCACTAAGCAACTCGTTGCTACGTCACCACAATTTGGTGTATTCCACC
         GACGGGTAGTTACGTGATTCGTTGAGCAACGATGCAGTGGTGTTAAACCACATAAGGTGG

ThrSerArgSerAlaCysGlnArgGlnLysLysValThrPheAspArgLeuGlnValLeu
7381     ACCTCACGCAGTGCTTGCCAAAGGCAGAAGAAAGTCACATTTGACAGACTGCAAGTTCTG
         TGGAGTGCGTCACGAACGGTTTCCGTCTTCTTTCAGTGTAAACTGTCTGACGTTCAAGAC

AspSerHisTyrGlnAspValLeuLysGluValLysAlaAlaAlaSerLysValLysAla
7441     GACAGCCATTACCAGGACGTACTCAAGGAGGTTAAAGCAGCGGCGTCAAAAGTGAAGGCT
         CTGTCGGTAATGGTCCTGCATGAGTTCCTCCAATTTCGTCGCCGCAGTTTTCACTTCCGA (Phe)
         AsnLeuLeuSerValGluGluAlaCysSerLeuThrProProHisSerAlaLysSerLys
7501     AACTTGCTATCCGTAGAGGAAGCTTGCAGCCTGACGCCCCCACACTCAGCCAAATCCAAG
         TTGAACGATAGGCATCTCCTTCGAACGTCGGACTGCGGGGGTGTGAGTCGGTTTAGGTTC

PheGlyTyrGlyAlaLysAspValArgCysHisAlaArgLysAlaValThrHisIleAsn
7561     TTTGGTTATGGGGCAAAAGACGTCCGTTGCCATGCCAGAAAGGCCGTAACCCACATCAAC
         AAACCAATACCCCGTTTTCTGCAGGCAACGGTACGGTCTTTCCGGCATTGGGTGTAGTTG

SerValTrpLysAspLeuLeuGluAspAsnValThrProIleAspThrThrIleMetAla
7621     TCCGTGTGGAAAGACCTTCTGGAAGACAATGTAACACCAATAGACACTACCATCATGGCT
         AGGCACACCTTTCTGGAAGACCTTCTGTTACATTGTGGTTATCTGTGATGGTAGTACCGA

LysAsnGluValPheCysValGlnProGluLysGlyGlyArgLysProAlaArgLeuIle
7681     AAGAACGAGGTTTTCTGCGTTCAGCCTGAGAAGGGGGGTCGTAAGCCAGCTCGTCTCATC
         TTCTTGCTCCAAAAGACGCAAGTCGGACTCTTCCCCCCAGCATTCGGTCGAGCAGAGTAG

ValPheProAspLeuGlyValArgValCysGluLysMetAlaLeuTyrAspValValThr
7741     GTGTTCCCCGATCTGGGCGTGCGCGTGTGCGAAAAGATGGCTTTGTACGACGTGGTTACA
         CACAAGGGGCTAGACCCGCACGCGCACACGCTTTTCTACCGAAACATGCTGCACCAATGT

LysLeuProLeuAlaValMetGlySerSerTyrGlyPheGlnTyrSerProGlyGlnArg
7801     AAGCTCCCCTTGGCCGTGATGGGAAGCTCCTACGGATTCCAATACTCACCAGGACAGCGG
         TTCGAGGGGAACCGGCACTACCCTTCGAGGATGCCTAAGGTTATGAGTGGTCCTGTCGCC

ValGluPheLeuValGlnAlaTrpLysSerLysLysThrProMetGlyPheSerTyrAsp
7861     GTTGAATTCCTCGTGCAAGCGTGGAAGTCCAAGAAAACCCCAATGGGGTTCTCGTATGAT
         CAACTTAAGGAGCACGTTCGCACCTTCAGGTTCTTTTGGGGTTACCCCAAGAGCATACTA
```

FIG. 1J

```
         ThrArgCysPheAspSerThrValThrGluSerAspIleArgThrGluGluAlaIleTyr
7921   ACCCGCTGCTTTGACTCCACAGTCACTGAGAGCGACATCCGTACGGAGGAGGCAATCTAC
       TGGGCGACGAAACTGAGGTGTCAGTGACTCTCGCTGTAGGCATGCCTCCTCCGTTAGATG

GlnCysCysAspLeuAspProGlnAlaArgValAlaIleLysSerLeuThrGluArgLeu
7981   CAATGTTGTGACCTCGACCCCCAAGCCCGCGTGGCCATCAAGTCCCTCACCGAGAGGCTT
       GTTACAACACTGGAGCTGGGGGTTCGGGCGCACCGGTAGTTCAGGGAGTGGCTCTCCGAA (Gly)
         TyrValGlyGlyProLeuThrAsnSerArgGlyGluAsnCysGlyTyrArgArgCysArg
8041   TATGTTGGGGGCCCTCTTACCAATTCAAGGGGGGAGAACTGCGGCTATCGCAGGTGCCGC
       ATACAACCCCGGGAGAATGGTTAAGTTCCCCCCTCTTGACGCCGATAGCGTCCACGGCG

AlaSerGlyValLeuThrThrSerCysGlyAsnThrLeuThrCysTyrIleLysAlaArg
8101   GCGAGCGGCGTACTGACAACTAGCTGTGGTAACACCCTCACTTGCTACATCAAGGCCCGG
       CGCTCGCCGCATGACTGTTGATCGACACCATTGTGGGAGTGAACGATGTAGTTCCGGGCC

AlaAlaCysArgAlaAlaGlyLeuGlnAspCysThrMetLeuValCysGlyAspAspLeu
8161   GCAGCCTGTCGAGCCGCAGGGCTCCAGGACTGCACCATGCTCGTGTGTGGCGACGACTTA
       CGTCGGACAGCTCGGCGTCCCGAGGTCCTGACGTGGTACGAGCACACACCGCTGCTGAAT

ValValIleCysGluSerAlaGlyValGlnGluAspAlaAlaSerLeuArgAlaPheThr
8221   GTCGTTATCTGTGAAAGCGCGGGGGTCCAGGAGGACGCGGCGAGCCTGAGAGCCTTCACG
       CAGCAATAGACACTTTCGCGCCCCCAGGTCCTCCTGCGCCGCTCGGACTCTCGGAAGTGC

GluAlaMetThrArgTyrSerAlaProProGlyAspProProGlnProGluTyrAspLeu
8281   GAGGCTATGACCAGGTACTCCGCCCCCCCTGGGGACCCCCCACAACCAGAATACGACTTG
       CTCCGATACTGGTCCATGAGGCGGGGGGGACCCCTGGGGGGTGTTGGTCTTATGCTGAAC

GluLeuIleThrSerCysSerSerAsnValSerValAlaHisAspGlyAlaGlyLysArg
8341   GAGCTCATAACATCATGCTCCTCCAACGTGTCAGTCGCCCACGACGGCGCTGGAAAGAGG
       CTCGAGTATTGTAGTACGAGGAGGTTGCACAGTCAGCGGGTGCTGCCGCGACCTTTCTCC

ValTyrTyrLeuThrArgAspProThrThrProLeuAlaArgAlaAlaTrpGluThrAla
8401   GTCTACTACCTCACCCGTGACCCTACAACCCCCCTCGCGAGAGCTGCGTGGGAGACAGCA
       CAGATGATGGAGTGGGCACTGGGATGTTGGGGGGAGCGCTCTCGACGCACCCTCTGTCGT

ArgHisThrProValAsnSerTrpLeuGlyAsnIleIleMetPheAlaProThrLeuTrp
8461   AGACACACTCCAGTCAATTCCTGGCTAGGCAACATAATCATGTTTGCCCCCACACTGTGG
       TCTGTGTGAGGTCAGTTAAGGACCGATCCGTTGTATTAGTACAAACGGGGGTGTGACACC

AlaArgMetIleLeuMetThrHisPhePheSerValLeuIleAlaArgAspGlnLeuGlu
8521   GCGAGGATGATACTGATGACCCATTTCTTTAGCGTCCTTATAGCCAGGGACCAGCTTGAA
       CGCTCCTACTATGACTACTGGGTAAAGAAATCGCAGGAATATCGGTCCCTGGTCGAACTT

GlnAlaLeuAspCysGluIleTyrGlyAlaCysTyrSerIleGluProLeuAspLeuPro
8581   CAGGCCCTCGATTGCGAGATCTACGGGGCCTGCTACTCCATAGAACCACTTGATCTACCT
       GTCCGGGAGCTAACGCTCTAGATGCCCCGGACGATGAGGTATCTTGGTGAACTAGATGGA

ProIleIleGlnArgLeuHisGlyLeuSerAlaPheSerLeuHisSerTyrSerProGly
8641   CCAATCATTCAAAGACTCCATGGCCTCAGCGCATTTTCACTCCACAGTTACTCTCCAGGT
       GGTTAGTAAGTTTCTGAGGTACCGGAGTCGCGTAAAAGTGAGGTGTCAATGAGAGGTCCA
```

FIG. 1K

```
      GluIleAsnArgValAlaAlaCysLeuArgLysLeuGlyValProProLeuArgAlaTrp
8701  GAAATTAATAGGGTGGCCGCATGCCTCAGAAAACTTGGGGTACCGCCCTTGCGAGCTTGG
      CTTTAATTATCCCACCGGCGTACGGAGTCTTTTGAACCCCATGGCGGGAACGCTCGAACC

Gly
      ArgHisArgAlaArgSerValArgAlaArgLeuLeuAlaArgGlyGlyArgAlaAlaIle
8761  AGACACCGGGCCCGGAGCGTCCGCGCTAGGCTTCTGGCCAGAGGAGGCAGGGCTGCCATA
      TCTGTGGCCCGGGCCTCGCAGGCGCGATCCGAAGACCGGTCTCCTCCGTCCCGACGGTAT

CysGlyLysTyrLeuPheAsnTrpAlaValArgThrLysLeuLysLeuThrProIleAla
8821  TGTGGCAAGTACCTCTTCAACTGGGCAGTAAGAACAAAGCTCAAACTCACTCCAATAGCG
      ACACCGTTCATGGAGAAGTTGACCCGTCATTCTTGTTTCGAGTTTGAGTGAGGTTATCGC

AlaAlaGlyGlnLeuAspLeuSerGlyTrpPheThrAlaGlyTyrSerGlyGlyAspIle
8881  GCCGCTGGCCAGCTGGACTTGTCCGGCTGGTTCACGGCTGGCTACAGCGGGGGAGACATT
      CGGCGACCGGTCGACCTGAACAGGCCGACCAAGTGCCGACCGATGTCGCCCCCTCTGTAA (Pro)
      TyrHisSerValSerHisAlaArgProArgTrpIleTrpPheCysLeuLeuLeuLeuAla
8941  TATCACAGCGTGTCTCATGCCCGGCCCCGCTGGATCTGGTTTTGCCTACTCCTGCTTGCT
      ATAGTGTCGCACAGAGTACGGGCCGGGGCGACCTAGACCAAAACGGATGAGGACGAACGA

AlaGlyValGlyIleTyrLeuLeuProAsnArgOP
9001  GCAGGGGTAGGCATCTACCTCCTCCCCAACCGATGAAGGTTGGGGTAAACACTCCGGCCT
      CGTCCCCATCCGTAGATGGAGGAGGGGTTGGCTACTTCCAACCCCATTTGTGAGGCCGGA
```

FIG. 1L

:42.16.XT1
GGTAGGGTCAAGGCTGAAATCGACTGTCTGCTTCTTTGGAGAAAGTGGTG

:42.17.XT1
ATCCTGGGGGAGCGTGATTGTCTCAATGGTCTTCTTTGGAGAAAGTGGTG

:42.18.XT1
AGTCCTGCCCCGACGTTGAGTGCGGGAGACCTTCTTTGGAGAAAGTGGTG

:42.19.XT1
CACAAATCTGTAGATGCCTGGCTTCCCCCTCTTCTTTGGAGAAAGTGGTG

:42.20.XT1
GTCGAACATGCCGGAGGGGCGCTCCCCGGCTTCTTTGGAGAAAGTGGTG

:42.21.LLA2C
GCCTGCGTCATAGCACTCACAGAGGACGGATTAGGCATAGGACCCGTGTC

:42.22LLA2C
AGTCTCGGCGGGCGTGAGCTCATACCAAGCTTAGGCATAGGACCCGTGTC

:42.23.LLA2C
CGGGGTGTTCATGTACGCTCGTAGCCTAACTTAGGCATAGGACCCGTGTC

"42.24.LLA2C
AAATTCAAGATGGTCCTGGCACACGGGAAGTTAGGCATAGGACCCGTGTC

:42.25.LLA2C
TATATGAGTGAGGCCTGTAAAGACGCCCTCTTAGGCATAGGACCCGTGTC

:42.26.LLA2C
ACTCTGCTTTGTCTGGGATAGAAAGTGGGCTTAGGCATAGGACCCGTGTC

:42.27.LLA2C
TTGGTACGCTACCAGGTAAGGAAGGTTCTCTTAGGCATAGGACCCGTGTC

:42.28.LLA2C
GGGAGGGGCTTGAGCCCTAGCGCACACGGTTTAGGCATAGGACCCGTGTC

:42.29.LLA2C
AATCAAACACTTCCACATCTGGTCCCACGATTAGGCATAGGACCCGTGTC

:42.30.LLA2C
GGGTGTTGGCCCATGGAGGGTGGGCTTGAGTTAGGCATAGGACCCGTGTC

:42.31.LLA2C
TTCATTCTGAACAGCGCCCAGTCTGTATAGTTAGGCATAGGACCCGTGTC

FIG. 2A

:42.XT1.1
TCCTCACAGGGGAGTGATTCATGGTGGAGTCTTCTTTGGAGAAAGTGGTG

:42.XT1.2
ATGGCTAGACGCTTTCTGCGTGAAGACAGTCTTCTTTGGAGAAAGTGGTG

:42.XT1.3
TCCTGGAGGCTGCACGACACTCATACTAACCTTCTTTGGAGAAAGTGGTG

:42.XT1.4
CGCAGACCACTATGGCTCTCCCGGGAGGGGCTTCTTTGGAGAAAGTGGTG

:42.XT1.5
TCGTCCTGGCAATTCCGGTGTACTCACCGGCTTCTTTGGAGAAAGTGGTG

:42.LLA2C.6
GCATTGAGCGGGTTGATCCAAGAAAGGACCTTAGGCATAGGACCCGTGTC

:42.LLA2C.7
AGCAGTCTTGCGGGGGCACGCCCAAATCTCTTAGGCATAGGACCCGTGTC

:42.LLA2C.8
ACAAGGCCTTTCGCGACCCAACACTACTCGTTAGGCATAGGACCCGTGTC

:42.LLA2C.9
GGGGCACTCGCAAGCACCCTATCAGGCAGTTTAGGCATAGGACCCGTGTC

:42.LLA2.10
CGTGCTCATGGTGCACGGTCTACGAGACCTTAGGCATAGGACCCGTGTC

:42.LLA2C.11
GTTACGTTTGTTTTTTTTTGAGGTTTAGGTTAGGCATAGGACCCGTGTC

:42.LLA2C.12
CGGGAACTTGACGTCCTGTGGGCGACGGTTTTAGGCATAGGACCCGTGTC

:42.LLA2C.13
CAAGTAAACTCCACCAACGATCTGACCGCCTTAGGCATAGGACCCGTGTC

:42.LLA2C.14
GCGCACACCCAATCTAGGGCCCCTGCGCGGTTAGGCATAGGACCCGTGTC

:42.LLA2C.15
AGGTTGCGACCGCTCGGAAGTCTTTCTCGTTTAGGCATAGGACCCGTGTC

FIG. 2B

:42.32.XT1
ATGTTGGGATGGGGCACAGTGACGGAGCCCCTTCTTTGGAGAAAGTGGTG

:42.33.XT1
ATCTCTCCGGTGGTGGACAGAGCAACCTCCCTTCTTTGGAGAAAGTGGTG

:42.34.XT1
ACTTCGAGGGGGATAGCCTTGCCGTAAAAACTTCTTTGGAGAAAGTGGTG

:42.35.XT1
TGACAGAAGATGAGATGTCTCCCCCCCTTGCTTCTTTGGAGAAAGTGGTG

:42.36.LLA2C
TTTGCGGCGAGTTCGTCGCACTTCTTCTTTTTAGGCATAGGACCCGTGTC

:42.37.LLA2C
TAGGCCACGGCATTGATGCCCAATGCGACCTTAGGCATAGGACCCGTGTC

:42.38.LLA2C
GTCGGGATGACGGACACGTCAAGACCGCGGTTAGGCATAGGACCCGTGTC

:42.39.LLA2C
GCATCGGTTGCCACGACGACAACATCGCCGTTAGGCATAGGACCCGTGTC

:42.40.LLA2C
GAGTCGAAGTCGCCGGTATAGCCGGTCATGTTAGGCATAGGACCCGTGTC

:42.41.LLA2C
GTCTGGGTGACACACGTATTGCAGTCTATCTTAGGCATAGGACCCGTGTC

:42.42.LLA2C
ATGGTGAAGGTAGGGTCAAGGCTGAAATCGTTAGGCATAGGACCCGTGTC

:42.43.LLA2C
GAGACAGCATCCTGGGGGAGCGTGATTGTCTTAGGCATAGGACCCGTGTC

FIG. 2C

```
    CysTrpValAlaMetThrProThrValAlaThrArgAspGlyLysLeuProAlaThrGln
  1 GTGTTGGGGTGGCGATGACCCCTACGGTGGCCACCAGGGATGGCAAACTCCCCGCGACGCA
    CACAACCCACCGCTACTGGGGATGCCACCGGTGGTCCTACCGTTTGAGGGCGCTGCGT

LeuArgArgHisIleAspLeuLeuValGlySerAlaThrLeuCysSerAlaLeuTyrVal
 61 GCTTCGACGTCACATCGATCTGCTTGTCGGGAGCGCCACCCTCTGTTCGGCCCTCTACGT
    CGAAGCTGCAGTGTAGCTAGACGAACAGCCCTCGCGGTGGGAGACAAGCCGGGAGATGCA

GlyAspLeuCysGlySerValPheLeuValGlyGlnLeuPheThrPheSerProArgArg
121 GGGGACCTATGCGGGGTCTGTCTTTCTTGTCGGCCAACTGTTCACCTTCTCCCCAGGCG
    CCCCCTGGATACGCCCCAGAGACAGAAAGAACAGCCGGTTGACAAGTGGAAGAGGGTCCGC

HisTrpThrThrGlnGlyCysAsnCysSerIleTyrProGlyHisIleThrGlyHisArg
181 CCACTGGACGACGCAAGGTTGCAATTGCTCTATCTATCCCGGCCATATAACGGGTCACCG
    GGTGACCTGCTGCGTTCCAACGTTAACGAGATAGATAGGGCCGGTATATTGCCCAGTGGC

------Overlap with CA84a------
    MetAlaTrpAspMetMetAsnTrpSerProThrThrAlaLeuValValAlaGlnLeu
241 CATGGCATGGGATATGATGAACTGGTCCCCTACGACGGTTGGTAGTGGCTCAGCT
    GTACCGTACCCTATACTACTTGACCAGGGATGCTGCCAACCATCACCGAGTCGA LeuArgIleProGlnAla
301 GCTCCGGATCCCACAAGCC
    CGAGGCCTAGGGTGTTCGG
```

FIG. 4

```
    SerGlyLysProAlaIleIleProAspArgGluValLeuTyrArgGluPheAspGluMet
  1 GTCCGGGAAGCCGGCAATCATACCTGACAGGAAGTCCTCTACCGAGAGTTCGATGAGAT
    CAGGCCCTTCGGCCGTTAGTATGGACTGTCCTTCAGGAGATGGCTCTCAAGCTACTCTA

GluGluCysSerGlnHisLeuProTyrIleGluGlnGlyMetMetLeuAlaGluGlnPhe
 61 GGAAGAGTGCTCTCAGCACTTACCGTATACGAGCAAGGGATGATGCTCGCCGAGCAGTT
    CCTTCTCACGAGAGTCGTGAATGGCATGTGCTTGTTCCCTACTACGAGCGGCTCGTCAA

LysGlnLysAlaLeuLeuGlnThrAlaSerArgGlnAlaGluValIleAlaAlaPro
121 CAAGCAGAAGGCCCTCCTGCAGACCGCGTCCCGTCAGGCAGAGGTTATCGCCCC
    GTTCGTCTTCCGGGAGGACGTCTGGCGCAGGGCAGTCCGTCTCCAATAGCGGGG

AlaValGlnThrAsnTrpGlnLysLeuGluThrPheTrpAlaLysHisMetTrpAsnPhe
181 TGCTGTCCAGACCAACTGGCAAAAACTCGAGACCTTCTGGGCAAAGCATATGTGGAACTT
    ACGACAGGTCTGGTTGACCGTTTTTGAGCTCTGGAAGACCCGTTTCGTATACACCTTGAA

IleSerGlyIleGlnTyrLeuAlaGlyLeuLeuSerThrLeuProGlyAsnProAlaIleAla
241 CATCAGTGGGATACAATACTTGGCGGGCCTTGTCAACGCTGCCTGGTAACCGCCATTGC
    GTAGTCACCCTATGTTATGAACCGCCCGGAACAGTTGCGACGGACCATTGGGCGGTAACG

SerLeuMetAlaPheThrAlaAlaValThrSerProLeuThrThrSerGln
301 TTCATTGATGGCTTTTACAGTGCTGTCACCAGCCCACTAACCACTAGCCAAA
    AAGTAACTACCGAAAATGTCGACAGTGGTCGGGTGATTGGTGATCGGTTT
```

FIG. 5

```
    AspAlaHisPheLeuSerGlnThrLysGlnSerGlyGluAsnLeuProTyrLeuValAla
  1 GATGCCCACTTTCTATCCCAGACACAAAGCAGAGTGGGGAGAACCTTCCTTACCTGGTAGCG
    CTACGGGTGAAAGATAGGGTCTGTTTCGTCTCACCCCTCTTGAAGGAATGGACCATCGC

TyrGlnAlaThrValCysAlaArgAlaAlaGlnAlaProProProSerTrpAspGlnMetTrp
 61 TACCAAGCCACCGTGTGCGCTAGGGCTGCTCAAGCCCCTCCCCCATCGTGGGACCAGATGTGG
    ATGGTTCGGTGGCACACGCGATCCGAGTTCGGGAGCCCGAGTTCGGGAGGGGTAGCACCCTGGTCTACACC

LysCysLeuIleArgLeuLysProThrLeuHisGlyProThrProLeuLeuTyrArgLeu
121 AAGTGTTTGATTCGCCTCAAGCCCACCCTCCATGGGCCAACACCCTGCTATACAGACTG
    TTCACAAACTAAGCGGAGTTCGGGAGTTCGGGAGTCCCCCGAGTTGTGGGACGATATGTCTGAC

GlyAlaValGlnAsnGluIleThrLeuThrHisProValThrLysTyrIleMetThrCys
181 GGCGCTGTTCAGAATGAAATCACCCTGACGCACCCAGTCACCAAATACATCATGACATGC
    CCGCGACAAGTCTTACTTTAGTGGGACTGCGTGGGTCAGTGGTTTATGTAGTACTGTACG

MetSerAlaAspLeuGluValThrSerThrGlyTrpValLeuValGlyGlyValLeuAla
241 ATGTCGGCCGACCTGGAGGTCACGAGCACCTGGGTGCTCGTTGGCGGCGTCCTGGCT
    TACAGCCGGCTGGACCTCCAGTGCTCGTGGACCCACGAGCAACGCCGCCAGGACCGA

AlaLeuAlaAlaTyrCysLeuSerThrGlyCysValValIleValAlaGlyArgValValLeu
301 GCTTTGGCCGCGTATTGCCTGTCAACAGGCTGTGGTGGTCATAGTGGCAGGTCGTCTTG
    CGAAACCGGCGCATAACGGACAGTTGTCCGACACCAGTATCACCCGTCCAGCAGAAC

──────Overlap with 81──────
    SerGlyLysProAlaIleIleProAspArgGluValLeuTyrArg
361 TCCGGGAAGCCGGCAATCATACCTGACAGGGAAGTCCTCTACCGAG
    AGGCCCTTCGGCCGTTAGTATGGACTGTCCCTTCAGGAGATGGCTC
```

FIG. 6

```
    LeuAlaAlaLysLeuLeuValAlaLeuGlyIleAsnAlaValAlaTyrTyrArgGlyLeuAsp
  1 CTCGCCGCAAAGCTGGTCGCATTGGGCATCAATGCCGTGGCCTACTACCGGGGTCTTGAC
    GAGCGGCGTTTCGACCAGCGTAACCCGTAGTTACGGCACCGGATGATGGCCCAGAACTG

ValSerValIleProThrSerGlyAspValValValValAlaThrAspAlaLeuMetThr
 61 GTGTCCGTCATCCCGACCAGCGGCGATGTTGTCGTCGTGGCAACCGATGCCCTCATGACC
    CACAGGCAGTAGGGCTGGTCGCCGCTACAACAGCAGCACCGTTGGCTACGGGAGTACTGG

GlyTyrThrGlyAspPheAspSerValIleAspTyrAsnThrCysValThrGlnThrVal
121 GGCTATACCGGCGACTTCGACTCGGTGATAGACTACAATACGTGTGTCACCCAGACAGTC
    CCGATATGGCCGCTGAAGCTGAGCCACTATCTGATGTTATGCACACAGTGGGTCTGTCAG

AspPheSerLeuAspProThrPheThrIleGluThrIleThrLeuProGlnAspAlaVal
181 GATTTCAGCCTTGACCCTACCTTCACCATTGAGACAATCACGCTCCCCCAGGATGCTGTC
    CTAAAGTCGGAACTGGGATGGAAGTGGTAACTCTGTTAGTGCGAGGGGTCCTACGACAG clone 35-----------------------Overlap with
    SerArgThrGlnArgArgGlyArgThr
241 TCCCGCACTCAACGTCGGGGCAGGACTG
    AGGGCGTGAGTTGCAGCCCCGTCCTGAC
```

FIG. 7

```
    GlnGlyCysAsnCysSerIleTyrProGlyHisIleThrGlyHisArgMetAlaTrpAsp
  1 CGCAAGGTTGCAATTGCTCTATCTATCCCGGCCATATAACGGGTCACCGGCATGGCATGGG
    GCGTTCCAACGTTAACGAGATAGATAGGGCCGGTATATTGCCCAGTGGCCGTACCGTACCC

MetMetMetAsnTrpSerProThrThrAlaLeuValMetAlaGlnLeuLeuArgIlePro
 61 ATATGATGATGAACTGGTCCCCTACGACGGCGTTGGTAATGGCTCAGCTGCTCCGGATCC
    TATACTACTACTTGACCAGGGGATGCTGCCGCAACCATTACCGAGTCGACGAGGCCTAGG

GlnAlaIleLeuAspMetIleAlaGlyAlaAlaHisTrpGlyValLeuAlaGlyIleAlaTyr
121 CACAAGCCATCTTGGACATGATCGCTGGTGCTGCTCACTGGGAGTCCTGGCGGGCATAGCGT
    GTGTTCGGTAGAACCTGTACTAGCGACCACGACGAGTGACCCTCAGGACCGCCCGTATCGCA

-------Overlap with CA59a-------
    PheSerMetValGlyAsnTrpAlaLysValLeuValValLeuLeuPheAlaGlyVal
181 ATTTCTCCATGGTGGGAACTGGGCAAAGGTTCTGGTAGTGCTGCTGCTATTTGCCGGCG
    TAAAGAGGTACCACCCCTTGACCCGTTTCCAAGACCATCACGACGACGATAAACGGCCGC AspAlaGluThrHisValThrGly
241 TCGACGCGGAAACCCACGTCACCGGGG
    AGCTGCGCCTTTGGGTGCAGTGGCCCC
```

```
          AlaTyrMetSerLysAlaHisGlyIleAspProAsnIleArgThrGlyLysValArgThrIle
  1       GCTTACATGTCCAAGGCTCATGGGATCGATCCTAACATCAGGACCGGGTGAGAACAAT
          CGAATGTACAGGTTCCGAGTACCCTAGCTAGGATTGTAGTCCTGGCCCACTCTTGTTA

ThrThrGlySerProIleThrTyrSerThrTyrGlyLysPheLeuAlaAspGlyGlyCys
 61       ACCACTGGACAGCCCATCACGTACTCCACCTACGGCAAGTTCCTTGCCGACGGCGGTG
          ATGGTGACCGTCGGGGTAGTGCATGAGGTGGATGCCGTTCAAGGAACGGCTGCCGCCAC

SerGlyGlyAlaTyrAspIleIleIleCysAspGluCysHisSerThrAspAlaThrSer
121       CTCGGGGGCGCTTATGACATAATTTGTGACGAGTGCCACTCCACGGATGCCACATC
          GAGCCCCCGCGAATACTGTATTATTAAACACTGCTCACGGTGAGGTGCCTACGGTGTAG

IleLeuGlyIleGlyThrValLeuAspGlnAlaGluThrAlaGlyAlaAlaArgLeuValVal
181       CATCTTGGGCATCGGCACTGTCCTTGACCAAGCAGAGACTGCGGGGGCGAGACTGGTTGT
          GTAGAACCCGTAGCCGTGACAGGAACTGGTTCGTCTCTGACGCCCCGCTCTGACCAACA

LeuAlaThrAlaThrProProGlySerValThrValProHisProAsnIleGluGluVal
241       GCTCGCCACCGCCACCCCTCCGGGCTCCGTCACTGTGCCCCATCCCAACATCGAGGAGT
          CGAGCGGTGGCGGTGGGGAGGCCCGAGGCAGTGACACGGGGTAGGTTGTAGCTCCTCCA

AlaLeuSerThrThrGlyPheGluIleProLeuGlyLysAlaIleIleProLeuGluValIle
301       TGCTCTGTCCACCACCGGAGAGATCCCTTTTACGGCAAGGCTATCCCCCTGAAGTAAT
          ACGAGACAGGTGGTGGCCTCTCTAGGGAAAAATGCCGTTCCGATAGGGGAGCTTCATTA

------Overlap with 37b-------
          LysGlyGlyGlyHisSerLysLysLysCysAspGluLeuAlaAla
361       AAGGGGGGAGACATCTCATTCTGTCATTCAAAGAAGAGTGCGACGAACTCGCCGC
          GTTCCCCCCCTCTGTAGAGTAGAAGACAGTAAGTTTCTTCTTCACGCTGCTTGAGCGGCG LysLeuValAlaLeuGlyIleAsnAlaValAlaTyrTyrArgGlyLeuAspValSerVal
421       AAAGCTGGTCGCATTGGGCATCAATGCCGTGGCCTACTACCGGGTCTTGACGTGTCCGT
          TTTCGACCAGCTAACCCGTAGTTACGGCACCGGATGATGGCCAGAACTGCACAGGCA --IleProThr
481       CATCCCGACCAG
          GTAGGGCTGGTC
```

FIG. 13

```
      ArgArgSerArgAsnLeuGlyLysValIleAspThrLeuThrCysGlyPheAlaAsp
  1   CCCGGCGTAGGTCGGCGCAATTGGGTAAGGTCATCGATACCCTTACGTGCGGCTTCGCCG
      GGGCCGCATCCAGCGCGTTAACCCATTCCAGTGCTATGGGAATGCACGCCGAAGCGGC

LeuMetGlyTyrIleProLeuValGlyLeuGlyGlyAlaAlaArgAlaLeuAla
 61   ACCTCATGGGGTACATACCGCTCGTCGGCCCCTCTTGGAGGCGCTGCCAGGGCCCTGG
      TGGAGTACCCCATGTATGGCGAGCAGCCGGGGAGAACTCCGCGACGGTCCCGGGACC

HisGlyValLeuGluGlyValAsnTyrAlaThrGlyValAsnLeuProGlyCys
121   CGATGGGCGTCCGGTTCTGGAAGACCTGAACTATGCAACAGGAACCTTCCTGTT
      GCGTACCCGCAGCCCAAGACCTTCTGCCGCACTTGATACGTGTCCCTTGAAGACCAA

SerPheSerIlePheLeuLeuAlaLeuLeuSerCysLeuThrValProAlaSerAlaTyr
181   GCTCTTTCTATCTTCCTTCTGGCCCTCCTCTTGCTCTTGACTGTGCCCGCTTCGGCCT
      CGAGAAAGAGATAGAAGGAAGACCGGGAGGAGAACGAACTGACACGGGCGAAGCCGGA

GlnValArgAsnSerThrGlyLeuTyrHisValThrAsnAspCysProAsnSerSerIle
241   ACCAAGTGCGCAACTCCACGGGCTTACCACGTGACCAATGATTGCCCTAACTCGAGTA
      TGGTTCACGCGTTGAGGTGCCCGAAATGGTGCAGTGGTTACTAACGGGATTGAGCTCAT

-------overlap with CA167b-------
      ValTyrGluAlaAlaAspAlaIleLeuHisThrProGlyCysValProCysValArgGlu
301   TTGTGTACGAAGCGGCCGATGCCATCCTGCACACTCCGGGGTGCGTCCCTTGCGTCGTG
      AACACATGCTTCGCCGGCTACGGTAGGACGTGTGAGGCCCACGCAGGGAACGCAAGCAC GlyAsnAlaSerArgCysTrpValAlaMetThrProThrValAla
361   AGGGCAACGCCTCGAGGTGTTGGGTGGCGATGACCCCTACGGTGGCC
      TCCCGTTGCGGAGCTCCACAACCCACCGCTACTGGGATGCCACCGG
```

```
                 LysLysAsnLysArgAsnThrAsnArgArgProGlnAspValLysPheProGlyGlyGly
  1  AAAAAAACAAACGTAACACCAACCGTCGCCCACAGGACGTCAAGTTCCCGGGTGGCG
     TTTTTTTTGTTTGCATTGTGGTTGGCAGCGGGTGTCCTGCAGTTCAAGGGCCCACCGC

GlnIleValGlyGlyValTyrLeuLeuProArgArgGlyProArgLeuGlyValArgAla
 61  GTCAGATCGTTGGTGGAGTTACTTGTTGCCGCGCAGGGCCCTAGAATTGGGTGCGCG
     CAGTCTAGCAACCACCTCAAATGAACAACGGCGCGTCCCGGGATCTAACCCACGCGC

ThrArgLysThrSerGluArgSerGlnProArgGlyArgArgGlnProIleProLysAla
121  CGACGAGAAAGACTTCCGAGCGGTCGCAACCTCGAGGTAGACGCCAGCCTATCCCAAGG
     GCTGCTCTTTCTGAAGGCTCGCCAGCGTTGGAGCTCCATCGGTCGGATAGGGTTCC

ArgArgProGluGlyGlyArgThrArgTrpAlaGlnProGlyTyrProTyrProLeuTyrGlyAsn
181  CTCGTCGGCCCGAGGCAGGACCTCGGCTCAGCCCGGTACCCTTGGCCCCCTCTATGGCA
     GAGCAGCCGGGCTCCCGTCCTGGACCCGAGTCGGGCCCATGGGAACCGGGAGATACCGT

GluGlyCysGlyTrpAlaGlyThrLeuLeuSerProArgGlySerArgProSerTrpGly
241  ATGAGGGCTGCGGGTGGGCGGGACCCCACCCGCCTACCGAGGACAGAGGGGCACCGAGAGCCGGATCGGG
     TACTCCCGACGCCCACGCCCTGGGGTGGGCGGATGGCTCCTGTCTCCCCGTGCTCTCGGCCTAGCTGG

ProThrAspProArgArgSerArgArgAsnLeuGlyLeuLysValIleAspThrLeuThrCys
301  GCCCCACAGACCCCCGGCTAGTGCGCGCAATTGGGTCGCGTAAGGTCATCGATACCCTTACGT
     CGGGGTGTCTGGGGGCCGATCACGCGCGTTAACCCAGCGCATTCCAGTAGCTATGGAATGCA

GlyPheAlaAspLeuMetGlyTyrIleProLeuValGlyAlaProLeuGlyAlaAla
361  GCGGCTTCGCCGACCTCATGGGCTACATACCGCTCGTCGGCGCCCCTCTTGAGGCGCTG
     CGCCGAAGCGGCTGGAGTACCCGATGTATGGCGAGCAGCGCCGGGGAGAACCTCCGGAC
     ----------overlap with CA216a----------
            ArgAlaLeuAlaHisGlyValArgValLeuGluAspGlyValAsnTyrAlaThrGlyAsn
421  CCAGGGCCCTGGCGCATGGCGGTCCGGTTCTGGAAGACGGCGTGAACTATGCAACAGGA
     GGTCCCGGGACCGCGTACCGCCAGGCCCAAGACCTTCTGCCGCACTTGATACGTTGTCCT LeuProGlyCysSerPheSerThrPhe
481  ACCTTCCTGGTTGCTCTTTCTTACCTTC
     TGGAAGGACCAACGAGAAAGAATGGAAG
```

FIG. 14

Translation of DNA ag30a

```
         GlnLysAlaSerSerHisGlyValSerMetSerValValGlnProProGlyProProLeu
  1  CGCAGAAAGCGTCTAGCCATGGCGTTAGTATGAGTGTCGTGCAGCCTCCAGGACCCCCC
     GCGTCTTTCGCAGATCGGTACCGCAATCATACTCACAGCACGTCGGAGGTCCTGGGGGGG

ProGlyGluProAM TrpSerAlaGluProValSerThrProGluLeuProGlyArgPro
 61  TCCCGGGAGAGCCATAGTGGTCTGCGGAACCGGTGAGTACACCGGAATTGCCAGGACGAC
     AGGGCCCTCTCGGTATCACCAGACGCCTTGGCCACTCATGTGGCCTTAACGGTCCTGCTG

GlyProPheLeuAspGlnProAlaGlnCysLeuGluIleTrpAlaCysProArgLysThr
121  CGGGTCCTTTCTTGGATCAACCCGCTCAATGCCTGGAGATTTGGGCGTGCCCCCGCAAGA
     GCCCAGGAAAGAACCTAGTTGGGCGAGTTACGGACCTCTAAACCCGCACGGGGGCGTTCT

AlaSerArgValValLeuGlyArgGluArgProCysGlyThrAlaOP AM GlyAlaCys
181  CTGCTAGCCGAGTAGTGTTGGGTCGCGAAAGGCCTTGTGGTACTGCCTGATAGGGTGCTT
     GACGATCGGCTCATCACAACCCACCGCTTTCCGGAACACCATGACGGACTATCCCACGAA
                                                 *              ---
         GluCysProGlyArgSerArgArgProCysThrMetSerThrAsnProLysProGlnLys
241  GCGAGTGCCCCGGGAGGTCTCGTAGACCGTGCACCATGAGCACGAATCCTAAACCTCAAA
     CGCTCACGGGGCCCTCCAGAGCATCTGGCACGTGGTACTCGTGCTTAGGATTTGGAGTTT
     ------------------------------------------------------------
         LysAsnLysArgAsnThrAsnArgArgProGlnAspValLysPheProGlyGlyGlyGln
301  AAAAAAACAAACGTAACACCAACCGTCGCCCACAGGACGTCAAGTTCCCGGGTGGCGGTC
     TTTTTTTGTTTGCATTGTGGTTGGCAGCGGGTGTCCTGCAGTTCAAGGGCCCACCGCCAG
     ------------------------------------------------------------
         IleValGlyGlyValTyrLeuLeuProArgArgGlyProArgLeuGlyValArgAlaThr
361  AGATCGTTGGTGGAGTTTACTTGTTGCCGCGCAGGGGCCCTAGATTGGGTGTGCGCGCGA
     TCTAGCAACCACCTCAAATGAACAACGGCGCGTCCCCGGGATCTAACCCACACGCGCGCT
     ---------------Overlap with CA290a--------------------------
         ArgLysThrSerGluArgSerGlnProArgGlyArgArgGlnProIleProLysAlaArg
421  CGAGAAAGACTTCCGAGCGGTCGCAACCTCGAGGTAGACGTCAGCCTATCCCCAAGGCTC
     GCTCTTTCTGAAGGCTCGCCAGCGTTGGAGCTCCATCTGCAGTCGGATAGGGGTTCCGAG
     ------------------------------------------------------------
         ArgProGluGlyArgThrTrpAlaGlnProGlyTyrProTrpProLeuTyrGlyAsnGlu
481  GTCGGCCCGAGGGCAGGACCTGGGCTCAGCCCGGGTACCCTTGGCCCCTCTATGGCAATG
     CAGCCGGGCTCCCGTCCTGGACCCGAGTCGGGCCCATGGGAACCGGGGAGATACCGTTAC
     ------------------------------------------------------------
         GlyCysGlyTrpAlaGlyTrpLeuLeuSerProArgGlySerArgProSerTrpGlyPro
541  AGGGCTGCGGGTGGGCGGGATGGCTCCTGTCTCCCCGTGGCTCTCGGCCTAGCTGGGGCC
     TCCCGACGCCCACCCGCCCTACCGAGGACAGAGGGGCACCGAGAGCCGGATCGACCCCGG
     ------------------------------------------------------------
         ThrAspProArgArgArgSerArgAsnLeuGlyLysValIleAspThrLeuThrCysGly
601  CCACAGACCCCCGGCGTAGGTCGCGCAATTTGGGTAAGGTCATCGATACCCTTACGTGCG
     GGTGTCTGGGGGCCGCATCCAGCGCGTTAAACCCATTCCAGTAGCTATGGGAATGCACGC
     -----
         Phe
661  GCTTC
     CGAAG
```

*Putative initiator methionine of HCV polyprotein

FIG. 15

```
     SerIleGluThrIleThrLeuProGlnAspAlaValSerArgThrGlnArgArgGlyArg
  1  TCCATTGAGACAATCACGCTCCCCAGGATGCTGTCTCCGCACTCAACGTCGGGCAGG
     AGGTAACTCTGTTAGTGCGAGGGGTCCTACGACAGAGGGCGTGAGTTGCAGCCCCGTCC

ThrGlyArgGlyLysProGlyIleTyrArgPheValAlaProGlyGluArgProSerGly
 61  ACTGGCAGGGGAAGCCAGGCATCTACAGATTTGTGGCACCGGGGGAGCGCCCTCCGGC
     TGACCGTCCCCTTCGGTCCGTAGATGTCTAAACACCGTGGCCCCCTCGCGGGAGGCCG

MetPheAspSerSerValLeuCysGluCysTyrAspAlaGlyCysAlaTrpTyrGluLeu
121  ATGTTCGACTCGTCCGTCCTCTGTGAGTGCTATGACGCAGGCTGTGCTTGGTATGAGCTC
     TACAAGCTGAGCAGGCAGGACACTCACGATACTGCGTCCGACACGAACCATACTCGAG

ThrProAlaGluThrThrValArgLeuArgAlaTyrMetAsnThrProGlyLeuProVal
181  ACGCCCGGCGAGACTACAGTTAGGCTACGAGGCTACATGAACACCCCGGGCTTCCCGTG
     TGCGGGCCGCTCTGATGTCAATCCGATGCTCCGTACTTGTGGGGCCCCGAAGGGCAC
```

FIG. 17A

```
         CysGlnAspHisLeuGluPheTrpGluGlyValPheThrGlyLeuThrHisIleAspAla
241 TGCCAGGACCATCTTGAATTTTGGGAGGGGTGTCTTTACAGGCCTCACTCATATAGATGCC
    ACGGTCCTGGTAGAACTTAAAACCCTCCCCACAGAAATGTCCGGAGTGAGTATATCTACGG

HisPheLeuSerGlnThrLysGlnSerGlyGluAsnLeuProTyrLeuValAlaTyrGln
301 CACTTTCTATCCCAGACAAAGCAGAGTGGGGAGAACCTTCCTTACCTGGTAGCGTACCAA
    GTGAAAGATAGGGTCTGTTTCGTCTCACCCCTCTTGGAAGGAATGGACCATCGCATGGTT

----------Overlap with 36---------
         AlaThrValCysAlaArgAlaAlaGlnAlaProProSerTrpAspGlnMetTrpLysCys
361 GCCACCGTGTGCGCTAGGGCTGCCCAAGCCTCCCCCATCGTGGGACCAGATGTGGAAGTGT
    CGGTGGCACACGCGATCCCGAGTTCGGAGGGGTAGCACCCTGGTCTACACCTTCACA LeuIleArgLeuLysProThrLeuHisGlyProThrProLeuLeuTyrArgLeuGlyAla
421 TTGATTCGCCTCAAGCCCACCCTCCATGGCCCAACACCCCTGCTATACAGACTGGGCGCT
    AACTAAGCGGAGTTCGGGTGGGAGGTACCCGGTTGTGGGGACGATATGTCTGACCCGCGA
```

FIG. 17B

```
            1   MetSerThrAsnProLysProGlnLysLysAsnLysArgAsnThrAsnArgArgProGln
HCV-1       1   atgagcacgaatcctaaacctcaaaaaaaaaacaaacgtaacaccaaccgtcgcccacag
HCT18       ------------------------------g-----c-----------------------
Th          ------------------------------g-----c-----------------------
HCV JH      ----------a-------------c-----g-----c-----------------------
HC-J1       ----------t---c---------------g-----c-----------------------
HC-J4       ------------------------------g-----c---------------c-------

21   AspValLysPheProGlyGlyGlyGlnIleValGlyGlyValTyrLeuLeuProArgArg
HCV-1      61   gacgtcaagttcccggggtggcggtcagatcgttggtggagtttacttgttgccgcgcagg
HCT18       ------------------------------------------------------------
Th          ------------------------------------------------------------
HCV JH      ------t-----------c--t-----------c--------------------------
HC-J1       ------------------------------------------------------------
HC-J4       ----------------c--t----------------------------c-----------

41   GlyProArgLeuGlyValArgAlaThrArgLysThrSerGluArgSerGlnProArgGly
HCV-1     121   ggccctagattgggtgtgcgcgcgacgagaaagacttccgagcggtcgcaacctcgaggt
HCT18       -----------------------------g------------------------------c
Th          ----c--g----------------------g-----------------------------
HCV JH      ----c--g-----------t-----t--g------------------------t--a
HC-J1       -----------------------------g------------------------------
HC-J4       ----c--g-----------t-----t--g------------------------t--a 61   ArgArgGlnProIleProLysAlaArgArgProGluGlyArgThrTrpAlaGlnProGly
HCV-1     181   agacgtcagcctatccccaaggctcgtcggcccgagggcaggacctgggctcagcccggg
HCT18       --g--------------------a---------t--------------------------
Th          -----------------------a------------------------------------
HCV JH      --g--a--a-------------------c----------------------------t---
HC-J1       ---------------------tg-------------------------------------
HC-J4       t-g--a--a-------------c--a-----------g----------------------

81   TyrProTrpProLeuTyrGlyAsnGluGlyCysGlyTrpAlaGlyTrpLeuLeuSerPro
HCV-1     241   tacccttggcccctctatggcaatgagggctgcgggtgggcgggatggctcctgtctccc
HCT18       -------------------------------t--t-------------------------
Th          --t---------------------------------------------------------
HCV JH      --t---------------------------tg--------a--------------a---
HC-J1       ------------------------------------------------------------
HC-J4       ------------------------------tg--------a--------------a---

101   ArgGlySerArgProSerTrpGlyProThrAspProArgArgArgSerArgAsnLeuGly
HCV-1     301   cgtggctctcggcctagctggggccccacagacccccggcgtaggtcgcgcaatttgggt
HCT18       ---------------t--------------------------------------------
Th          ------------------------------------------c-----------------
HCV JH      --c------------t----------at------------------------t-------
HC-J1       ------------------t----------g------------------------------
HC-J4       --c-----c------t-------------g----------------------t--c----

121   LysValIleAspThrLeuThrCysGlyPheAlaAspLeuMetGlyTyrIleProLeuVal
HCV-1     361   aaggtcatcgatacccttacgtgcggcttcgccgacctcatggggtacataccgctcgtc
HCT18       --------------------------------------------------t---------
Th          ------------------------------------------------------------
HCV JH      ---------------------a----------------------------t---------
HC-J1       ---------------c--------------------------------------------
HC-J4       ---------------a----------------t---------t--t--------------
```

FIG. 18A

```
                141  GlyAlaProLeuGlyGlyAlaAlaArgAlaLeuAlaHisGlyValArgValLeuGluAsp
HCV-1           421  ggcgcccctcttggaggcgctgccagggccctggcgcatggcgtccgggttctggaagac
HCT18                ------------------------------------------------------------
Th                   ---------------g--------------------------------------------
HCV JH               --------ct-a--g---------------------a-----t-------------g---
HC-J1                ------------------------------------------------------------
HC-J4                --------c--a--g----------------t----a--c--t-------------g---

161  GlyValAsnTyrAlaThrGlyAsnLeuProGlyCysSerPheSerIlePheLeuLeuAla
HCV-1           481  ggcgtgaactatgcaacagggaaccttcctggttgctctttctctatcttccttctggcc
HCT18                ------------------------------------------------------------
Th                   ----------------------------------------c-------------------
HCV JH               ------------------------tt-g--c----------------------ct----t
HC-J1                ------------------------------------------------------------
HC-J4                -------------------------t-g--c----------------------ct----t 181  LeuLeuSerCysLeuThrValProAlaSer  190
HCV-1           541  ctgctctcttgcttgactgtgcccgcttcg  571
HCT18                ------------c----------------a
Th                   ------------tc----c----------a
HCV JH               -----g--c--t-----ca-c--a-----c
HC-J1                ------------c----------------a
HC-J4                t----g--c--t-----ca-c--a-----c
```

FIG. 18B

| Probe Type | Probe Number | Complement of Nucleotide Numbers |
|---|---|---|
| Label | 42.LLA2C.44 | 16 to 45 |
| Label | 42.LLA2C.45 | 49 to 78 |
| Label | 42.LLA2C.46 | 82 to 111 |
| Label | 42.LLA2C.47 | 115 to 144 |
| Label | 42.LLA2C.48 | 148 to 177 |
| Label | 42.LLA2C.49 | 211 to 240 |
| Label | 42.LLA2C.50 | 242 to 271 |
| Label | 42.LLA2C.51 | 275 to 304 |
| Label | 42.LLA2C.52 | 332 to 361 |
| Label | 42.LLA2C.53 | 365 to 394 |
| Label | 42.LLA2C.54 | 398 to 427 |
| Label | 42.LLA2C.55 | 457 to 486 |

FIG. 20

Probes for Hepatitus C Virus

:42.LLA2C.44
GGTGTTACGTTTGKTTTTTYTTTGRGGTTTTTAGGCATAGGACCCGTGTC

:42.LLA2C.45
RCCCGGGAACTTRACGTCCTGTGGGCGRCGTTAGGCATAGGACCCGTGTC

:42.LLA2C.46
CAACARGTAAACTCCACCRACGATCTGACCTTAGGCATAGGACCCGTGTC

:42.LLA2C.47
CGCRCGCACACCCAAYCTRGGGCCCCTGCGTTAGGCATAGGACCCGTGTC

:42.LLA2C.48
WCGAGGTTGCGACCGCTCGGAAGTCTTYCTTTAGGCATAGGACCCGTGTC

:42.LLA2C.49
CCCGGGCTGAGCCCAGGYCCYGCCCTCGGRTTAGGCATAGGACCCGTGTC

:42.LLA2C.50
MARCCCTCATTGCCATAGAGGGGCCAAGGRTTAGGCATAGGACCCGTGTC

:42.LLA2C.51
CCRCGGGGWGACAGGAGCCATCCYGCCCACTTAGGCATAGGACCCGTGTC

:42.LLA2C.52
ACCCAARTTRCGCGACCTRCGCCGGGGGTCTTAGGCATAGGACCCGTGTC

:42.LLA2C.53
GGCGAAGCCGCAYGTRAGGGTATCGATGACTTAGGCATAGGACCCGTGTC

:42.LLA2C.54
GGCGCCGACGAGCGGWATRTACCCCATGAGTTAGGCATAGGACCCGTGTC

:42.LLA2C.55
CACGCCGTCYTCCAGAACCCGGACMCCRTGTTAGGCATAGGACCCGTGTC

IUB GROUP CODES

NANBV DIAGNOSTICS: POLYNUCLEOTIDES USEFUL FOR SCREENING FOR HEPATITIS C VIRUS

CROSS-REFERENCE TO RELATED APPLICATIONS

This application is a continuation of U.S. Ser. No. 07/566,209, filed 8 Aug. 1990, now abandoned; which is a continuation-in-part of attorney docket 2300-0063.32 (U.S. Ser. No. 07/505,435) filed 4 Apr. 1990, now abandoned; which is a continuation in part of attorney docket 2300-0063.31 (U.S. Ser. No. 07/456,637) filed 21 Dec. 1989, now abandoned; attorney docket 2300-0063.28 (U.S. Ser. No. 07/355,002) filed 18 May 1989, now abandoned, and of attorney docket 2300-0063.27 (07/355,961) filed 18 May 1989, now abandoned; which are continuations-in-part of attorney docket number 2300-0063.29 (U.S. Ser. No. 07/341,334) filed 20 Apr. 1989, now abandoned; which is a continuation-in-part of attorney docket number 2300-0063.59 (PCT/US88/04125) filed 18 Nov. 1988, converted to U.S. National phase on 21 Apr. 1989 and assigned attorney docket number 2300-0063.26 (U.S. Ser. No. 353,896, now abandoned), and a continuation-in-part of attorney docket number 2300-0063.25 (U.S. Ser. No. 07/325,338) filed 17 Mar. 1989 (now abandoned); which are continuations-in-part of attorney docket number 2300-0063.24 (U.S. Ser. No. 271,450) filed 14 Nov. 1988, now abandoned; which is a continuation-in-part of attorney docket number 2300-0063.23 (U.S. Ser. No. 263,584) filed 26 Oct. 1988, now abandoned; which is a continuation-in-part of attorney docket number 2300-0063.22 (formerly 2300-0237, U.S. Ser. No. 191,263) filed 6 May 1988, now abandoned; which is a continuation-in-part of attorney docket number 2300-0063.21 (formerly 2300-0228, U.S. Ser. No. 161,072) filed 26 Feb. 1988, now abandoned; which is a continuation-in-part of attorney docket number 2300-0063.20 (formerly 2300-0219, U.S. Ser. No. 139,886) filed 30 Dec. 1987, now abandoned; which is a continuation-in-part of attorney docket number 2300-0063 (formerly 2300-0203, U.S. Ser. No. 122,714) filed 18 Nov. 1987, now abandoned; the aforementioned applications are, in their entirety, incorporated herein by reference.

TECHNICAL FIELD

The invention relates to materials and methodologies for managing the spread of non-A, non-B hepatitis virus (NANBV) infection. More specifically, it relates to an etiologic agent of non-A, non-B hepatitis (NANBH), hepatitis C virus (HCV), and to polynucleotides and analogs thereof, which are useful in assays for the detection of HCV in biological samples.

REFERENCES CITED IN THE APPLICATION

Barr et al. (1986), Biotechniques 4:428.
Beaucage et al. (1981), Tetrahedron Letters 22:1859.
Botstein (1979), Gene 8:17.
Brinton, M. A. (1986) in THE VIRUSES: THE TOGAVIRIDAE AND FLAVIVIRIDAE (Series eds. Fraenkel-Conrat and Wagner, vol. eds. Schlesinger and Schlesinger, Plenum Press), p. 327–374.
Broach (1981) in: Molecular Biology of the Yeast Saccharomyces, Vol. 1, p. 445, Cold Spring Harbor Press.
Broach et al. (1983), Meth. Enz. 101:307.
Brown et al. (1979), Methods in Enzymology 68:109.
Byrne et al. (1988), Nucleic Acids Res. 16:4165.
Castle et al. (1986), Virology 119:10.
Chang et al. (1977), Nature 198:1056.
Chirgwin et al. (1979), Biochemistry 18:5294.
Choo et al. (1989), Science 244:359.
Chomczynski and Sacchi (1987), Analytical Biochemistry 162:156.
Clewell et al. (1969), Proc. Natl. Acad. Sci. U.S.A. 62:1159.
Clewell (1972), J. Bacteriol. 110:667.
Cohen (1972), Proc. Natl. Acad. Sci. U.S.A. 69:2110.
Cousens et al. (1987), Gene 61:265.
De Boer et al. (1983), Proc. Natl. Acad. Sci. U.S.A. 292:128.
Dreesman et al. (1985), J. Infect. Disease 151:761.
Feinstone et al. (1981), J. Inf. Dis. 144: 588.
Feinstone et al. (1983), Infection and Immunology 41:816.
Feinstone, S. M. and Hoofnagle, J. H. (1984), New Engl. J. Med. 311:185.
Fields & Knipe (1986), FUNDAMENTAL VIROLOGY (Raven Press, New York).
Fiers et al. (1978), Nature 273:113.
Gerety, R. J. et al., in VIRAL HEPATITIS AND LIVER DISEASE (Vyas, B. N., Dienstag, J. L., and Hoofnagle, J. H., eds.
Grune and Stratton, Inc., 1984) pp 23–47.
Goeddel et al. (1980), Nucleic Acids Res. 8:4057.
Graham and Van der Eb (1978), Virology 52:546.
Grunstein and Hogness (1975), Proc. Natl. Acad. Sci. U.S.A. 73:3961.
Grych et al. (1985), Nature 316:74.
Gubler and Hoffman (1983), Gene 25:263.
Hahn et al. (1988), Virology 162:167.
Han (1987), Biochemistry 26:1617.
Hammerling et al. (1981), MONOCLONAL ANTIBODIES AND T-CELL HYBRIDOMAS.
Hess et al. (1968), J. Adv. Enzyme Reg 2:149.
Hinnen et al. (1978), Proc. Natl. Acad. Sci. 75:1929.
Hitzeman et al. (1980), J. Biol. Chem. 255:2073.
Holland et al. (1978), Biochemistry 17:4900.
Holland (1981), J. Biol. Chem. 256: 1385.
Houghton et al. (1981), Nucleic Acids Res. 9:247
Huynh, T. V. et al. (1985) in DNA CLONING TECHNIQUES; A PRACTICAL APPROACH (D. Glover, Ed., IRL Press, Oxford, U.K.) pp. 49–78.
Immun. Rev. (1982) 62:185.
Iwarson (1987), British Medical J. 295:946.
Kennett et al. (1980) MONOCLONAL ANTIBODIES.
Kuo et al. (1989), Science 244:362.
Kyte and Doolittle (1982), J. Mol. Biol. 157:105–132.
Landegren et al. (1988), Science 242:229.
Maniatis, T., et al. (1982) MOLECULAR CLONING; A LABORATORY MANUAL (Cold Spring Harbor Press, Cold Spring Harbor, N.Y.).
Matthews and Kricka (1988), Analytical Biochemistry 169:1. METHODS IN ENZYMOLOGY (Academic Press).
Mittlin (1989), Clinical Chem. 35:1819.
Laemmli (1970), Nature 227, 680.
Lee et al. (1988), Science 239:1288.
Loh et al. (1989), Science 243:217.
Mackow et al. (1987), Virology 159:217.
Mayer and Walker, eds. (1987), IMMUNOCHEMICAL METHODS IN CELL AND MOLECULAR BIOLOGY (Academic Press, London).
Mayumi et al. (1990), Japanese J. Exp. Med. 60:167.
Maxam et al. (1980), Methods in Enzymology 65:499.
MacNamara et al. (1984), Science 226:1325.
Messing et al. (1981), Nucleic Acids Res. 9:309.
Messing (1983), Methods in Enzymology 101:20–37.
METHODS IN ENZYMOLOGY (Academic Press).

Michelle et al., Int. Symposium on Viral Hepatitis.
Monath (1986) in THE VIRUSES: THE TOGAVIRADAE AND FLAVIVIRIDAE (Series eds. Fraenkel-Conrat and Wagner, vol. eds. Schlesinger and Schlesinger, Plenum Press), p. 375–440.
Murakawa et al. (1988), DNA 7:287.
Nagahuma et al. (1984), Anal. Biochem. 141:74.
Narang et al (1979), Methods in Enzymology 68:90.
Neurath et al. (1984), Science 224:392.
Nisonoff et al. (1981), Clin. Immunol. Immunopathol. 21:397–406.
Overby, L. R. (1985), Curr. Hepatol. 5:49.
Overby, L. R. (1986), Curr. Hepatol. 6:65.
Overby, L. R. (1987), Curr. Hepatol. 7:35.
Peleg (1969), Nature 221:193.
Pfefferkorn and Shapiro (1974), in COMPREHENSIVE VIROLOGY, Vol. 2 (Fraenkel-Conrat & Wagner, eds., Plenum, New York) pp. 171–230.
Prince, A. M. (1983), Annu. Rev. Microbiol. 37:217.
Rice et al. (1985), Science 229:726.
Rice et al. (1986) in THE VIRUSES: THE TOGAVIRIDAE AND FLAVIVIRIDAE (Series eds. Fraenkel-Conrat and Wagner, vol. eds. Schlesinger and Schlesinger, Plenum Press), p. 279–328.
Roehrig (1986) in THE VIRUSES: THE TOGAVIRIDAE AND FLAVIVIRIDAE (Series eds. Fraenkel-Conrat and Wagner, vol. eds. Schlesinger and Schlesinger, Plenum Press)
Rosenberg et al. (1984), Nature 312:7.
Sadler et al. (1980), Gene 8, 279.
Saiki et al. (1985), Science 230:1350.
Saiki et al. (1986), Nature 324: 163.
Saiki et al. (1988), Science 239:487.
Sanger et al. (1977), Proc. Natl. Acad. Sci. U.S.A. 74:5463.
Scharf et al. (1986), Science 233:1076.
Schlesinger et al. (1986), J. Virol. 60:1153.
Schreier, M., et al. (1980) HYBRIDOMA TECHNIQUES
Scopes (1984), PROTEIN PURIFICATION, PRINCIPLES AND PRACTICE, SECOND EDITION (Springer-Verlag, New York).
Shimatake et al. (1981), Nature 292:128.
Shigekawa and Dower (1988), BioTechniques 6:742.
Steimer et al. (1986), J. Virol. 58:9.
Stollar (1980), in THE TOGAVIRUSES (R. W. Schlesinger, ed., Academic Press, New York), pp. 584–622.
Sumiyoshi et al. (1987), Virology 161:497.
Taylor et al. (1976), Biochem. Biophys. Acta 442:324.
Towbin et al. (1979), Proc. Natl. Acad. Sci. U.S.A. 76, 4350.
Tsu and Herzenberg (1980), in SELECTED METHODS IN CELLULAR IMMUNOLOGY (W. H. Freeman and Co.) pp. 373–391.
Vytdehaag et al. (1985), J. Immunol. 134:1225.
Valenzuela, P., et al. (1982), Nature 298:344.
Valenzuela, P., et al. (1984), in HEPATITIS B (Millman, L. et al., ed, Plenum Press) pp. 225–236.
Warner (1984), DNA 3:401.
Wu and Grossman (1987), Methods in Enzymology Vol. 154, RECOMBINANT DNA, Part E.
Wu (1987), Methods in Enzymology vol 155, RECOMBINANT DNA, part F.
Zoller (1982), Nucleic Acids Res. 10:6487.
Cited Patents
U.S. Pat. No. 4,341,761
U.S. Pat. No. 4,399,121
U.S. Pat. No. 4,427,783
U.S. Pat. No. 4,444,887
U.S. Pat. No. 4,466,917
U.S. Pat. No. 4,472,500
U.S. Pat. No. 4,491,632
U.S. Pat. No. 4,493,890
U.S. Pat. No. 4,683,202
U.S. Pat. No. 4,458,066
U.S. Pat. No. 4,868,105

BACKGROUND ART

Non-A, Non-B hepatitis (NANBH) is a transmissible disease or family of diseases that are believed to be viral-induced, and that are distinguishable from other forms of viral-associated liver diseases, including that caused by the known hepatitis viruses, i.e., hepatitis A virus (HAV), hepatitis B virus (HBV), and delta hepatitis virus (HDV), as well as the hepatitis induced by cytomegalovirus (CMV) or Epstein-Barr virus (EBV). NANBH was first identified in transfused individuals. Transmission from man to chimpanzee and serial passage in chimpanzees provided evidence that NANBH is due to a transmissible infectious agent or agents.

Epidemiologic evidence is suggestive that there may be three types of NANBH: the water-borne epidemic type; the blood or needle associated type; and the sporadically occurring (community acquired) type. However, the number of agents which may be the causative of NANBH are unknown.

There have been a number of candidate NANBV. See, for example the reviews by Prince (1983), Feinstone and Hoofnagle (1984), and Overby (1985, 1986, 1987) and the article by Iwarson (1987). However, there is no proof that any of these candidates represent the etiological agent of NANBH.

The demand for sensitive, specific methods for screening and identifying carriers of NANBV and NANBV contaminated blood or blood products is significant. Post-transfusion hepatitis (PTH) occurs in approximately 10% of transfused patients, and NANBH accounts for up to 90% of these cases. The major problem in this disease is the frequent progression to chronic liver damage (25–55%).

Patient care as well as the prevention of transmission of NANBH by blood and blood products or by close personal contact require reliable screening, diagnostic and prognostic tools to detect nucleic acids, antigens and antibodies related to NANBV.

Methods for detecting specific polynucleotides by hybridization assays are known in the art. See, for example, Matthews and Kricka (1988), Analytical Biochemistry 169:1; Landegren et al. (1988), Science 242:229; and Mittlin (1989), Clinical chem. 35:1819. U.S. Pat. No. 4,868,105, issued Sep. 9, 1989, and in EPO Publication No. 225,807 (published Jun. 16, 1987).

DISCLOSURE OF THE INVENTION

Methods for isolating and/or detecting specific polynucleotides by hybridization could not be used for screening for HCV until Applicants' discovery of HCV, which provides materials and methods for obtaining the viral genomic sequences, which are provided in U.S. Pat. No. 5,350,671, and infra. Accordingly, one aspect of the invention is an oligomer capable of hybridizing to an HCV sequence in an analyte polynucleotide strand, wherein the oligomer is comprised of an HCV targeting sequence complementary to at least 4 contiguous nucleotides of HCV cDNA shown in FIG. 1.

Another aspect of the invention is a process for detecting an HCV sequence in an analyte strand suspected of containing an HCV polynucleotide, wherein the HCV polynucleotide comprises a selected target region, said process comprising:

(a) providing an oligomer capable of hybridizing to an HCV sequence in an analyte polynucleotide strand, wherein the oligomer is comprised of an HCV targeting sequence complementary to at least 4 contiguous nucleotides of HCV cDNA shown in FIG. 1

(b) incubating the analyte strand with the oligomer of (a) which allow specific hybrid duplexes to form between the targeting sequence and the target sequence; and (d) detecting hybrids formed between target region, if any, and the oligomer.

Yet another aspect of the invention is a method for preparing blood free of HCV comprising:

(a) providing analyte nucleic acids from a sample of blood suspected of containing an HCV target sequence;

(b) providing an oligomer capable of hybridizing to the HCV sequence in an analyte polynucleotide strand, if any, wherein the oligomer is comprised of an HCV targeting sequence complementary to a sequence of at least 8 nucleotides present in a conserved HCV nucleotide sequence in HCV RNA;

(c) reacting (a) with (b) under conditions which allow the formation of a polynucleotide duplex between the targeting sequence and the target sequence, if any;

(d) detecting a duplex formed in (c), if any; and (e) saving the blood from which complexes were not detected in (d).

BRIEF DESCRIPTION OF THE DRAWINGS

FIG. 4 shows the nucleotide sequence of HCV cDNA in clone CA156e, the amino acids encoded therein, and the sequences which overlap with CA84a.

FIG. 5 shows the double-stranded nucleotide sequence of the HCV cDNA insert in clone 81, and the putative amino acid sequence of the polypeptide encoded therein.

FIG. 6 shows the HCV cDNA sequence in clone 36, the segment which overlaps the NANBV cDNA of clone 81, and the polypeptide sequence encoded within clone 36.

FIG. 7 shows the HCV cDNA sequence in clone 37b, the segment which overlaps clone 35, and the polypeptide encoded therein.

FIG. 10 shows the nucleotide sequence of HCV cDNA in clone CA84a, the amino acids encoded therein, and the sequences which overlap with clone CA59a.

FIG. 11 shows the HCV cDNA sequence in clone 40b, the segment which overlaps clone 37b, and the polypeptide encoded therein.

FIG. 13 shows the nucleotide sequence of HCV cDNA in clone CA216a, the amino acids encoded therein, and the overlap with clone CA167b.

FIG. 14 shows the nucleotide sequence of HCV cDNA in clone CA290a, the amino acids encoded therein, and the overlap with clone CA216a.

FIG. 15 shows the nucleotide sequence of HCV cDNA in clone ag30a and the overlap with clone CA290a.

FIG. 17 shows the HCV cDNA sequence in clone 35, the segment which overlaps clone 36, and the polypeptide encoded therein.

FIG. 18 shows the consensus sequences for five different HCV isolates from Japan and the United States.

FIG. 19 is a set of probes useful for the detection of HCV RNA derived from the core region.

FIG. 20 correlates the probes in FIG. 19 with their corresponding complementary regions in the HCV genome.

FIG. 23 consists of two panels, FIGS. 23a and 23b, which are reproductions of the filters probed with the plus and minus strands, respectively.

MODES FOR CARRYING OUT THE INVENTION

Figure 3:
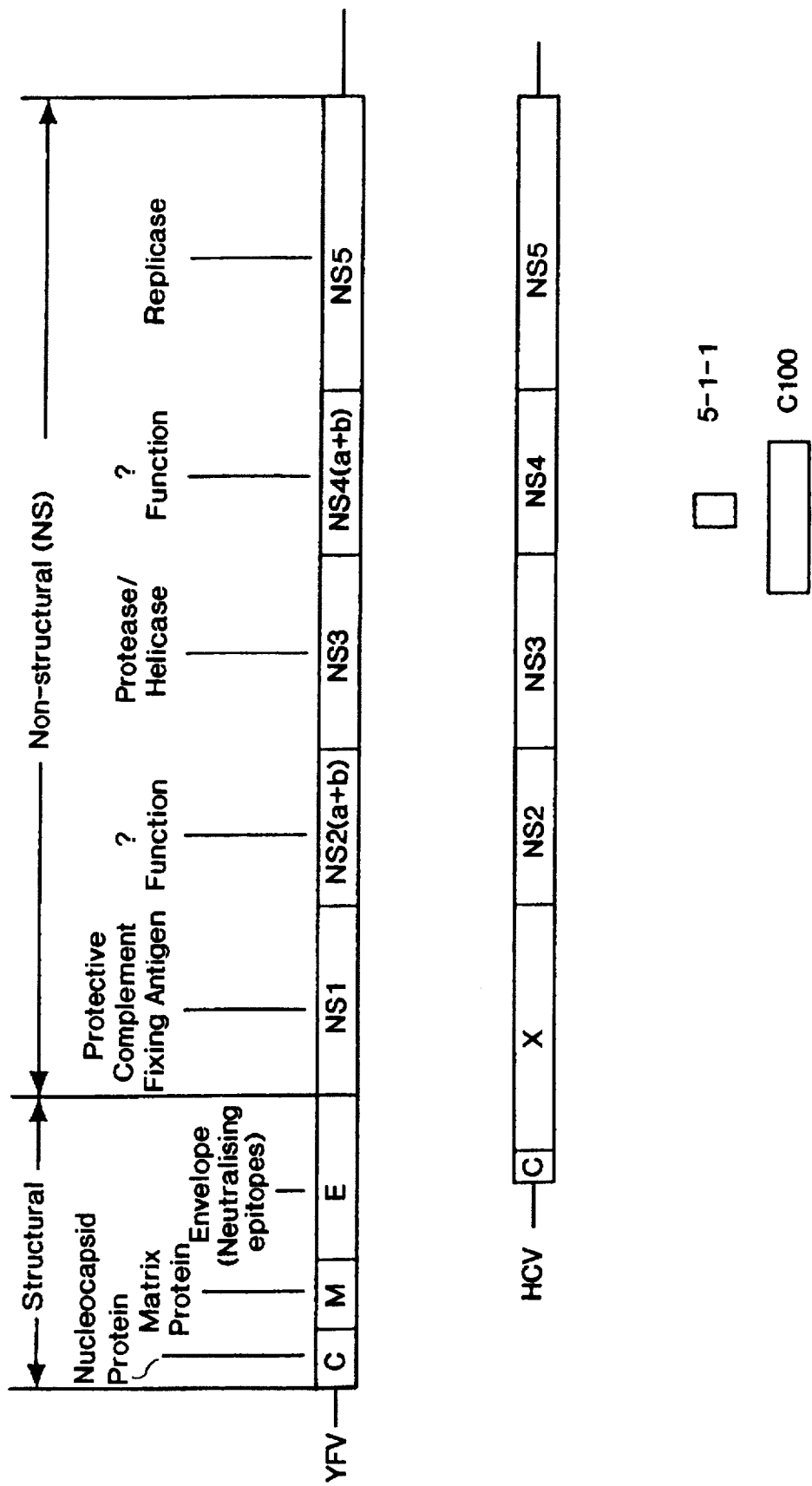
FIG. 3 shows schematic alignment of a flaviviral polyprotein and a putative HCV polyprotein encoded in the major ORF of the HCV genome. Also indicated in the figure are the possible functions of the flaviviral polypeptides cleaved from the flaviral polyprotein. In addition, the relative placements of the HCV polypeptides, $NANB_{5-1-1}$ and C100, with respect to the putative HCV polyprotein are indicated.

The term "hepatitis C virus" (HCV) has been reserved by workers in the field for an heretofore unknown etiologic agent of NANBH. The prototype isolate of HCV has been identified in U.S. Ser. No. 122,714, now abandoned (See also E.P.O. Publication No. 318,216). The term HCV also includes new isolates of the same viral species. As an extension of this terminology, the disease caused by HCV, formerly called blood-borne NANB hepatitis (BB-NANBH), is called hepatitis C. The terms NANBH and hepatitis C may be used interchangeably herein.

HCV is a viral species of which pathogenic strains cause BB-NANBH. There may also be attenuated strains or defective interfering particles derived therefrom. As shown infra, the HCV genome is comprised of RNA. It is known that RNA containing viruses have relatively high rates of spontaneous mutation, i.e., reportedly on the order of $10^{-3}$ to $10^{-4}$ per incorporated nucleotide (Fields & Knipe (1986)). Therefore, since heterogeneity and fluidity of genotype are inherent in RNA viruses, there are multiple strains/isolates, which may be virulent or avirulent, within the HCV species. The compositions and methods described herein, enable the propagation, identification, detection, and isolation of the various HCV strains or isolates.

Several different strains/isolates of HCV have been identified (See U.S. Pat. No. 5,350,671). One such strain or isolate, which is a prototype, is named CDC/HCV1 (also called HCV1). Information from one strain or isolate, such as a partial genomic sequence, is sufficient to allow those skilled in the art using standard techniques to isolate new strains/isolates and to identify whether such new strains/isolates are HCV. For example, several different strains/isolates are described infra. These strains, which were obtained from a number of human sera (and from different geographical areas), were isolated utilizing the information from the genomic sequence of HCV1.

Using the techniques described in U.S. Pat. No. 5,350,671 and infra, the genomic structure and the nucleotide sequence of HCV1 genomic RNA has been deduced. The genome appears to be single-stranded RNA containing ~10,000 nucleotides. The genome is positive-stranded, and possesses a continuous, translational open reading frame (ORF) that encodes a polyprotein of about 3,000 amino acids. In the ORF, the structural protein(s) appear to be encoded in approximately the first quarter of the N-terminus region, with the majority of the polyprotein responsible for non-structural proteins. When compared with all known viral sequences, small but significant co-linear homologies are observed with the non-structural proteins of the flavivirus family, and with the pestiviruses (which are now also considered to be part of the Flavirus family).

A schematic alignment of possible regions of a flaviviral polyprotein (using Yellow Fever Virus as an example), and of a putative polyprotein encoded in the major ORF of the HCV genome, is shown in FIG. 3. In the figure the possible domains of the HCV polyprotein are indicated. The flavivirus polyprotein contains, from the amino terminus to the carboxy terminus, the nucleocapsid protein (C), the matrix protein (M), the envelope protein (E), and the non-structural proteins (NS) 1, 2 (a+b), 3, 4 (a+b), and 5. Based upon the putative amino acids encoded in the nucleotide sequence of HCV1, a small domain at the extreme N-terminus of the HCV polyprotein appears similar both in size and high content of basic residues to the nucleocapsid protein (C) found at the N-terminus of flaviviral polyproteins. The non-structural proteins 2, 3, 4, and 5 (NS2-5) of HCV and of yellow fever virus (YFV) appear to have counter parts of similar size and hydropathicity, although there is divergence of the amino acid sequences. However, the region of HCV which would correspond to the regions of YFV polyprotein which contains the M, E, and NS1 protein not only differs in sequence, but also appears to be quite different both in size and hydropathicity. Thus, while certain domains of the HCV genome may be referred to herein as, for example, NS1, or NS2, it should be borne in mind that these designations are speculative; there may be considerable differences between the HCV family and flaviviruses that have yet to be appreciated.

Different strains, isolates or subtypes of HCV are expected to contain variations at the amino acid and nucleic acids compared with HCV1. Many isolates are expected to show much (i.e., more than about 40%) homology in the total amino acid sequence compared with HCV1. However, it may also be found that there are other less homologous HCV isolates. These would be defined as HCV according to various criteria such as, for example, an ORF of approximately 9,000 nucleotides to approximately 12,000 nucleotides, encoding a polyprotein similar in size to that of HCV1, an encoded polyprotein of similar hydrophobic and/or antigenic character to that of HCV1, and the presence of co-linear peptide sequences that are conserved with HCV1. In addition, it is believed that the genome would be a positive-stranded RNA.

All HCV isolates encode at least one epitope which is immunologically identifiable (i.e., immunologically cross-reactive) with an epitope encoded in the HCV cDNAs described herein. Preferably the epitope is contained in an amino acid sequence described herein and is unique to HCV when compared to previously known pathogens. The uniqueness of the epitope may be determined by its immunological reactivity with anti-HCV antibodies and lack of immunological reactivity with antibodies to known pathogens.

HCV strains and isolates are evolutionarily related. Therefore, it is expected that the overall homology of the genomes at the nucleotide level may be about 40% or greater, probably will be about 50% or greater, probably about 60% or greater, and even more probably about 80% or greater; and in addition that there will be corresponding contiguous sequences of at least about 13 nucleotides. It should be noted, as shown infra, that there are variable and hypervariable regions within the HCV genome; therefore, the homology in these regions is expected to be significantly less than that in the overall genome. The correspondence between the putative HCV strain genomic sequence and, for example, the CDC/HCV1 cDNA sequence can be determined by techniques known in the art. For example, they can be determined by a direct comparison of the sequence information of the polynucleotide from the putative HCV, and the HCV cDNA sequence(s) described herein. They also can be determined by hybridization of the polynucleotides under conditions which form stable duplexes between homologous regions (for example, those which would be used prior to $S_1$ digestion), followed by digestion with single stranded specific nuclease(s), followed by size determination of the digested fragments.

Because of the evolutionary relationship of the strains or isolates of HCV, putative HCV strains or isolates are identifiable by their homology at the polypeptide level. Generally, HCV strains or isolates are expected to be at least 40% homologous, more than about 50% homologous, probably more than about 70% homologous, and even more probably more than about 80% homologous, and some may even be more than about 90% homologous at the polypeptide level. The techniques for determining amino acid sequence homology are known in the art. For example, the amino acid sequence may be determined directly and compared to the sequences provided herein. Alternatively the nucleotide sequence of the genomic material of the putative HCV may be determined (usually via a cDNA intermediate), the putative amino acid sequence encoded therein can be determined, and the corresponding regions compared.

As used herein, a polynucleotide "derived from" a designated sequence refers to a polynucleotide sequence which is comprised of a sequence of approximately at least about 6 nucleotides, preferably at least about 8 nucleotides, more preferably at least about 10–12 nucleotides, and even more preferably at least about 15–20 nucleotides corresponding to a region of the designated nucleotide sequence. "Corresponding" means homologous to or complementary to the designated sequence. Preferably, the sequence of the region from which the polynucleotide is derived is homologous to or complementary to a sequence which is unique to an HCV genome. More preferably, the derived sequence is homologous or complementary to a sequence that is unique to all or to a majority of HCV isolates. Whether or not a sequence is unique to the HCV genome can be determined by techniques known to those of skill in the art. For example, the sequence can be compared to sequences in databanks, e.g., Genebank, to determine whether it is present in the uninfected host or other organisms. The sequence can also be compared to the known sequences of other viral agents, including those which are known to induce hepatitis, e.g., HAV, HBV, and HDV, and to members of the Flaviviridae. The correspondence or non-correspondence of the derived sequence to other sequences can also be determined by hybridization under the appropriate stringency conditions. Hybridization techniques for determining the complementarity of nucleic acid sequences are known in the art, and are discussed infra. See also, for example, Maniatis et al. (1982). In addition, mismatches of duplex polynucleotides formed by hybridization can be determined by known techniques, including for example, digestion with a nuclease such as S1 that specifically digests single-stranded areas in duplex polynucleotides. Regions from which typical DNA sequences may be "derived" include but are not limited to, for example, regions encoding specific epitopes, as well as non-transcribed and/or non-translated regions.

The derived polynucleotide is not necessarily physically derived from the nucleotide sequence shown, but may be generated in any manner, including for example, chemical synthesis or DNA replication or reverse transcription or transcription. In addition, combinations of regions corresponding to that of the designated sequence may be modified in ways known in the art to be consistent with an intended use.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA and RNA. It also includes known types of modifications, for examples, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

As used herein, the "sense strand" of a nucleic acid contains the sequence that has sequence homology to that of mRNA. The "anti-sense strand" contains a sequence which is complementary to that of the "sense strand".

As used herein, a "positive stranded genome" of a virus is one in which the genome, whether RNA or DNA, is single-stranded and which encodes a viral polypeptide(s). Examples of positive stranded RNA viruses include Togaviridae, Coronaviridae, Retroviridae, Picornaviridae, and Caliciviridae. Included also, are the Flaviviridae, which were formerly classified as Togaviradae. See Fields & Knipe (1986).

The term "primer" as used herein refers to an oligomer which is capable of acting as a point of initiation of synthesis of a polynucleotide strand when placed under appropriate conditions. The primer will be completely or substantially complementary to a region of the polynucleotide strand to be copied. Thus, under conditions conducive to hybridization, the primer will anneal to the complementary region of the analyte strand. Upon addition of suitable reactants, (e.g., a polymerase, nucleotide triphosphates, and the like), the primer is extended by the polymerizing agent to form a copy of the analyte strand. The primer may be single-stranded, or alternatively may be partially or fully double-stranded.

The terms "analyte polynucleotide" and "analyte strand" refer to a single- or double-stranded nucleic acid molecule which is suspected of containing a target sequence, and which may be present in a biological sample.

As used herein, the term "oligomer" refers to primers and to probes. The term oligomer does not connote the size of the molecule. However, typically oligomers are no greater than 1000 nucleotides, more typically are no greater than 500 nucleotides, even more typically are no greater than 250 nucleotides; they may be no greater than 100 nucleotides, and may be no greater than 75 nucleotides, and also may be no greater than 50 nucleotides in length.

As used herein, the term "probe" refers to a structure comprised of a polynucleotide which forms a hybrid structure with a target sequence, due to complementarity of at least one sequence in the probe with a sequence in the target region. The polynucleotide regions of probes may be composed of DNA, and/or RNA, and/or synthetic nucleotide analogs. Included within probes are "capture probes" and "label probes". Preferably the probe does not contain a sequence complementary to sequence(s) used to prime the polymerase chain reaction (PCR).

As used herein, the term "target region" refers to a region of the nucleic acid which is to be amplified and/or detected. The term "target sequence" refers to a sequence with which a probe or primer will form a stable hybrid under desired conditions.

The term "capture probe" as used herein refers to a polynucleotide comprised of a single-stranded polynucleotide coupled to a binding partner. The single-stranded polynucleotide is comprised of a targeting polynucleotide sequence, which is complementary to a target sequence in a target region to be detected in the analyte polynucleotide. This complementary region is of sufficient length and complementarity to the target sequence to afford a duplex of stability which is sufficient to immobilize the analyte polynucleotide to a solid surface (via the binding partners). The binding partner is specific for a second binding partner; the second binding partner can be bound to the surface of a solid support, or may be linked indirectly via other structures or binding partners to a solid support.

The term "targeting polynucleotide sequence" as used herein, refers to a polynucleotide sequence which is comprised of nucleotides which are complementary to a target nucleotide sequence; the sequence is of sufficient length and complementarity with the target sequence to form a duplex which has sufficient stability for the purpose intended.

The term "binding partner" as used herein refers to a molecule capable of binding a ligand molecule with high specificity, as for example an antigen and an antibody specific therefor. In general, the specific binding partners must bind with sufficient affinity to immobilize the analyte copy/complementary strand duplex (in the case of capture probes) under the isolation conditions. Specific binding partners are known in the art, and include, for example, biotin and avidin or streptavidin, IgG and protein A, the numerous known receptor-ligand couples, and complementary polynucleotide strands. In the case of complementary polynucleotide binding partners, the partners are normally at least about 15 bases in length, and may be at least 40 bases in length; in addition, they have a content of Gs and Cs of at least about 40% and as much as about 60%. The polynucleotides may be composed of DNA, RNA, or synthetic nucleotide analogs.

The term "coupled" as used herein refers to attachment by covalent bonds or by strong non-covalent interactions (e.g., hydrophobic interactions, hydrogen bonds, etc.). Covalent bonds may be, for example, ester, ether, phosphoester, amide, peptide, imide, carbon-sulfur bonds, carbon-phosphorus bonds, and the like.

The term "support" refers to any solid or semisolid surface to which a desired binding partner may be anchored. Suitable supports include glass, plastic, metal, polymer gels, and the like, and may take the form of beads, wells, dipsticks, membranes, and the like.

The term "label" as used herein refers to any atom or moiety which can be used to provide a detectable (preferably quantifiable) signal, and which can be attached to a polynucleotide or polypeptide.

As used herein, the term "label probe" refers to an oligomer which is comprised of targeting polynucleotide sequence, which is complementary to a target sequence to be detected in the analyte polynucleotide. This complementary region is of sufficient length and complementarity to the target sequence to afford a duplex comprised of the "label probe" and the "target sequence" to be detected by the label. The oligomer is coupled to a label either directly, or indirectly via a set of ligand molecules with high specificity for each other. Sets of ligand molecules with high specificity are described supra., and also includes multimers.

The term "multimer", as used herein, refers to linear or branched polymers of the same repeating single-stranded polynucleotide unit or different single-stranded polynucleotide units. At least one of the units has a sequence, length, and composition that permits it to hybridize specifically to a first single-stranded nucleotide sequence of interest, typically an analyte or an oligomer (e.g., a label probe) bound to an analyte. In order to achieve such specificity and stability, this unit will normally be at least about 15 nucleotides in length, typically no more than about 50 nucleotides in length, and preferably about 30 nucleotides in length; moreover, the content of Gs and Cs will normally be at least about 40%, and at most about 60%. In addition to such unit(s), the multimer includes a multiplicity of units that are capable of hybridizing specifically and stably to a second single-stranded nucleotide of interest, typically a labeled polynucleotide or another multimer. These units are generally about the same size and composition as the multimers discussed above. When a multimer is designed to be hybridized to another multimer, the first and second oligonucleotide units are heterogeneous (different), and do not hybridize with each other under the conditions of the selected assay. Thus, multimers may be label probes, or may be ligands which couple the label to the probe.

As used herein, the term "viral RNA", which includes HCV RNA, refers to RNA from the viral genome, fragments thereof, transcripts thereof, and mutant sequences derived therefrom.

As used herein, a "biological sample" refers to a sample of tissue or fluid isolated from an individual, including but not limited to, for example, plasma, serum, spinal fluid, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components).

DESCRIPTION OF THE INVENTION

The practice of the present invention will employ, unless otherwise indicated, conventional techniques of chemistry, molecular biology, microbiology, recombinant DNA, and immunology, which are within the skill of the art. Such techniques are explained fully in the literature. See e.g., Maniatis, Fitsch & Sambrook, MOLECULAR CLONING; A LABORATORY MANUAL (1982); DNA CLONING, VOLUMES I AND II (D. N Glover ed. 1985); OLIGONUCLEOTIDE SYNTHESIS (M. J. Gait ed, 1984); NUCLEIC ACID HYBRIDIZATION (B. D. Hames & S. J. Higgins eds. 1984); the series, METHODS IN ENZYMOLOGY (Academic Press, Inc.), particularly Vol. 154 and Vol. 155 (Wu and Grossman, and Wu, eds., respectively). All patents, patent applications, and publications mentioned herein, both supra and infra, are hereby incorporated herein by reference.

The useful materials and processes of the present invention are made possible by the identification of HCV as the etiologic agent of BB-NANBV, and by the provision of a family of nucleotide sequences isolated from cDNA libraries which contain HCV cDNA sequences. These cDNA libraries were derived from nucleic acid sequences present in the plasma of an HCV-infected chimpanzee. The construction of one of these libraries, the "c" library (ATCC No. 40394), is described in U.S. Pat. No. 5,350,671.

Utilizing the above-described HCV cDNA sequences, as well as that described herein, oligomers can be constructed which are useful as reagents for detecting viral polynucleotides in biological samples. For example, from the sequences it is possible to synthesize DNA oligomers of about 8–10 nucleotides, or larger, which are useful as hybridization probes to detect the presence of HCV RNA in, for example, donated blood, blood fractions, sera of subjects suspected of harboring the virus, or cell culture systems in which the virus is replicating. In addition, the novel oligomers described herein enable further characterization of the HCV genome. Polynucleotide probes and primers derived from these sequences may be used to amplify sequences present in cDNA libraries, and/or to screen cDNA libraries for additional overlapping cDNA sequences, which, in turn, may be used to obtain more overlapping sequences. As indicated infra. and in U.S. Pat. No. 5,350,671, the genome of HCV appears to be RNA comprised primarily of a large open reading frame (ORF) which encodes a large polyprotein.

In addition to the above, the information provided infra allows the identification of additional HCV strains or isolates. The isolation and characterization of the additional HCV strains or isolates may be accomplished by, for example, isolating the nucleic acids from body components which contain viral particles and/or viral RNA, creating cDNA libraries using the oligomers described infra., for screening the libraries for clones containing HCV cDNA sequences described infra., and comparing the HCV cDNAs from the new isolates with the cDNAs described in U.S. Pat. No. 5,350,671 and infra. Strains or isolates which fit within the parameters of HCV, as described in the Definitions section, supra., are readily identifiable. Other methods for identifying HCV strains will be obvious to those of skill in the art, based upon the information provided herein.

Isolation of the HCV cDNA Sequences

The oligomers of the invention contain regions which form hybrid duplex structures with targeted sequences in HCV polynucleotides. The HCV polynucleotide hybridizing regions of the oligomers may be ascertained from the HCV cDNA sequence(s) provided herein, and described in U.S. Pat. No. 5,350,671. A composite of HCV cDNA from HCV1, a prototypic HCV, is shown in FIG. 1. The composite sequence is based upon sequence information derived from a number of HCV cDNA clones, which were isolated from a number of HCV cDNA libraries, including the "c" library present in lambda gt11 (ATCC No. 40394), and from human serum. The HCV cDNA clones were isolated by methods described in U.S. Pat. No. 5,350,671. Briefly, the majority of clones which were isolated contained sequences from the HCV cDNA "c" library which was constructed using pooled serum from a chimpanzee with chronic HCV infection and containing a high titer of the virus, i.e., at least $10^6$ chimp infectious doses/ml (CID/ml). The pooled serum was used to isolate viral particles; nucleic acids isolated from these particles was used as the template in the construction of cDNA libraries to the viral genome. The initial clone, 5-1-1, was obtained by screening the "c" library with serum from infected individuals. After the isolation of the initial clone, the remainder of the sequence was obtained by screening with synthetic polynucleotide probes, the sequences of which were derived from the 5'-region and the 3'-region of the known HCV cDNA sequence(s).

The description of the methods to retrieve the cDNA sequences is mostly of historical interest. The resultant sequences (and their complements) are provided herein, and the sequences, or any portion thereof, could be prepared using synthetic methods, or by a combination of synthetic methods with retrieval of partial sequences using methods similar to those described in U.S. Pat. No. 5,350,671.

Oligomer Probes and Primers

Using as a basis the HCV genome (as illustrated in FIG. 1), and/or preferably conserved regions of the HCV genome, oligomers of approximately 8 nucleotides or more can be prepared which hybridize with the positive strand(s) of HCV RNA or its complement, as well as to HCV cDNAs. These oligomers can serve as probes for the detection (including isolation and/or labeling) of polynucleotides which contain HCV nucleotide sequences, and/or as primers for the transcription and/or replication of targeted HCV sequences. The oligomers contain a targeting polynucleotide sequence, which is comprised of nucleotides which are complementary to a target HCV nucleotide sequence; the sequence is of sufficient length and complementarity with the HCV sequence to form a duplex which has sufficient stability for the purpose intended. For example, if the purpose is the isolation, via immobilization, of an analyte containing a target HCV sequence, the oligomers would contain a polynucleotide region which is of sufficient length and complementarity to the targeted HCV sequence to afford sufficient duplex stability to immobilize the analyte on a solid surface, via its binding to the oligomers, under the isolation conditions. For example, also, if the oligomers are to serve as primers for the transcription and/or replication of target HCV sequences in an analyte polynucleotide, the oligomers would contain a polynucleotide region of sufficient length and complementarity to the targeted HCV sequence to allow the polymerizing agent to continue replication from the primers which are in stable duplex form with the target sequence, under the polymerizing conditions. For example, also, if the oligomers are to be used as label probes, or are to bind to multimers, the targeting polynucleotide region would be of sufficient length and complementarity to form stable hybrid duplex structures with the label probes and/or multimers to allow detection of the duplex. The oligomers may contain a minimum of about 4 contiguous nucleotides which are complementary to targeted HCV sequence; usually the oligomers will contain a minimum of about 8 contiguous nucleotides which are complementary to the targeted HCV sequence, and preferably will contain a minimum of about 14 contiguous nucleotides which are complementary to the targeted HCV sequence.

Suitable HCV nucleotide targeting sequences may be comprised of nucleotides which are complementary nucleotides selected from the following HCV cDNA nucleotides, which are shown in FIG. 1, ($nn_x$ - $nn_y$ denotes from about nucleotide number x to about nucleotide number y)):

$nn_{-340}$ - $nn_{-330}$; $nn_{-330}$ - $nn_{-320}$; $nn_{-320}$ - $nn_{-310}$; $nn_{-310}$ - $nn_{-300}$; $nn_{-300}$ - $nn_{-290}$; $nn_{-290}$ - $nn_{-280}$; $nn_{-280}$ - $nn_{-270}$; $nn_{-270}$ - $nn_{-260}$; $nn_{-260}$ - $nn_{-250}$; $nn_{-250}$ - $nn_{-240}$; $nn_{-240}$ - $nn_{-230}$; $nn_{-230}$ - $nn_{-220}$; $nn_{-220}$ - $nn_{-210}$; $nn_{-210}$ - $nn_{-200}$; $nn_{-200}$ - $nn_{-190}$; $nn_{-190}$ - $nn_{-180}$; $nn_{-180}$ - $nn_{-170}$; $nn_{-170}$ - $nn_{-160}$; $nn_{-160}$ - $nn_{-150}$; $nn_{-150}$ - $nn_{-140}$; $nn_{-140}$ - $nn_{-130}$; $nn_{-130}$ - $nn_{-120}$; $nn_{-120}$ - $nn_{-110}$; $nn_{-110}$ - $nn_{-100}$; $nn_{-100}$ - $nn_{-90}$; $nn_{-90}$ - $nn_{-80}$; $nn_{-80}$ - $nn_{-70}$; $nn_{-70}$ - $nn_{-60}$; $nn_{-60}$ - $nn_{-50}$; $nn_{-50}$ - $nn_{-40}$; $nn_{-40}$ - $nn_{-30}$; $nn_{-30}$ - $nn_{-20}$; $nn_{-20}$ - $nn_{-10}$; $nn_{-10}$ - $nn_1$; $nn_1$ - $nn_{10}$; $nn_{10}$ - $nn_{20}$; $nn_{20}$ - $nn_{30}$; $nn_{30}$ - $nn_{40}$; $nn_{40}$ - $nn_{50}$; $nn_{50}$ - $nn_{60}$; $nn_{60}$ - $nn_{70}$; $nn_{70}$ - $nn_{80}$; $nn_{80}$ - $nn_{90}$; $nn_{90}$ - $nn_{100}$; $nn_{100}$ - $nn_{110}$; $nn_{110}$ - $nn_{120}$; $nn_{120}$ - $nn_{130}$; $nn_{130}$ - $nn_{140}$; $nn_{140}$ - $nn_{150}$; $nn_{150}$ - $nn_{160}$; $nn_{160}$ - $nn_{170}$; $nn_{170}$ - $nn_{180}$; $nn_{180}$ - $nn_{190}$; $nn_{190}$ - $nn_{200}$; $nn_{200}$ - $nn_{210}$; $nn_{210}$ - $nn_{220}$; $nn_{220}$ - $nn_{230}$; $nn_{230}$ - $nn_{240}$; $nn_{240}$ - $nn_{250}$; $nn_{250}$ - $nn_{260}$; $nn_{260}$ - $nn_{270}$; $nn_{270}$ - $nn_{280}$; $nn_{280}$ - $nn_{290}$; $nn_{290}$ - $nn_{300}$; $nn_{300}$ - $nn_{310}$; $nn_{310}$ - $nn_{320}$; $nn_{320}$ - $nn_{330}$; $nn_{330}$ - $nn_{340}$; $nn_{340}$ - $nn_{350}$; $nn_{350}$ - $nn_{360}$; $nn_{360}$ - $nn_{370}$; $nn_{370}$ - $nn_{380}$; $nn_{380}$ - $nn_{390}$; $nn_{390}$ - $nn_{400}$; $nn_{400}$ - $nn_{410}$; $nn_{410}$ - $nn_{420}$; $nn_{420}$ - $nn_{430}$; $nn_{430}$ - $nn_{440}$; $nn_{440}$ - $nn_{450}$; $nn_{450}$ - $nn_{460}$; $nn_{460}$ - $nn_{470}$; $nn_{470}$ - $nn_{480}$; $nn_{480}$ - $nn_{490}$; $nn_{490}$ - $nn_{500}$; $nn_{500}$ - $nn_{510}$; $nn_{510}$ - $nn_{520}$; $nn_{520}$ - $nn_{530}$; $nn_{530}$ - $nn_{540}$; $nn_{540}$ - $nn_{550}$; $nn_{550}$ - $nn_{560}$; $nn_{560}$ - $nn_{570}$; $nn_{570}$ - $nn_{580}$; $nn_{580}$ - $nn_{590}$; $nn_{590}$ - $nn_{600}$; $nn_{600}$ - $nn_{610}$; $nn_{610}$ - $nn_{620}$; $nn_{620}$ - $nn_{630}$; $nn_{630}$ - $nn_{640}$; $nn_{640}$ - $nn_{650}$; $nn_{650}$ - $nn_{660}$; $nn_{660}$ - $nn_{670}$; $nn_{670}$ - $nn_{680}$; $nn_{680}$ - $nn_{690}$; $nn_{690}$ - $nn_{700}$; $nn_{700}$ - $nn_{710}$; $nn_{710}$ - $nn_{720}$; $nn_{720}$ - $nn_{730}$; $nn_{730}$ - $nn_{740}$; $nn_{740}$ - $nn_{750}$; $nn_{750}$ - $nn_{760}$; $nn_{760}$ - $nn_{770}$; $nn_{770}$ - $nn_{780}$; $nn_{780}$ - $nn_{790}$; $nn_{790}$ - $nn_{800}$; $nn_{800}$ - $nn_{810}$; $nn_{810}$ - $nn_{820}$; $nn_{820}$ - $nn_{830}$; $nn_{830}$ - $nn_{840}$; $nn_{840}$ - $nn_{850}$; $nn_{850}$ - $nn_{860}$; $nn_{860}$ - $nn_{870}$; $nn_{870}$ - $nn_{880}$; $nn_{880}$ - $nn_{890}$; $nn_{890}$ - $nn_{900}$; $nn_{900}$ - $nn_{910}$; $nn_{910}$ - $nn_{920}$; $nn_{920}$ - $nn_{930}$; $nn_{930}$ - $nn_{940}$; $nn_{940}$ - $nn_{950}$; $nn_{950}$ - $nn_{960}$; $nn_{960}$ - $nn_{970}$; $nn_{970}$ - $nn_{980}$; $nn_{980}$ - $nn_{990}$; $nn_{990}$ - $nn_{1000}$; $nn_{1000}$ - $nn_{1010}$; $nn_{1010}$ - $nn_{1020}$; $nn_{1020}$ - $nn_{1030}$; $nn_{1030}$ - $nn_{1040}$; $nn_{1040}$ - $nn_{1050}$; $nn_{1050}$ - $nn_{1060}$; $nn_{1060}$ - $nn_{1070}$; $nn_{1070}$ - $nn_{1080}$; $nn_{1080}$ - $nn_{1090}$; $nn_{1090}$ - $nn_{1100}$; $nn_{1100}$ -

$nn_{1110}$; $nn_{1110}$ - $nn_{1120}$; $nn_{1120}$ - $nn_{1130}$; $nn_{1130}$ - $nn_{1140}$; $nn_{1140}$ - $nn_{1150}$; $nn_{1150}$ - $nn_{1160}$; $nn_{1160}$ - $nn_{1170}$; $nn_{1170}$ - $nn_{1180}$; $nn_{1180}$ - $nn_{1190}$; $nn_{1190}$ - $nn_{1200}$; $nn_{1200}$ - $nn_{1210}$; $nn_{1210}$ - $nn_{1220}$; $nn_{1220}$ - $nn_{1230}$; $nn_{1230}$ - $nn_{1240}$; $nn_{1240}$ - $nn_{1250}$; $nn_{1250}$ - $nn_{1260}$; $nn_{1260}$ - $nn_{1270}$; $nn_{1270}$ - $nn_{1280}$; $nn_{1280}$ - $nn_{1290}$; $nn_{1290}$ - $nn_{1300}$; $nn_{1300}$ - $nn_{1310}$; $nn_{1310}$ - $nn_{1320}$; $nn_{1320}$ - $nn_{1330}$; $nn_{1330}$ - $nn_{1340}$; $nn_{1340}$ - $nn_{1350}$; $nn_{1350}$ - $nn_{1360}$; $nn_{1360}$ - $nn_{1370}$; $nn_{1370}$ - $nn_{1380}$; $nn_{1380}$ - $nn_{1390}$; $nn_{1390}$ - $nn_{1400}$; $nn_{1400}$ - $nn_{1410}$; $nn_{1410}$ - $nn_{1420}$; $nn_{1420}$ - $nn_{1430}$; $nn_{1430}$ - $nn_{1440}$; $nn_{1440}$ - $nn_{1450}$; $nn_{1450}$ - $nn_{1460}$; $nn_{1460}$ - $nn_{1470}$; $nn_{1470}$ - $nn_{1480}$; $nn_{1480}$ - $nn_{1490}$; $nn_{1490}$ - $nn_{1500}$; $nn_{1500}$ - $nn_{1510}$; $nn_{1510}$ - $nn_{1520}$; $nn_{1520}$ - $nn_{1530}$; $nn_{1530}$ - $nn_{1540}$; $nn_{1540}$ - $nn_{1550}$; $nn_{1550}$ - $nn_{1560}$; $nn_{1560}$ - $nn_{1570}$; $nn_{1570}$ - $nn_{1580}$; $nn_{1580}$ - $nn_{1590}$; $nn_{1590}$ - $nn_{1600}$; $nn_{1600}$ - $nn_{1610}$; $nn_{1610}$ - $nn_{1620}$; $nn_{1620}$ - $nn_{1630}$; $nn_{1630}$ - $nn_{1640}$; $nn_{1640}$ - $nn_{1650}$; $nn_{1650}$ - $nn_{1660}$; $nn_{1660}$ - $nn_{1670}$; $nn_{1670}$ - $nn_{1680}$; $nn_{1680}$ - $nn_{1690}$; $nn_{1690}$ - $nn_{1700}$; $nn_{1700}$ - $nn_{1710}$; $nn_{1710}$ - $nn_{1720}$; $nn_{1720}$ - $nn_{1730}$; $nn_{1730}$ - $nn_{1740}$; $nn_{1740}$ - $nn_{1750}$; $nn_{1750}$ - $nn_{1760}$; $nn_{1760}$ - $nn_{1770}$; $nn_{1770}$ - $nn_{1780}$; $nn_{1780}$ - $nn_{1790}$; $nn_{1790}$ - $nn_{1800}$; $nn_{1800}$ - $nn_{1810}$; $nn_{1810}$ - $nn_{1820}$; $nn_{1820}$ - $nn_{1830}$; $nn_{1830}$ - $nn_{1840}$; $nn_{1840}$ - $nn_{1850}$; $nn_{1850}$ - $nn_{1860}$; $nn_{1860}$ - $nn_{1870}$; $nn_{1870}$ - $nn_{1880}$; $nn_{1880}$ - $nn_{1890}$; $nn_{1890}$ - $nn_{1900}$; $nn_{1900}$ - $nn_{1910}$; $nn_{1910}$ - $nn_{1920}$; $nn_{1920}$ - $nn_{1930}$; $nn_{1930}$ - $nn_{1940}$; $nn_{1940}$ - $nn_{1950}$; $nn_{1950}$ - $nn_{1960}$; $nn_{1960}$ - $nn_{1970}$; $nn_{1970}$ - $nn_{1980}$; $nn_{1980}$ - $nn_{1990}$; $nn_{1990}$ - $nn_{2000}$; $nn_{2000}$ - $nn_{2010}$; $nn_{2010}$ - $nn_{2020}$; $nn_{2020}$ - $nn_{2030}$; $nn_{2030}$ - $nn_{2040}$; $nn_{2040}$ - $nn_{2050}$; $nn_{2050}$ - $nn_{2060}$; $nn_{2060}$ - $nn_{2070}$; $nn_{2070}$ - $nn_{2080}$; $nn_{2080}$ - $nn_{2090}$; $nn_{2090}$ - $nn_{2100}$; $nn_{2100}$ - $nn_{2110}$; $nn_{2110}$ - $nn_{2120}$; $nn_{2120}$ - $nn_{2130}$; $nn_{2130}$ - $nn_{2140}$; $nn_{2140}$ - $nn_{2150}$; $nn_{2150}$ - $nn_{2160}$; $nn_{2160}$ - $nn_{2170}$; $nn_{2170}$ - $nn_{2180}$; $nn_{2180}$ - $nn_{2190}$; $nn_{2190}$ - $nn_{2200}$; $nn_{2200}$ - $nn_{2210}$; $nn_{2210}$ - $nn_{2220}$; $nn_{2220}$ - $nn_{2230}$; $nn_{2230}$ - $nn_{2240}$; $nn_{2240}$ - $nn_{2250}$; $nn_{2250}$ - $nn_{2260}$; $nn_{2260}$ - $nn_{2270}$; $nn_{2270}$ - $nn_{2280}$; $nn_{2280}$ - $nn_{2290}$; $nn_{2290}$ - $nn_{2300}$; $nn_{2300}$ - $nn_{2310}$; $nn_{2310}$ - $nn_{2320}$; $nn_{2320}$ - $nn_{2330}$; $nn_{2330}$ - $nn_{2340}$; $nn_{2340}$ - $nn_{2350}$; $nn_{2350}$ - $nn_{2360}$; $nn_{2360}$ - $nn_{2370}$; $nn_{2370}$ - $nn_{2380}$; $nn_{2380}$ - $nn_{2390}$; $nn_{2390}$ - $nn_{2400}$; $nn_{2400}$ - $nn_{2410}$; $nn_{2410}$ - $nn_{2420}$; $nn_{2420}$ - $nn_{2430}$; $nn_{2430}$ - $nn_{2440}$; $nn_{2440}$ - $nn_{2450}$; $nn_{2450}$ - $nn_{2460}$; $nn_{2460}$ - $nn_{2470}$; $nn_{2470}$ - $nn_{2480}$; $nn_{2480}$ - $nn_{2490}$; $nn_{2490}$ - $nn_{2500}$; $nn_{2500}$ - $nn_{2510}$; $nn_{2510}$ - $nn_{2520}$; $nn_{2520}$ - $nn_{2530}$; $nn_{2530}$ - $nn_{2540}$; $nn_{2540}$ - $nn_{2550}$; $nn_{2550}$ - $nn_{2560}$; $nn_{2560}$ - $nn_{2570}$; $nn_{2570}$ - $nn_{2580}$; $nn_{2580}$ - $nn_{2590}$; $nn_{2590}$ - $nn_{2600}$; $nn_{2600}$ - $nn_{2610}$; $nn_{2610}$ - $nn_{2620}$; $nn_{2620}$ - $nn_{2630}$; $nn_{2630}$ - $nn_{2640}$; $nn_{2640}$ - $nn_{2650}$; $nn_{2650}$ - $nn_{2660}$; $nn_{2660}$ - $nn_{2670}$; $nn_{2670}$ - $nn_{2680}$; $nn_{2680}$ - $nn_{2690}$; $nn_{2690}$ - $nn_{2700}$; $nn_{2700}$ - $nn_{2710}$; $nn_{2710}$ - $nn_{2720}$; $nn_{2720}$ - $nn_{2730}$; $nn_{2730}$ - $nn_{2740}$; $nn_{2740}$ - $nn_{2750}$; $nn_{2750}$ - $nn_{2760}$; $nn_{2760}$ - $nn_{2770}$; $nn_{2770}$ - $nn_{2780}$; $nn_{2780}$ - $nn_{2790}$; $nn_{2790}$ - $nn_{2800}$; $nn_{2800}$ - $nn_{2810}$; $nn_{2810}$ - $nn_{2820}$; $nn_{2820}$ - $nn_{2830}$; $nn_{2830}$ - $nn_{2840}$; $nn_{2840}$ - $nn_{2850}$; $nn_{2850}$ - $nn_{2860}$; $nn_{2860}$ - $nn_{2870}$; $nn_{2870}$ - $nn_{2880}$; $nn_{2880}$ - $nn_{2890}$; $nn_{2890}$ - $nn_{2900}$; $nn_{2900}$ - $nn_{2910}$; $nn_{2910}$ - $nn_{2920}$; $nn_{2920}$ - $nn_{2930}$; $nn_{2930}$ - $nn_{2940}$; $nn_{2940}$ - $nn_{2950}$; $nn_{2950}$ - $nn_{2960}$; $nn_{2960}$ - $nn_{2970}$; $nn_{2970}$ - $nn_{2980}$; $nn_{2980}$ - $nn_{2990}$; $nn_{2990}$ - $nn_{3000}$; $nn_{3000}$ - $nn_{3010}$; $nn_{3010}$ - $nn_{3020}$; $nn_{3020}$ - $nn_{3030}$; $nn_{3030}$ - $nn_{3040}$; $nn_{3040}$ - $nn_{3050}$; $nn_{3050}$ - $nn_{3060}$; $nn_{3060}$ - $nn_{3070}$; $nn_{3070}$ - $nn_{3080}$; $nn_{3080}$ - $nn_{3090}$; $nn_{3090}$ - $nn_{3100}$; $nn_{3100}$ - $nn_{3110}$; $nn_{3110}$ - $nn_{3120}$; $nn_{3120}$ - $nn_{3130}$; $nn_{3130}$ - $nn_{3140}$; $nn_{3140}$ - $nn_{3150}$; $nn_{3150}$ - $nn_{3160}$; $nn_{3160}$ - $nn_{3170}$; $nn_{3170}$ - $nn_{3180}$; $nn_{3180}$ - $nn_{3190}$; $nn_{3190}$ - $nn_{3200}$; $nn_{3200}$ - $nn_{3210}$; $nn_{3210}$ - $nn_{3220}$; $nn_{3220}$ - $nn_{3230}$; $nn_{3230}$ - $nn_{3240}$; $nn_{3240}$ - $nn_{3250}$; $nn_{3250}$ - $nn_{3260}$; $nn_{3260}$ - $nn_{3270}$; $nn_{3270}$ - $nn_{3280}$; $nn_{3280}$ - $nn_{3290}$; $nn_{3290}$ - $nn_{3300}$; $nn_{3300}$ - $nn_{3310}$; $nn_{3310}$ - $nn_{3320}$; $nn_{3320}$ - $nn_{3330}$; $nn_{3330}$ - $nn_{3340}$; $nn_{3340}$ - $nn_{3350}$; $nn_{3350}$ - $nn_{3360}$; $nn_{3360}$ - $nn_{3370}$; $nn_{3370}$ - $nn_{3380}$; $nn_{3380}$ - $nn_{3390}$; $nn_{3390}$ - $nn_{3400}$; $nn_{3400}$ - $nn_{3410}$; $nn_{3410}$ - $nn_{3420}$; $nn_{3420}$ - $nn_{3430}$; $nn_{3430}$ - $nn_{3440}$; $nn_{3440}$ - $nn_{3450}$; $nn_{3450}$ - $nn_{3460}$; $nn_{3460}$ - $nn_{3470}$; $nn_{3470}$ - $nn_{3480}$; $nn_{3480}$ - $nn_{3490}$; $nn_{3490}$ - $nn_{3500}$; $nn_{3500}$ - $nn_{3510}$; $nn_{3510}$ - $nn_{3520}$; $nn_{3520}$ - $nn_{3530}$; $nn_{3530}$ - $nn_{3540}$; $nn_{3540}$ - $nn_{3550}$; $nn_{3550}$ - $nn_{3560}$; $nn_{3560}$ - $nn_{3570}$; $nn_{3570}$ - $nn_{3580}$; $nn_{3580}$ - $nn_{3590}$; $nn_{3590}$ - $nn_{3600}$; $nn_{3600}$ - $nn_{3610}$; $nn_{3610}$ - $nn_{3620}$; $nn_{3620}$ - $nn_{3630}$; $nn_{3630}$ - $nn_{3640}$; $nn_{3640}$ - $nn_{3650}$; $nn_{3650}$ - $nn_{3660}$; $nn_{3660}$ - $nn_{3670}$; $nn_{3670}$ - $nn_{3680}$; $nn_{3680}$ - $nn_{3690}$; $nn_{3690}$ - $nn_{3700}$; $nn_{3700}$ - $nn_{3710}$; $nn_{3710}$ - $nn_{3720}$; $nn_{3720}$ - $nn_{3730}$; $nn_{3730}$ - $nn_{3740}$; $nn_{3740}$ - $nn_{3750}$; $nn_{3750}$ - $nn_{3760}$; $nn_{3760}$ - $nn_{3770}$; $nn_{3770}$ - $nn_{3780}$; $nn_{3780}$ - $nn_{3790}$; $nn_{3790}$ - $nn_{3800}$; $nn_{3800}$ - $nn_{3810}$; $nn_{3810}$ - $nn_{3820}$; $nn_{3820}$ - $nn_{3830}$; $nn_{3830}$ - $nn_{3840}$; $nn_{3840}$ - $nn_{3850}$; $nn_{3850}$ - $nn_{3860}$; $nn_{3860}$ - $nn_{3870}$; $nn_{3870}$ - $nn_{3880}$; $nn_{3880}$ - $nn_{3890}$; $nn_{3890}$ - $nn_{3900}$; $nn_{3900}$ - $nn_{3910}$; $nn_{3910}$ - $nn_{3920}$; $nn_{3920}$ - $nn_{3930}$; $nn_{3930}$ - $nn_{3940}$; $nn_{3940}$ - $nn_{3950}$; $nn_{3950}$ - $nn_{3960}$; $nn_{3960}$ - $nn_{3970}$; $nn_{3970}$ - $nn_{3980}$; $nn_{3980}$ - $nn_{3990}$; $nn_{3990}$ - $nn_{4000}$; $nn_{4000}$ - $nn_{4010}$; $nn_{4010}$ - $nn_{4020}$; $nn_{4020}$ - $nn_{4030}$; $nn_{4030}$ - $nn_{4040}$; $nn_{4040}$ - $nn_{4050}$; $nn_{4050}$ - $nn_{4060}$; $nn_{4060}$ - $nn_{4070}$; $nn_{4070}$ - $nn_{4080}$; $nn_{4080}$ - $nn_{4090}$; $nn_{4090}$ - $nn_{4100}$; $nn_{4100}$ - $nn_{4110}$; $nn_{4110}$ - $nn_{4120}$; $nn_{4120}$ - $nn_{4130}$; $nn_{4130}$ - $nn_{4140}$; $nn_{4140}$ - $nn_{4150}$; $nn_{4150}$ - $nn_{4160}$; $nn_{4160}$ - $nn_{4170}$; $nn_{4170}$ - $nn_{4180}$; $nn_{4180}$ - $nn_{4190}$; $nn_{4190}$ - $nn_{4200}$; $nn_{4200}$ - $nn_{4210}$; $nn_{4210}$ - $nn_{4220}$; $nn_{4220}$ - $nn_{4230}$; $nn_{4230}$ - $nn_{4240}$; $nn_{4240}$ - $nn_{4250}$; $nn_{4250}$ - $nn_{4260}$; $nn_{4260}$ - $nn_{4270}$; $nn_{4270}$ - $nn_{4280}$; $nn_{4280}$ - $nn_{4290}$; $nn_{4290}$ - $nn_{4300}$; $nn_{4300}$ - $nn_{4310}$; $nn_{4310}$ - $nn_{4320}$; $nn_{4320}$ - $nn_{4330}$; $nn_{4330}$ - $nn_{4340}$; $nn_{4340}$ - $nn_{4350}$; $nn_{4350}$ - $nn_{4360}$; $nn_{4360}$ - $nn_{4370}$; $nn_{4370}$ - $nn_{4380}$; $nn_{4380}$ - $nn_{4390}$; $nn_{4390}$ - $nn_{4400}$; $nn_{4400}$ - $nn_{4410}$; $nn_{4410}$ - $nn_{4420}$; $nn_{4420}$ - $nn_{4430}$; $nn_{4430}$ - $nn_{4440}$; $nn_{4440}$ - $nn_{4450}$; $nn_{4450}$ - $nn_{4460}$; $nn_{4460}$ - $nn_{4470}$; $nn_{4470}$ - $nn_{4480}$; $nn_{4480}$ - $nn_{4490}$; $nn_{4490}$ - $nn_{4500}$; $nn_{4500}$ - $nn_{4510}$; $nn_{4510}$ - $nn_{4520}$; $nn_{4520}$ - $nn_{4530}$; $nn_{4530}$ - $nn_{4540}$; $nn_{4540}$ - $nn_{4550}$; $nn_{4550}$ - $nn_{4560}$; $nn_{4560}$ - $nn_{4570}$; $nn_{4570}$ - $nn_{4580}$; $nn_{4580}$ - $nn_{4590}$; $nn_{4590}$ - $nn_{4600}$; $nn_{4600}$ - $nn_{4610}$; $nn_{4610}$ - $nn_{4620}$; $nn_{4620}$ - $nn_{4630}$; $nn_{4630}$ - $nn_{4640}$; $nn_{4640}$ - $nn_{4650}$; $nn_{4650}$ - $nn_{4660}$; $nn_{4660}$ - $nn_{4670}$; $nn_{4670}$ - $nn_{4680}$; $nn_{4680}$ - $nn_{4690}$; $nn_{4690}$ - $nn_{4700}$; $nn_{4700}$ - $nn_{4710}$; $nn_{4710}$ - $nn_{4720}$; $nn_{4720}$ - $nn_{4730}$; $nn_{4730}$ - $nn_{4740}$; $nn_{4740}$ - $nn_{4750}$; $nn_{4750}$ - $nn_{4760}$; $nn_{4760}$ - $nn_{4770}$; $nn_{4770}$ - $nn_{4780}$; $nn_{4780}$ - $nn_{4790}$; $nn_{4790}$ - $nn_{4800}$; $nn_{4800}$ - $nn_{4810}$; $nn_{4810}$ - $nn_{4820}$; $nn_{4820}$ - $nn_{4830}$; $nn_{4830}$ - $nn_{4840}$; $nn_{4840}$ - $nn_{4850}$; $nn_{4850}$ - $nn_{4860}$; $nn_{4860}$ - $nn_{4870}$; $nn_{4870}$ - $nn_{4880}$; $nn_{4880}$ - $nn_{4890}$; $nn_{4890}$ - $nn_{4900}$; $nn_{4900}$ - $nn_{4910}$; $nn_{4910}$ - $nn_{4920}$; $nn_{4920}$ - $nn_{4930}$; $nn_{4930}$ - $nn_{4940}$; $nn_{4940}$ - $nn_{4950}$; $nn_{4950}$ - $nn_{4960}$; $nn_{4960}$ - $nn_{4970}$; $nn_{4970}$ - $nn_{4980}$; $nn_{4980}$ - $nn_{4990}$; $nn_{4990}$ - $nn_{5000}$; $nn_{5000}$ - $nn_{5010}$; $nn_{5010}$ - $nn_{5020}$; $nn_{5020}$ - $nn_{5030}$; $nn_{5030}$ - $nn_{5040}$; $nn_{5040}$ - $nn_{5050}$; $nn_{5050}$ - $nn_{5060}$; $nn_{5060}$ - $nn_{5070}$; $nn_{5070}$ - $nn_{5080}$; $nn_{5080}$ - $nn_{5090}$; $nn_{5090}$ - $nn_{5100}$; $nn_{5100}$ - $nn_{5110}$; $nn_{5110}$ - $nn_{5120}$; $nn_{5120}$ - $nn_{5130}$; $nn_{5130}$ - $nn_{5140}$; $nn_{5140}$ - $nn_{5150}$; $nn_{5150}$ - $nn_{5160}$; $nn_{5160}$ - $nn_{5170}$; $nn_{5170}$ - $nn_{5180}$; $nn_{5180}$ - $nn_{5190}$; $nn_{5190}$ - $nn_{5200}$; $nn_{5200}$ - $nn_{5210}$; $nn_{5210}$ - $nn_{5220}$; $nn_{5220}$ - $nn_{5230}$; $nn_{5230}$ - $nn_{5240}$; $nn_{5240}$ - $nn_{5250}$; $nn_{5250}$ - $nn_{5260}$; $nn_{5260}$ - $nn_{5270}$; $nn_{5270}$ - $nn_{5280}$; $nn_{5280}$ - $nn_{5290}$; $nn_{5290}$ - $nn_{5300}$; $nn_{5300}$ - $nn_{5310}$; $nn_{5310}$ - $nn_{5320}$; $nn_{5320}$ - $nn_{5330}$; $nn_{5330}$ - $nn_{5340}$; $nn_{5340}$ - $nn_{5350}$; $nn_{5350}$ - $nn_{5360}$; $nn_{5360}$ - $nn_{5370}$; $nn_{5370}$ - $nn_{5380}$; $nn_{5380}$ - $nn_{5390}$; $nn_{5390}$ - $nn_{5400}$; $nn_{5400}$ - $nn_{5410}$; $nn_{5410}$ - $nn_{5420}$; $nn_{5420}$ - $nn_{5430}$; $nn_{5430}$ - $nn_{5440}$; $nn_{5440}$ - $nn_{5450}$; $nn_{5450}$ - $nn_{5460}$; $nn_{5460}$ - $nn_{5470}$; $nn_{5470}$ - $nn_{5480}$; $nn_{5480}$ - $nn_{5490}$; $nn_{5490}$ - $nn_{5500}$; $nn_{5500}$ - $nn_{5510}$; $nn_{5510}$ - $nn_{5520}$; $nn_{5520}$ - $nn_{5530}$; $nn_{5530}$ - $nn_{5540}$; $nn_{5540}$ - $nn_{5550}$; $nn_{5550}$ - $nn_{5560}$; $nn_{5560}$ - $nn_{5570}$; $nn_{5570}$ - $nn_{5580}$; $nn_{5580}$ - $nn_{5590}$; $nn_{5590}$ - $nn_{5600}$; $nn_{5600}$ - $nn_{5610}$; $nn_{5610}$ - $nn_{5620}$; $nn_{5620}$ - $nn_{5630}$; $nn_{5630}$ - $nn_{5640}$; $nn_{5640}$ - $nn_{5650}$; $nn_{5650}$ - $nn_{5660}$; $nn_{5660}$ - $nn_{5670}$; $nn_{5670}$ - $nn_{5680}$; $nn_{5680}$ - $nn_{5690}$; $nn_{5690}$ - $nn_{5700}$; $nn_{5700}$ - $nn_{5710}$; $nn_{5710}$ - $nn_{5720}$; $nn_{5720}$ - $nn_{5730}$; $nn_{5730}$ - $nn_{5740}$; $nn_{5740}$ - $nn_{5750}$; $nn_{5750}$ - $nn_{5760}$; $nn_{5760}$ - $nn_{5770}$; $nn_{5770}$ - $nn_{5780}$; $nn_{5780}$ - $nn_{5790}$; $nn_{5790}$ -

$nn_{5800}$; $nn_{5800} - nn_{5810}$; $nn_{5810} - nn_{5820}$; $nn_{5820} - nn_{5830}$; $nn_{5830} - nn_{5840}$; $nn_{5840} - nn_{5850}$; $nn_{5850} - nn_{5860}$; $nn_{5860} - nn_{5870}$; $nn_{5870} - nn_{5880}$; $nn_{5880} - nn_{5890}$; $nn_{5890} - nn_{5900}$; $nn_{5900} - nn_{5910}$; $nn_{5910} - nn_{5920}$; $nn_{5920} - nn_{5930}$; $nn_{5930} - nn_{5940}$; $nn_{5940} - nn_{5950}$; $nn_{5950} - nn_{5960}$; $nn_{5960} - nn_{5970}$; $nn_{5970} - nn_{5980}$; $nn_{5980} - nn_{5990}$; $nn_{5990} - nn_{6000}$; $nn_{6000} - nn_{6010}$; $nn_{6010} - nn_{6020}$; $nn_{6020} - nn_{6030}$; $nn_{6030} - nn_{6040}$; $nn_{6040} - nn_{6050}$; $nn_{6050} - nn_{6060}$; $nn_{6060} - nn_{6070}$; $nn_{6070} - nn_{6080}$; $nn_{6080} - nn_{6090}$; $nn_{6090} - nn_{6100}$; $nn_{6100} - nn_{6110}$; $nn_{6110} - nn_{6120}$; $nn_{6120} - nn_{6130}$; $nn_{6130} - nn_{6140}$; $nn_{6140} - nn_{6150}$; $nn_{6150} - nn_{6160}$; $nn_{6160} - nn_{6170}$; $nn_{6170} - nn_{6180}$; $nn_{6180} - nn_{6190}$; $nn_{6190} - nn_{6200}$; $nn_{6200} - nn_{6210}$; $nn_{6210} - nn_{6220}$; $nn_{6220} - nn_{6230}$; $nn_{6230} - nn_{6240}$; $nn_{6240} - nn_{6250}$; $nn_{6250} - nn_{6260}$; $nn_{6260} - nn_{6270}$; $nn_{6270} - nn_{6280}$; $nn_{6280} - nn_{6290}$; $nn_{6290} - nn_{6300}$; $nn_{6300} - nn_{6310}$; $nn_{6310} - nn_{6320}$; $nn_{6320} - nn_{6330}$; $nn_{6330} - nn_{6340}$; $nn_{6340} - nn_{6350}$; $nn_{6350} - nn_{6360}$; $nn_{6360} - nn_{6370}$; $nn_{6370} - nn_{6380}$; $nn_{6380} - nn_{6390}$; $nn_{6390} - nn_{6400}$; $nn_{6400} - nn_{6410}$; $nn_{6410} - nn_{6420}$; $nn_{6420} - nn_{6430}$; $nn_{6430} - nn_{6440}$; $nn_{6440} - nn_{6450}$; $nn_{6450} - nn_{6460}$; $nn_{6460} - nn_{6470}$; $nn_{6470} - nn_{6480}$; $nn_{6480} - nn_{6490}$; $nn_{6490} - nn_{6500}$; $nn_{6500} - nn_{6510}$; $nn_{6510} - nn_{6520}$; $nn_{6520} - nn_{6530}$; $nn_{6530} - nn_{6540}$; $nn_{6540} - nn_{6550}$; $nn_{6550} - nn_{6560}$; $nn_{6560} - nn_{6570}$; $nn_{6570} - nn_{6580}$; $nn_{6580} - nn_{6590}$; $nn_{6590} - nn_{6600}$; $nn_{6600} - nn_{6610}$; $nn_{6610} - nn_{6620}$; $nn_{6620} - nn_{6630}$; $nn_{6630} - nn_{6640}$; $nn_{6640} - nn_{6650}$; $nn_{6650} - nn_{6660}$; $nn_{6660} - nn_{6670}$; $nn_{6670} - nn_{6680}$; $nn_{6680} - nn_{6690}$; $nn_{6690} - nn_{6700}$; $nn_{6700} - nn_{6710}$; $nn_{6710} - nn_{6720}$; $nn_{6720} - nn_{6730}$; $nn_{6730} - nn_{6740}$; $nn_{6740} - nn_{6750}$; $nn_{6750} - nn_{6760}$; $nn_{6760} - nn_{6770}$; $nn_{6770} - nn_{6780}$; $nn_{6780} - nn_{6790}$; $nn_{6790} - nn_{6800}$; $nn_{6800} - nn_{6810}$; $nn_{6810} - nn_{6820}$; $nn_{6820} - nn_{6830}$; $nn_{6830} - nn_{6840}$; $nn_{6840} - nn_{6850}$; $nn_{6850} - nn_{6860}$; $nn_{6860} - nn_{6870}$; $nn_{6870} - nn_{6880}$; $nn_{6880} - nn_{6890}$; $nn_{6890} - nn_{6900}$; $nn_{6900} - nn_{6910}$; $nn_{6910} - nn_{6920}$; $nn_{6920} - nn_{6930}$; $nn_{6930} - nn_{6940}$; $nn_{6940} - nn_{6950}$; $nn_{6950} - nn_{6960}$; $nn_{6960} - nn_{6970}$; $nn_{6970} - nn_{6980}$; $nn_{6980} - nn_{6990}$; $nn_{6990} - nn_{7000}$; $nn_{7000} - nn_{7010}$; $nn_{6010} - nn_{7020}$; $nn_{7020} - nn_{7030}$; $nn_{7030} - nn_{7040}$; $nn_{7040} - nn_{7050}$; $nn_{7050} - nn_{7060}$; $nn_{7060} - nn_{7070}$; $nn_{7070} - nn_{7080}$; $nn_{7080} - nn_{7090}$; $nn_{7090} - nn_{7100}$; $nn_{7100} - nn_{7110}$; $nn_{7110} - nn_{7120}$; $nn_{7120} - nn_{7130}$; $nn_{7130} - nn_{7140}$; $nn_{7140} - nn_{7150}$; $nn_{7150} - nn_{7160}$; $nn_{7160} - nn_{7170}$; $nn_{7170} - nn_{7180}$; $nn_{7180} - nn_{7190}$; $nn_{7190} - nn_{7200}$; $nn_{7200} - nn_{7210}$; $nn_{7210} - nn_{7220}$; $nn_{7220} - nn_{7230}$; $nn_{7230} - nn_{7240}$; $nn_{7240} - nn_{7250}$; $nn_{7250} - nn_{7260}$; $nn_{7260} - nn_{7270}$; $nn_{7270} - nn_{7280}$; $nn_{7280} - nn_{7290}$; $nn_{7290} - nn_{7300}$; $nn_{7300} - nn_{7310}$; $nn_{7310} - nn_{7320}$; $nn_{7320} - nn_{7330}$; $nn_{7330} - nn_{7340}$; $nn_{7340} - nn_{7350}$; $nn_{7350} - nn_{7360}$; $nn_{7360} - nn_{7370}$; $nn_{7370} - nn_{7380}$; $nn_{7380} - nn_{7390}$; $nn_{7390} - nn_{7400}$; $nn_{7400} - nn_{7410}$; $nn_{7410} - nn_{7420}$; $nn_{7420} - nn_{7430}$; $nn_{7430} - nn_{7440}$; $nn_{7440} - nn_{7450}$; $nn_{7450} - nn_{7460}$; $nn_{7460} - nn_{7470}$; $nn_{7470} - nn_{7480}$; $nn_{7480} - nn_{7490}$; $nn_{7490} - nn_{7500}$; $nn_{7500} - nn_{7510}$; $nn_{7510} - nn_{7520}$; $nn_{7520} - nn_{7530}$; $nn_{7530} - nn_{7540}$; $nn_{7540} - nn_{7550}$; $nn_{7550} - nn_{7560}$; $nn_{7560} - nn_{7570}$; $nn_{7570} - nn_{7580}$; $nn_{7580} - nn_{7590}$; $nn_{7590} - nn_{7600}$; $nn_{7600} - nn_{7610}$; $nn_{7610} - nn_{7620}$; $nn_{7620} - nn_{7630}$; $nn_{7630} - nn_{7640}$; $nn_{7640} - nn_{7650}$; $nn_{7650} - nn_{7660}$; $nn_{7660} - nn_{7670}$; $nn_{7670} - nn_{7680}$; $nn_{7680} - nn_{7690}$; $nn_{7690} - nn_{7700}$; $nn_{7700} - nn_{7710}$; $nn_{7710} - nn_{7720}$; $nn_{7720} - nn_{7730}$; $nn_{7730} - nn_{7740}$; $nn_{7740} - nn_{7750}$; $nn_{7750} - nn_{7760}$; $nn_{7760} - nn_{7770}$; $nn_{7770} - nn_{7780}$; $nn_{7780} - nn_{7790}$; $nn_{7790} - nn_{7800}$; $nn_{7800} - nn_{7810}$; $nn_{7810} - nn_{7820}$; $nn_{7820} - nn_{7830}$; $nn_{7830} - nn_{7840}$; $nn_{7840} - nn_{7850}$; $nn_{7850} - nn_{7860}$; $nn_{7860} - nn_{7870}$; $nn_{7870} - nn_{7880}$; $nn_{7880} - nn_{7890}$; $nn_{7890} - nn_{7900}$; $nn_{7900} - nn_{7910}$; $nn_{7910} - nn_{7920}$; $nn_{7920} - nn_{7930}$; $nn_{7930} - nn_{7940}$; $nn_{7940} - nn_{7950}$; $nn_{7950} - nn_{7960}$; $nn_{7960} - nn_{7970}$; $nn_{7970} - nn_{7980}$; $nn_{7980} - nn_{7990}$; $nn_{7990} - nn_{8000}$; $nn_{8000} - nn_{8010}$; $nn_{8010} - nn_{8020}$; $nn_{8020} - nn_{8030}$; $nn_{8030} - nn_{8040}$; $nn_{8040} - nn_{8050}$; $nn_{8050} - nn_{8060}$; $nn_{8060} - nn_{8070}$; $nn_{8070} - nn_{8080}$; $nn_{8080} - nn_{8090}$; $nn_{8090} - nn_{8100}$; $nn_{8100} - nn_{8110}$; $nn_{8110} - nn_{8120}$; $nn_{8120} - nn_{8130}$; $nn_{8130} - nn_{8140}$; $nn_{8140} - nn_{8150}$; $nn_{8150} - nn_{8160}$; $nn_{8160} - nn_{8170}$; $nn_{8170} - nn_{8180}$; $nn_{8180} - nn_{8190}$; $nn_{8190} - nn_{8200}$; $nn_{8200} - nn_{8210}$; $nn_{8210} - nn_{8220}$; $nn_{8220} - nn_{8230}$; $nn_{8230} - nn_{8240}$; $nn_{8240} - nn_{8250}$; $nn_{8250} - nn_{8260}$; $nn_{8260} - nn_{8270}$; $nn_{8270} - nn_{8280}$; $nn_{8280} - nn_{8290}$; $nn_{8290} - nn_{8300}$; $nn_{8300} - nn_{8310}$; $nn_{8310} - nn_{8320}$; $nn_{8320} - nn_{8330}$; $nn_{8330} - nn_{8340}$; $nn_{8340} - nn_{8350}$; $nn_{8350} - nn_{8360}$; $nn_{8360} - nn_{8370}$; $nn_{8370} - nn_{8380}$; $nn_{8380} - nn_{8390}$; $nn_{8390} - nn_{8400}$; $nn_{8400} - nn_{8410}$; $nn_{8410} - nn_{8420}$; $nn_{8420} - nn_{8430}$; $nn_{8430} - nn_{8440}$; $nn_{8440} - nn_{8450}$; $nn_{8450} - nn_{8460}$; $nn_{8460} - nn_{8470}$; $nn_{8470} - nn_{8480}$; $nn_{8480} - nn_{8490}$; $nn_{8490} - nn_{8500}$; $nn_{8500} - nn_{8510}$; $nn_{8510} - nn_{8520}$; $nn_{8520} - nn_{8530}$; $nn_{8530} - nn_{8540}$; $nn_{8540} - nn_{8550}$; $nn_{8550} - nn_{8560}$; $nn_{8560} - nn_{8570}$; $nn_{8570} - nn_{8580}$; $nn_{8580} - nn_{8590}$; $nn_{8590} - nn_{8600}$; $nn_{8600} - nn_{8610}$; $nn_{8610} - nn_{8620}$; $nn_{8620} - nn_{8630}$; $nn_{8630} - nn_{8640}$; $nn_{8640} - nn_{8650}$; $nn_{8650} - nn_{8660}$; $nn_{8660} - nn_{8670}$; $nn_{8670} - nn_{8680}$; $nn_{8680} - nn_{8690}$; $nn_{8690} - nn_{8700}$; $nn_{8700} - nn_{8710}$; $nn_{8710} - nn_{8720}$; $nn_{8720} - nn_{8730}$; $nn_{8730} - nn_{8740}$; $nn_{8740} - nn_{8750}$; $nn_{8750} - nn_{8760}$; $nn_{8760} - nn_{8770}$; $nn_{8770} - nn_{8780}$; $nn_{8780} - nn_{8790}$; $nn_{8790} - nn_{8800}$; $nn_{8800} - nn_{8810}$; $nn_{8810} - nn_{8820}$; $nn_{8820} - nn_{8830}$; $nn_{8830} - nn_{8840}$; $nn_{8840} - nn_{8850}$; $nn_{8850} - nn_{8860}$; $nn_{8860} - nn_{8870}$; $nn_{8870} - nn_{8880}$; $nn_{8880} - nn_{8890}$; $nn_{8890} - nn_{8900}$; $nn_{8900} - nn_{8910}$; $nn_{8910} - nn_{8920}$; $nn_{8920} - nn_{8930}$; $nn_{8930} - nn_{8940}$; $nn_{8940} - nn_{8950}$; $nn_{8950} - nn_{8960}$; $nn_{8960} - nn_{8970}$; $nn_{8970} - nn_{8980}$; $nn_{8980} - nn_{8990}$; $nn_{8990} - nn_{9000}$; $nn_{9000} - nn_{9010}$; $nn_{9010} - nn_{9020}$; $nn_{9020} - nn_{9030}$; $nn_{9030} - nn_{9040}$; $nn_{9040} - nn_{9050}$; $nn_{9050} - nn_{9060}$.

The oligomer, however, need not consist only of the sequence which is complementary to the targeted HCV sequence. It may contain in addition, nucleotide sequences or other moieties which are suitable for the purposes for which the oligomers are used. For example, if the oligomers are used as primers for the amplification of HCV sequences via PCR, they may contain sequences which, when in duplex, form restriction enzyme sites which facilitate the cloning of the amplified sequences. For example, also, if the oligomers are to be used as "capture probes" in hybridization assays (described infra), they would contain in addition a binding partner which is coupled to the oligomer containing the nucleotide sequence which is complementary to the targeted HCV sequence. Other types of moieties or sequences which are useful of which the oligomers may be comprised or coupled to, are those which are known in the art to be suitable for a variety of purposes, including the labeling of nucleotide probes.

The preparation of the oligomers is by means known in the art, including, for example, by methods which include excision, transcription, or chemical synthesis. The target sequences and/or regions of the genome which are selected to which the targeting polynucleotides of the oligomers are complementary depend upon the purpose. For example, if the goal is to screen for the presence of HCV in biological samples (e.g. blood), the preferred oligomers would be used as probes and/or primers, and would hybridize to conserved regions of the HCV genome. Some of the conserved regions of the HCV genome to which the oligomers may bind are described herein, for example, the regions which include nucleotide numbers from about the 5-terminus to about 200, or from about 4000 to about 5000, or from about 8000 to about 9040 as shown in FIG. 1, or preferably nucleotides about −318 to about 174, about 4056 to about 4448, and about 4378 to about 4902. Particularly preferred primers and probes are derived from about nucleotides −313 to about −173, and from about nucleotide 1 to about nucleotide 540, as shown in FIG. 1. Other regions of the genome which are conserved are readily ascertainable by comparison of the nucleotide sequences of various isolates of HCV, including the prototype HCV, HCV1. Methods for conducting comparisons between genotypes to determine conserved and non-conserved regions are known in the art, and examples of these methods are disclosed in U.S. Pat. No. 5,350,671, which is incorporated herein by reference.

In the basic nucleic acid hybridization assay, single-stranded analyte nucleic acid (either DNA or RNA) is hybridized to a nucleic acid probe, and resulting duplexes are detected. The probes for HCV polynucleotides (natural or derived) are a length which allows the detection of unique viral sequences by hybridization. While 6–8 nucleotides may be a workable length, sequences of 10–12 nucleotides are preferred, and about 20 nucleotides or more appears optimal. Preferably, these sequences will derive from regions which lack heterogeneity. These probes can be prepared using routine methods, including automated oligonucleotide synthetic methods. Among useful probes, for example, are those derived from the newly isolated clones disclosed herein, as well as the various oligomers useful in probing cDNA libraries, set forth below. A complement to any unique portion of the HCV genome will be satisfactory. For use as probes, complete complementarity is desirable, though it may be unnecessary as the length of the fragment is increased.

For use of such probes as agents to detect the presence of HCV polynucleotides (for example in screening for contaminated blood), the biological sample to be analyzed, such as blood or serum, may be treated, if desired, to extract the nucleic acids contained therein. The resulting nucleic acid from the sample may be subjected to gel electrophoresis or other size separation techniques; alternatively, the nucleic acid sample may be dot blotted without size separation. In order to form hybrid duplexes with the targeting sequence of the probe, the targeted region of the analyte nucleic acid must be in single stranded form. Where the sequence is naturally present in single stranded form, denaturation will not be required. However, where the sequence is present in double stranded form, the sequence will be denatured. Denaturation can be carried out by various techniques known in the art. Subsequent to denaturation, the analyte nucleic acid and probe are incubated under conditions which promote stable hybrid formation of the target sequence in the probe with the putative targeted sequence in the analyte, and the resulting duplexes containing the probe(s) are detected.

Detection of the resulting duplex, if any, is usually accomplished by the use of labeled probes; alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation or kinasing), biotin, fluorescent groups, chemiluminescent groups (e.g., dioxetanes, particularly triggered dioxetanes), enzymes, antibodies, and the like.

The region of the probes which are used to bind to the analyte can be made completely complementary to the HCV genome. Therefore, usually high stringency conditions are desirable in order to prevent false positives. However, conditions of high stringency should only be used if the probes are complementary to regions of the viral genome which lack heterogeneity. The stringency of hybridization is determined by a number of factors during hybridization and during the washing procedure, including temperature, ionic strength, length of time, and concentration of formamide. These factors are outlined in, for example, Maniatis, T. (1982).

Variations of this basic scheme which are known in the art, including those which facilitate separation of the duplexes to be detected from extraneous materials and/or which amplify the signal from the labeled moiety, may also be used. A number of these variations are reviewed in, for example: Matthews and Kricka (1988), Analytical Biochemistry 169:1; Landegren et al. (1988), Science 242:229; and Mittlin (1989), Clinical chem. 35:1819. These and the following publications describing assay formats are hereby incorporated by reference herein. Probes suitable for detecting HCV in these assays are comprised of sequences which hybridize with target HCV polynucleotide sequences to form duplexes with the analyte strand, wherein the duplexes are of sufficient stability for detection in the specified assay system.

A suitable variation is, for example, one which is described in U.S. Pat. No. 4,868,105, issued Sep. 9, 1989, and in EPO Publication No. 225,807 (published Jun. 16, 1987). These publications describe a solution phase nucleic acid hybridization assay in which the analyte nucleic acid is hybridized to a labeling probe set and to a capturing probe set. The probe-analyte complex is coupled by hybridization with a solid-supported capture probe that is complementary to the capture probe set. This permits the analyte nucleic acid to be removed from solution as a solid phase complex. Having the analyte in the form of a solid phase complex facilitates subsequent separation steps in the assay. The labeling probe set is complementary to a labeled probe that is bound through hybridization to the solid phase/analyte complex.

Generally, it is expected that the HCV genome sequences will be present in serum of infected individuals at relatively low levels, i.e., at approximately $10^2$–$10^3$ chimp infectious doses (CID) per ml. This level may require that amplification techniques be used in hybridization assays. Such techniques are known in the art. For example, the Enzo Biochemical Corporation "Bio-Bridge" system uses terminal deoxynucleotide transferase to add unmodified 3'-poly-dT-tails to a DNA probe. The poly dT-tailed probe is hybridized to the target nucleotide sequence, and then to a biotin-modified poly-A. PCT Publication 84/03520 and EP Publication No. 124221 describe a DNA hybridization assay in which: (1) analyte is annealed to a single-stranded DNA probe that is complementary to an enzyme-labeled oligonucleotide; and (2) the resulting tailed duplex is hybridized to an enzyme-labeled oligonucleotide. EPA 204510 describes a DNA hybridization assay in which analyte DNA is contacted with a probe that has a tail, such as a poly-dT tail, an amplifier strand that has a sequence that hybridizes to the tail of the probe, such as a poly-A sequence, and which is capable of binding a plurality of labeled strands. A type of hybridization assay which is described in EPO Publication No. 317,077 (published May 24, 1989), which should detect sequences at the level of approximately $10^6$/ml, utilizes nucleic acid multimers which bind to single-stranded analyte nucleic acid, and which also bind to a multiplicity of single-stranded labeled oligonucleotides. A particularly desirable technique may involve amplification of the target HCV sequences in sera approximately 10,000 fold (i.e., to approximately $10^6$ sequences/ml), as part of the hybridization system. The amplification may be accomplished, for example, by the polymerase chain reactions (PCR) technique described by Saiki et al. (1986), by Mullis, U.S. Pat. No. 4,683,195, and by Mullis et al. U.S. Pat. No. 4,683,202. Amplification may be prior to, or preferably subsequent to purification of the HCV target sequence. For example, amplification may be utilized in conjunction with the assay methods described in U.S. Pat. No. 4,868,105, or if even further amplification is desired, in conjunction with the hybridization system described in EPO Publication No. 317,077.

Preferred methods for detecting HCV sequences in an analyte polynucleotide strand are based upon the hybridization detection methods described in U.S. Pat. No. 4,868,105 and in EPO Publication No. 317,077. These methods are solution-phase sandwich hybridization assays which utilize both capture and label probes which hybridize to target sequences in an analyte nucleic acid. In the use of these assays to screen biological samples for HCV, the probes used would bind to conserved regions of the HCV genome. The capture and label probes may be interspersed in their binding to the target sequence. Alternatively, in a preferred mode the capture and label probes are in sets, and the probes of one set do not intersperse with the probes of another set. In the latter mode, preferably the set(s) of multiple capture probes hybridize to the most conserved regions of the genome, while the set(s) of multiple label probes may hybridize to regions which exhibit small amounts of divergence. For example, using the prototype HCV1 cDNA sequence shown in FIG. 1, probes could be used which hybridize to sequences in the region of nucleotides from about −318 to about 174, and/or nucleotides in the region of about 4378 to about 4902, and/or nucleotides in the region of from about 4056 to about 4448. The preferred probes would hybridize to sequences in the 5'-region of the HCV genome, since, as shown infra., this region appears to be highly conserved. Thus, preferred probes may hybridize to, for example, nucleotides from about −318 to about 174 as shown in FIG. 1. Probes could be used which hybridize to either the positive strand in conserved regions, and/or its complement, depending upon the purpose, for example, to detect viral genomic sequences, or to detect HCV cDNA sequences resulting from PCR amplification, or to detect replicative intermediates to the positive HCV RNA strand. Identification RNA Which Hybridizes to HCV cDNA in Infected Individuals.

A. Identification of RNA in the Liver of HCV-Infected Chimpanzee Which Hybridizes to HCV cDNA.

RNA from the liver of a chimpanzee which had been infected with HCV was shown to contain a species of RNA which hybridized to the HCV cDNA contained within clone 81 by Northern blotting, as follows.

RNA (from a liver biopsy of a chimpanzee from which high titer plasma was derive) was isolated using techniques described in Maniatis et al (1982) for the isolation of total RNA from mammalian cells, and for its separation into poly A+ and poly A− fractions. These RNA fractions were subjected to electrophoresis on a formaldehyde/agarose gel (1% w/v), and transferred to nitrocellulose (Maniatis et al (1982)). The nitrocellulose filters were hybridized with radio-labeled HCV cDNA from clone 81 (see FIG. 5 for the nucleotide sequence of the insert.) To prepare the radio-labeled probe, the HCV cDNA insert isolated from clone 81 was radio-labeled with $^{32}$P by nick translation using DNA Polymerase I (Maniatis el al (1982)). Hybridization was for 18 hours at 42° C. in a solution containing 10% (w/v) Dextran sulphate, 50% (w/v) deionized formamide, 750 mM NaCl, 75 mM Na citrate, 20 mM $Na_2HPO_4$, pH 6.5, 0.1% SDS, 0.02% (w/v) bovine serum albumin (BSA), 0.02% (w/v) Ficoll-400, 0.02% (w/v) polyvinylpyrrolidone, 100 µg/ml salmon sperm DNA which had been sheared by sonication and denatured, and $10^6$ CPM/ml of the nick-translated cDNA probe.

Figure 21:
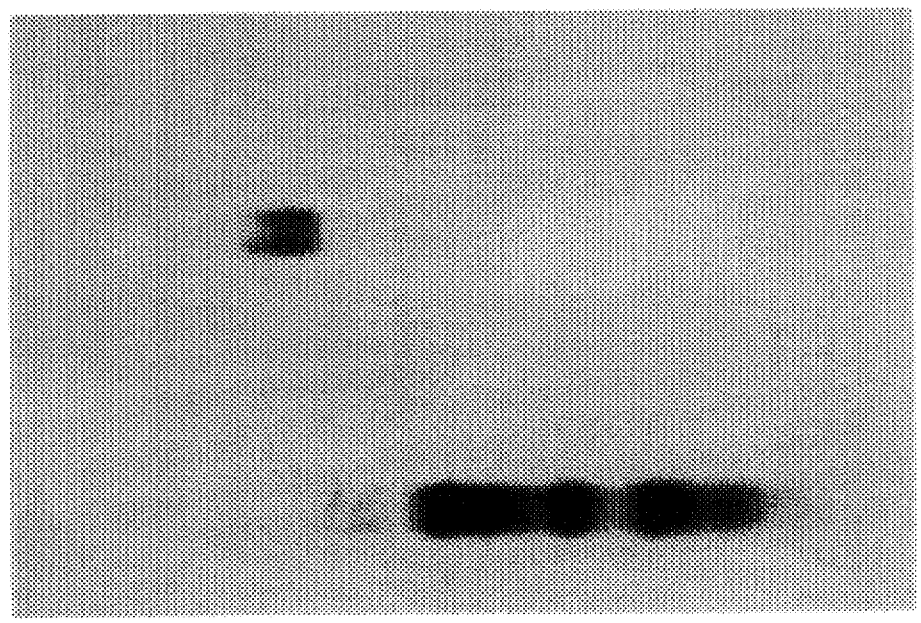
FIG. 21 shows an autoradiograph of a Northern blot of RNA isolated from the liver of an HCV infected chimpanzee, probed with HCV cDNA of clone 81.

An autoradiograph of the probed filter is shown in FIG. 21. Lane 1 contains $^{32}$P-labeled restriction fragment markers, Lanes 2–4 contain chimpanzee liver RNA as follows: lane 2 contains 30 micrograms of total RNA; lane 3 contains 30 micrograms of poly A− RNA; and lane 4 contains 20 micrograms of poly A+ RNA. As shown in FIG. 21, the liver of the HCV-infected chimpanzee contains a heterogeneous population of related poly A+ RNA molecules which hybridizes to the HCV cDNA probe, and which appears to be roughly greater than 5000 nucleotides in size. This RNA, which hybridizes to the HCV cDNA, could represent viral genomes and/or specific transcripts of the viral genome.

B. Identification of HCV-Derived RNA in Serum from Infected Individuals.

Nucleic acids were extracted from particles isolated from high titer chimpanzee HCV plasma as follows. First, viral particles were isolated from the plasma; a 90 ml aliquot diluted with 310 ml of a solution containing 50 mM Tris-HCl, pH 8.0, 1 mM EDTA, 100 mM NaCl. Debris was removed by centrifugation for 20 min at 15,000×g at 20° C. Viral particles in the resulting supernatant were then pelleted by centrifugation in a Beckman SW28 rotor at 28,000 rpm for 5 hours at 20° C. To release the viral genome, the particles were disrupted by suspending the pellets in 15 ml solution containing 1% sodium dodecyl sulfate (SDS), 10 mM EDTA, 10 mM Tris-HCl, pH 7.5, also containing 2 mg/ml proteinase K, followed by incubation at 45° C. for 90 min. Nucleic acids were isolated by adding 0.8 µg MS2 bacteriophage RNA as carrier, and extracting the mixture four times with a 1:1 mixture of phenol:chloroform (phenol saturated with 0.5M Tris-HCl, pH 7.5, 0.1% (v/v) beta-mercaptoethanol, 0.1% (w/v) hydroxyquinolone, followed by extraction two times with chloroform. The aqueous phase was concentrated with 1-butanol prior to precipitation with 2.5 volumes absolute ethanol overnight at 31° C. Nucleic acid was recovered by centrifugation in a Beckman SW41 rotor at 40,000 rpm for 90 min at 4° C., and dissolved in water that had been treated with 0.05% (v/v) diethylpyrocarbonate and autoclaved.

Figure 22:
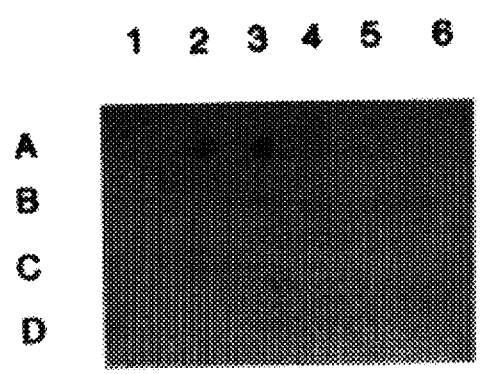
FIG. 22 shows an autoradiograph of HCV nucleic acid treated with RNase A or DNase I, and probed with HCV cDNA of clone 81.

Aliquots (equivalent to 1 ml of original plasma) of the isolated nucleic acids were resuspended in 20 microliters 50 mM Hepes, pH 7.5, 1 mm EDTA and 16 micrograms/ml yeast soluble RNA. The samples were denatured by boiling for 5 minutes followed by immediate freezing, and were treated with RNase A (5 microliters containing 0.1 mg/ml RNase A in 25 mM EDTA, 40 mM Hepes, pH 7.5) or with DNase I (5 microliters containing 1 unit DNase I in 10 mM $MgCl_2$, 25 mM Hepes, pH 7.5); control samples were incubated without enzyme. Following incubation, 230 mincrolieters of ice-cold 2×SSC containing 2 micrograms/ml yeast soluble RNA was added, and the samples were filtered on a nitrocellulose filter. The filters were hybridized with a cDNA probe from clone 81, which had been $^{32}$P-labeled by nick-translation. FIG. 22 shows asn autoradiograph of the filter. Hybridization signals were detected in the DNase treated and control samples (lanes 2 and 1, respectively), but were not detected in the RNase treated sample (lane 3). Thus, since RNase A treatment destroyed the nucleic acids isolated from the particles, and DNase I treatment had no effect, the evidence strongly suggests that the HCV genome is composed of RNA.

C. Characterization of the Strandedness of the HCV Genome.

The HCV genome was characterized with respect to its strandedness by isolating the nucleic acid fraction from HCV captured on anti-$HCV_{5-1-1}$ antibody coated polystyrene beads, and determining whether the isolated nucleic acid hybridized with plus and/or minus strands of HCV cDNA.

HCV was captured from HCV-infected chimpanzee plasma using polystyrene beads coated with immunopurified anti-HCV$_{5-1-1}$ antibody as follows. Protein-nucleic acid complexes present in infectious plasma of a chimp with HCV were isolated using purified human polyclonal anti-HCV antibodies which were bound to polystyrene beads. Polyclonal anti-HCV$_{5-1-1}$ antibodies were purified from serum from a human with HCV using the SOD-HCV polypeptide encoded in clone 5-1-1. The purified anti-HCV$_{5-1-1}$ antibodies were bound to polystyrene beads (¼" diameter, specular finish, Precision Plastic Ball Co., Chicago, Ill.) by incubating each at room temperature overnight with 1 ml of antibodies (1 microgram/ml in borate buffered saline, pH 8.5). Following the overnight incubation, the beads were washed once with TBST [50 mM Tris HCl, pH 8.0, 150 mM NaCl, 0.05% (v/v) Tween 20], and then with phosphate buffered saline (PBS) containing 10 mg/ml BSA. Control beads were prepared in an identical fashion, except that the purified anti-HCV$_{5-1-1}$ antibodies were replaced with total human immunoglobulin.

An aliquot (1 ml) of the HCV-infected chimp plasma was incubated for 3 hours at 37° C. with each of 5 beads coated with either anti-HCV$_{5-1-1}$ antibodies, or with control immunoglobulins. The beads were washed 3 times with TBST. The washed beads were incubated for 60 min. at 37° C. with 0.2 ml per bead of a solution containing proteinase K (1 mg/ml), 10 mM Tris HCl, pH 7.5, 10 mM EDTA, 0.25% (w/v) SDS, 10 micrograms/ml soluble yeast KNA, and the supernatant solution was removed. The supernatant was extracted with phenol and chloroform, and the nucleic acids precipitated with ethanol overnight at −20° C. The nucleic acid precipitate was collected by centrifugation, dried, and dissolved in 50 mM Hepes, pH 7.5. Duplicate aliquots of the soluble nucleic acids from the samples obtained from beads coated with anti-HCV$_{5-1-1}$ antibodies and with control beads contsining total human immunoglobulin were filtered onto to nitrocellulose filters.

Aliquots of the isolated genomic nucleic acid equivalent to 3 mls of high liter plasma were blotted onto nitrocellulose filters. As controls, aliquots of denatured HCV cDNA from clone 81 (2 picograms) was also blotted onto the same filters. The filters were probed with $^{32}$P-labeled mixture of plus or mixture of minus strands of single stranded DNA cloned from HCV cDNAs; the cDNAs were excised from clones 40b, 81, and 25c.

The single stranded probes were obtained by excising the HCV cDNAs from clones 81, 40b, and 25c with EcoRI, and cloning the cDNA fragments in M13vectors, mp18 and mp19 [Messing (1983)]. The M13 clones were sequenced to determine whether they contained the plus or minus strands of DNA derived from the HCV cDNAs. Sequencing was by the dideoxy chain termination method of Sanger et al. (1977).

Figure 23A:
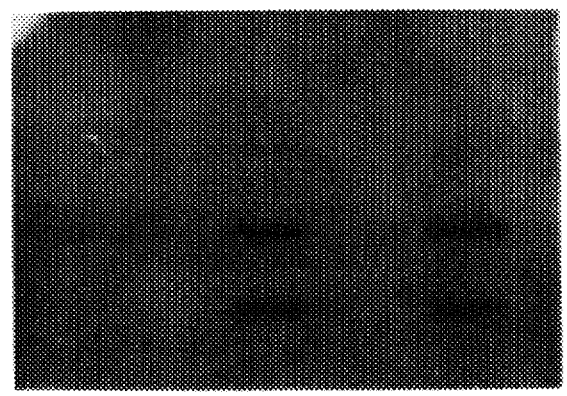
FIG. 23 shows autoradiographs of filters containing isolated HCV nucleic acids, probed with $^{32}$P-labeled plus and minus strand DNA probes derived from HCV cDNA in clone 81.
Figure 23B:
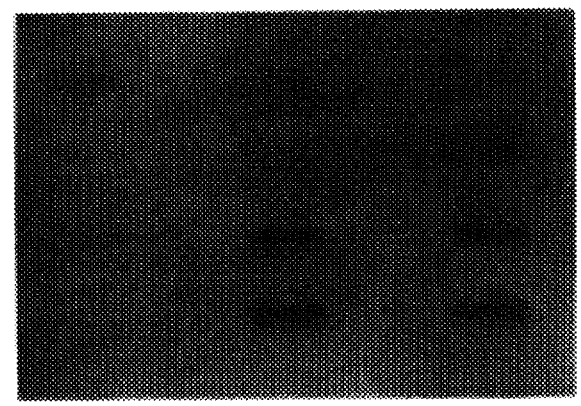

Each of a set of duplicate filters containing aliquots of the HCV genome isolated from the captured particles was hybridized with either plus or minus strand probes derived from the HCV cDNAs. FIG. 23 shows the autoradiographs obtained from probing the HCV genome with the mixture of probes derived from clones 81, 40b, and 25c. This mixture was used to increase the sensitivity of the hybridization assay. The samples in panel I were hybridized with the plus strand probe mixture. The samples in panel II were probed by hybridization with the minus strand probe mixture. The composition of the samples in the panels of the immunoblot are presented in the following Table.

TABLE

| lane | A | B |
| --- | --- | --- |
| 1 | HCV genome | * |
| 2 | — | * |
| 3 | * | cDNA 81 |
| 4 | — | cDNA 81 |

*is an undescribed sample.

As seen from the results in FIG. 23, only the minus strand DNA probe hybridizes with the isolated HCV genome. This result, in combination with the result showing that the genome is sensitive to RNase and not Dnase, suggests that the genome of NANBV is positive stranded RNA.

Detection of HCV RNA and Polynucleotides Derived Therefrom Using an HCV/cPCR Method A particularly useful method for detecting HCV RNA or polynucleotides derived from HCV RNA is the HCV/cPCR method, which is a subject of the herein application, and which utilizes the polymerase chain reaction technique (PCR) which is described by Saiki et al. (1986), by Mullis in U.S. Pat. No. 4,683,195, and by Mullis et al. in U.S. Pat. No. 4,683,202. The HCV/cPCR method utilizes primers and probes derived from the information provided herein concerning the nature of the HCV genome.

Generally, in the PCR technique, short oligonucleotide primers are prepared which match opposite ends of a desired sequence. The sequence between the primers need not be known. A sample of polynucleotide is extracted and denatured, preferably by heat, and hybridized with oligonucleotide primers which are present in molar excess. Polymerization is catalyzed by a template- and primer-dependent polymerase in the presence of deoxynucleotide triphosphates or nucleotide analogs (dNTPs). This results in two "long products" which contain the respective primers at their 5'-termini, covalently linked to the newly synthesized complements of the original strands. The replicated DNA is again denatured, hybridized with oligonucleotide primers, returned to polymerizing conditions, and a second cycle of replication is initiated. The second cycle provides the two original strands, the two long products from cycle 1, and two "short products" replicated from the long products. The short products contain sequences (sense or antisense) derived from the target sequence, flanked at the 5'- and 3'-termini with primer sequences. On each additional cycle, the number of short products is replicated exponentially. Thus, this process causes the amplification of a specific target sequence.

In the method, a sample is provided which is suspected of containing HCV RNA, or a fragment thereof. The sample is usually taken from an individual suspected of having NANBH; however, other sources of the sample are included, e.g., conditioned medium or cells from in vitro systems in which the virus has been replicated. The sample, however, must contain the target nucleic acid sequence(s).

The sample is then subjected to conditions which allow reverse transcription of HCV RNA into HCV cDNA. Conditions for reverse transcribing RNA are known to those of skill in the art, and are described in, for example, Maniatis et al. (1982), and in Methods in Enzymology. A preferred method of reverse transcription utilizes reverse transcriptase from a variety of sources, including recombinant molecules, and isolated from, for example, a retrovirus, preferably from avian myeloblastosis virus (AMV), and suitable conditions for the transcription. The HCV cDNA product of reverse transcription is in a RNA:DNA hybrid, which results from the first round of reverse transcription; subsequently, DNA:DNA hybrids result from two or more rounds of transcription.

The HCV cDNA resulting from reverse transcription is then subjected to PCR to amplify the target sequence. In order to accomplish this, the HCV cDNA is denatured, and the separated strands are hybridized with primers which flank the target sequence.

Strand separation may be accomplished by any suitable denaturing method, including physical, chemical, or enzymatic means, which are known to those of skill in the art. A preferred method, which is physical, involves heating the nucleic acid until it is completely (>99%) denatured. Typical heat denaturation involves temperatures ranging from about 80° C. to about 105° C., for times ranging from about 1 to 10 minutes.

After hybridization of the HCV cDNA with the primers, the target HCV sequences are replicated by a polymerizing means which utilizes a primer oligonucleotide to initiate the synthesis of the replicate chain. The primers are selected so that they are complementary to sequences of the HCV genome. Oligomeric primers which are complementary to regions of the sense and antisense strands of HCV cDNA can be designed from the HCV cDNA sequences from the composite cDNA sequence provided in FIG. 1.

The primers are selected so that their relative positions along a duplex sequence are such that an extension product synthesized from one primer, when it is separated from its template (complement), serves as a template for the extension of the other primer to yield a replicate chain of defined length.

The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the agent for polymerization. The exact lengths of the primers will depend on many factors, including temperature and source of the primer and use of the method. For example, depending on the complexity of the target sequence, the oligonucleotide primer typically contains about 15–45 nucleotides, although it may contain more or fewer nucleotides. Short primer molecules generally require cooler temperatures to form sufficiently stable hybrid complexes with the template.

The primers used herein are selected to be "substantially" complementary to the different strands of each specific sequence to be amplified. Therefore, the primers need not reflect the exact sequence of the template, but must be sufficiently complementary to selectively hybridize with their respective strands. For example, a non-complementary nucleotide fragment may be attached to the 5'-end of the primer, with the remainder of the primer sequence being complementary to the strand. Alternatively, non-complementary bases or longer sequences can be interspersed into the primer, provided that the primer has sufficient complementarity with the sequence of one of the strands to be amplified to hybridize therewith, and to thereby form a duplex structure which can be extended by the polymerizing means. The non-complementary nucleotide sequences of the primers may include restriction enzyme sites. Appending a restriction enzyme site to the end(s) of the target sequence would be particularly helpful for cloning of the target sequence.

It will be understood that "primer", as used herein, may refer to more than one primer, particularly in the case where there is some ambiguity in the information regarding the terminal sequence(s) of the target region to be amplified. Hence, a "primer" includes a collection of primer oligonucleotides containing sequences representing the possible variations in the sequence or includes nucleotides which allow a typical basepairing. One of the primer oligonucleotides in this collection will be homologous with the end of the target sequence. A specific case is shown in the Examples, where oligomer sets of 44-mers and 45-mers were utilized to prime the amplification of a potentially variant region of the HCV genome.

It is anticipated that there will be a variety of strains or isolates of HCV with sequences which deviate from HCV1, the prototype strain. Therefore, in order to detect variant strains it is preferable to construct primers which hybridize to conserved regions of the HCV genome. The conserved regions may be determined by comparing the nucleotide or amino acid sequences of several HCV strains/isolates. There appear to be at least three regions of conserved amino acid in the HCV genome, described supra., from which primers may be derived. These regions are believed to be. The primers described infra., in the Examples, are derived from what are believed to be conserved regions of HCV, based upon sequence homology to that of the Flaviviruses.

The oligonucleotide primers may be prepared by any suitable method. Methods for preparing oligonucleotides of specific sequence are known in the art, and include, for example, cloning and restriction of appropriate sequences, and direct chemical synthesis. Chemical synthesis methods may include, for example, the phosphotriester method described by Narang et al. (1979), the phosphodiester method disclosed by Brown et al. (1979), the diethylphosphoramidate method disclosed in Beaucage et al. (1981), and the solid support method in U.S. Pat. No. 4,458,066.

The primers may be labeled, if desired, by incorporating means detectable by spectroscopic, photochemical, biochemical, immunochemical, or chemical means.

Template-dependent extension of the oligonucleotide primer(s) is catalyzed by a polymerizing agent in the presence of adequate amounts of the four deoxyribonucleotide triphosphates (dATP, dGTP, dCTP and dTTP) or analogs, in a reaction medium which is comprised of the appropriate salts, metal cations, and pH buffering system. Suitable polymerizing agents are enzymes known to catalyze primer- and template-dependent DNA synthesis. Known DNA polymerases include, for example, $E.\ coli$ DNA polymerase I or its Klenow fragment, $T_4$ DNA polymerase, and Taq DNA polymerase. The reaction conditions for catalyzing DNA synthesis with these DNA polymerases are known in the art.

The products of the synthesis are duplex molecules consisting of the template strands and the primer extension strands, which include the target sequence. These products, in turn, serve as template for another round of replication. In the second round of replication, the primer extension strand of the first cycle is annealed with its complementary primer; synthesis yields a "short" product which is bounded on both the 5'- and the 3'-ends by primer sequences or their complements. Repeated cycles of denaturation, primer annealing, and extension result in the exponential accumulation of the target region defined by the primers. Sufficient cycles are run to achieve the desired amount of polynucleotide containing the target region of nucleic acid. The desired amount may vary, and is determined by the function which the product polynucleotide is to serve.

The PCR method can be performed in a number of temporal sequences. For example, it can be performed step-wise, where after each step new reagents are added, or in a fashion where all of the reagents are added simultaneously, or in a partial step-wise fashion, where fresh reagents are added after a given number of steps.

In a preferred method, the PCR reaction is carried out as an automated process which utilizes a thermostable enzyme. In this process the reaction mixture is cycled through a denaturing region, a primer annealing region, and a reaction region. A machine may be employed which is specifically adapted for use with a thermostable enzyme, which utilizes temperature cycling without a liquid handling system, since the enzyme need not be added at every cycle. This type of machine is commercially available from Perkin Elmer Cetus Corp.

After amplification by PCR, the target polynucleotides are detected by hybridization with a probe polynucleotide which forms a stable hybrid with that of the target sequence under stringent to moderately stringent hybridization and wash conditions. If it is expected that the probes will be completely complementary (i.e., about 99% or greater) to the target sequence, stringent conditions will be used. If some mismatching is expected, for example if variant strains are expected with the result that the probe will not be completely complementary, the stringency of hybridization may be lessened. However, conditions are chosen which rule out nonspecific/adventitious binding. Conditions which affect hybridization, and which select against nonspecific binding are known in the art, and are described in, for example, Maniatis et al. (1982). Generally, lower salt concentration and higher temperature increase the stringency of binding. For example, it is usually considered that stringent conditions are incubation in solutions which contain approximately 0.1×SSC, 0.1% SDS, at about 65° C. incubation/ wash temperature, and moderately stringent conditions are incubation in solutions which contain approximately 1–2× SSC, 0.1% SDS and about 50°–65° C. incubation/wash temperature. Low stringency conditions are 2×SSC and about 30°14 50° C.

Probes for HCV target sequences may be derived from the HCV cDNA sequence shown in FIG. 1, or from new HCV isolates. The HCV probes may be of any suitable length which span the target region, but which exclude the primers, and which allow specific hybridization to the target region. If there is to be complete complementarity, i.e., if the strain contains a sequence identical to that of the probe, since the duplex will be relatively stable under even stringent conditions, the probes may be short, i.e., in the range of about 10–30 base pairs. If some degree of mismatch is expected with the probe, i.e., if it is suspected that the probe will hybridize to a variant region, the probe may be of greater length, since length seems to counterbalance some of the effect of the mismatch(es). An example of this is found in the Examples, where the probe was designed to bind to potential variants of HCV1. In this case, the primers were designed to bind to HCV cDNA derived from a hypothetical conserved region of the HCV genome, and the target region was one which potentially contained variations (based upon the Flavivirus model). The probe used to detect the HCV target sequences contained approximately 268 base pairs.

The probe nucleic acid having a sequence complementary to the target sequence may be synthesized using similar techniques described supra. for the synthesis of primer sequences. If desired, the probe may be labeled. Appropriate labels are described supra.

In some cases, it may be desirable to determine the length of the PCR product detected by the probe. This may be particularly true if it is suspected that variant HCV strains may contain deletions within the target region, or if one wishes to confirm the length of the PCR product. In such cases it is preferable to subject the products to size analysis as well as hybridization with the probe. Methods for determining the size of nucleic acids are known in the art, and include, for example, gel electrophoresis, sedimentation in gradients, and gel exclusion chromatography.

The presence of the target sequence in a biological sample is detected by determining whether a hybrid has been formed between the HCV polynucleotide probe and the nucleic acid subjected to the PCR amplification technique. Methods to detect hybrids formed between a probe and a nucleic acid sequence are known in the art. For example, for convenience, an unlabeled sample may be transferred to a solid matrix to which it binds, and the bound sample subjected to conditions which allow specific hybridization with a labeled probe; the solid matrix is than examined for the presence of the labeled probe. Alternatively, if the sample is labeled, the unlabeled probe is bound to the matrix, and after the exposure to the appropriate hybridization conditions, the matrix is examined for the presence of label. Other suitable hybridization assays are described supra.

Determination of Variant HCV Sequences Using PCR

In order to identify variant HCV strains, and thereby to design probes for those variants, the above described HCV/ cPCR method is utilized to amplify variant regions of the HCV genome, so that the nucleotide sequences of these variant target regions can be determined. Generally, variant types of HCV might be expected to occur in different geographic locations than that in which the HCV1 strain is predominant, for example, Japan, Africa, etc.; or in different vertebrate species which are also infected with the virus. Variant HCV may also arise during passage in tissue culture systems, or be the result of spontaneous or induced mutations.

In order to amplify the variant target region, primers are designed to flank the suspect region, and preferably are complementary to conserved regions. Primers to two regions of HCV which are probably conserved, based upon the Flavivirus model, are described in the Examples. These primers and probes may be designed utilizing the sequence information for the HCV1 strain provided in FIG. 1.

Analysis of the nucleotide sequence of the target region(s) may be by direct analysis of the PCR amplified products. A process for direct sequence analysis of PCR amplified products is described in Saiki et al. (1988).

Alternatively, the amplified target sequence(s) may be cloned prior to sequence analysis. A method for the direct cloning and sequence analysis of enzymatically amplified genomic segments has been described by Scharf (1986). In the method, the primers used in the PCR technique are modified near their 5'-ends to produce convenient restriction sites for cloning directly into, for example, an M13 sequencing vector. After amplification, the PCR products are cleaved with the appropriate restriction enzymes. The restriction fragments are ligated into the M13 vector, and transformed into, for example, a JM 103 host, plated out, and the resulting plaques are screened by hybridization with a labeled oligonucleotide probe. Other methods for cloning and sequence analysis are known in the art.

Universal Primers for Flaviviruses and for HCV

Studies of the nature of the genome of the HCV, utilizing probes derived from the HCV cDNA, as well as sequence information contained within the HCV cDNA, are suggestive that HCV is a Flavi-like virus. These studies are described in U.S. Pat. No. 5,350,671 owned by the herein assignee, and which is incorporated herein in its entirety. A comparison of the HCV cDNA sequence derived from the HCV cDNA clones with known sequences of a number of Flaviviruses show that HCV contains sequences which are homologous to conserved sequences in the Flaviviruses. These conserved sequences may allow the creation of primers which may be universal in their application for amplification of target regions of Flaviviruses, and for HCV. These sequences are the 16-mer or smaller sequences from the 3'-termini of the primers described in the Examples. Identification of the species is then accomplished utilizing a probe specific for the species. The genomes of a number of Flaviviruses are known in the art, and include, for example, Japanese Encephalitis Virus (Sumiyoshi et al. (1987)), Yellow Fever Virus (Rice et al. (1985)), Dengue Type 2 Virus (Hahn et al. (1988)), Dengue Type 4 Virus (Mackow (1987)), and West Nile Virus (Castle et al. (1986)). Identification of HCV RNA is accomplished utilizing a probe specific for HCV, the sequence of which can be determined the HCV cDNA sequences provided herein.

Alternatively, utilization of sets of probe(s) designed to account for codon degeneracy and therefore contain common sequences to the Flaviviruses and to HCV, as determined by a comparison of HCV amino acid sequences with the known sequences of the Flaviviruses, allows a general detection system for these viruses.

Construction of Desired DNA Sequences

Synthetic oligonucleotides may be prepared using an automated oligonucleotide synthesizer as described by Warner (1984). If desired the synthetic strands may be labeled with $^{32}$P by treatment with polynucleotide kinase in the presence of $^{32}$P-ATP, using standard conditions for the reaction.

DNA sequences, including those isolated from cDNA libraries, may be modified by known techniques, including, for example site directed mutagenesis, as described by Zoller (1982). Briefly, the DNA to be modified is packaged into phage as a single stranded sequence, and converted to a double stranded DNA with DNA polymerase using, as a primer, a synthetic oligonucleotide complementary to the portion of the DNA to be modified, and having the desired modification included in its own sequence. The resulting double stranded DNA is transformed into a phage supporting host bacterium. Cultures of the transformed bacteria, which contain replications of each strand of the phage, are plated in agar to obtain plaques. Theoretically, 50% of the new plaques contain phage having the mutated sequence, and the remaining 50% have the original sequence. Replicates of the plaques are hybridized to labeled synthetic probe at temperatures and conditions which permit hybridization with the correct strand, but not with the unmodified sequence. The sequences which have been identified by hybridization are recovered and cloned.

Kits for Screening for HCV Derived Polynucleotides

Oligomers which are probes and/or primers for amplification and/or screening of samples for HCV can be packaged into kits. Kits for screening for HCV sequences include the oligomeric probe DNAs. Kits for amplification of HCV sequences may include the oligomeric primers used in the amplification. The kits usually contain the probes or primers in a premeasured or predetermined amount, as well as other suitably packaged reagents and materials, in separate suitable containers, needed for the particular hybridization and/or amplification protocol(s). For example, the kit may contain standards, buffers, supports, enzymes, substrates, label probes, binding partners, and/or instructions for conducting the test.

EXAMPLES

Described below are examples of the present invention which are provided only for illustrative purposes, and not to limit the scope of the present invention.

Isolation and Sequence of Clone 5'-clone32

A clone containing sequence from the 5'-region of the HCV genome, upstream of the sequence in clone b114a, was isolated and the nucleotide sequence determined by a modification of the method for the isolation and sequence of clones generated by PCR amplification of the 3'-region of the genome, described in U.S. Pat. No. 5,350,671, which is incorporated by reference. Generally, a target region of the genome was amplified by the PCR technique described in Saiki et al. (1986), and in Saiki et al (1988). The HCV RNA which was amplified was obtained by extracting human serum (U.S. clinical isolate, HCV27) using a cold guanidinium thiocyanate method described by Han et al. (1987). The extracted RNA was converted into single stranded cDNA with reverse transcriptase, using a primer, JH94, which is complementary to nucleotides −250 to −223 of the HCV genome (see FIG. 1). The sequence of JH94 is:

5' CCT GCG GCC GCA CGA CAC TCA TAC TAA 3'.

Conversion of single- to double-stranded HCV cDNA was accomplished by tailing the DNA with approximately 20 to 50 dA residues using terminal deoxynucleotidyl transferase (Sambrook et al. (1989), MOLECULAR CLONING), and replicating the tailed molecule using the following oligo-dT primer-adapter, which contains a NotI site, and an sp6 promoter:

| Stuffer | NotI | SP6 Promoter | Primer |
|---|---|---|---|
| AATTC | GCGGCCGC | CATACGATTTAGGTGACACTATAGAA | T$_{15}$ |

The resultant cDNA was subjected to amplification by PCR using two primers, JH94 (described supra.) and JH11, which has the following sequence.

| Primer | Sequence |
|---|---|
| JH11 (20mer) | AATTCGGGCGGCCGCCATACGA |

The PCR reaction was carried out by suspending the cDNA and the primers in 100 microliters of reaction mixture containing the four deoxynucleoside triphosphates, buffer salts and metal ions, and a thermostable DNA polymerase isolated from *Thermus aquaticus* (Taq polymerase), which are in a Perkin Elmer Cetus PCR kit (N801-0043 or N801-0055). The PCR reaction was performed for 35 cycles in a Perkin Elmer Cetus DNA thermal cycler. Each cycle consisted of a 1.5 min denaturation step at 94° C., an annealing step at 60° C. for 2 min, and a primer extension step at 72° C. for 3 min.

The PCR products were digested with NotI, and cloned into pUC18S. Clones containing HCV nucleotide sequences were obtained by screening with a probe, Alex90, which is derived from nucleotides −312 to −283 of the HCV1 genome, and which has the sequence:

5' ACC ATG AAT CAC TCC CCT GTG AGG AAC TAC 3'.

The HCV cDNAs in the isolated clones were sequenced by the dideoxy chain termination method (Sanger et al. (1977)). The sequence of HCV cDNA in one of the isolated clones, 5'-clone32, spans the region of nucleotides −224 to −341 in FIG. 1.

An analysis of the nucleotide sequence of the HCV cDNA showed that the replicate of the HCV RNA strand contains a GC-rich stretch which may be capable of forming a stable hairpin structure:

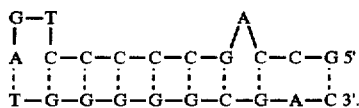

In the structure, the dashed lines indicate possible hydrogen bonds between complementary nucleotides.

A search in the computer database, Genebank, revealed that homologous sequences were absent from known viral sequences. Thus, this sequence may be unique to the 5'-terminus of the HCV genome.

A hairpin structure may serve as a recognition signal for a transcriptase and/or it may contribute to the stability of the RNA at the 5'-terminus.

Compiled HCV cDNA Sequences

An HCV cDNA sequence has been compiled from a series of overlapping clones derived from various HCV cDNA libraries described in U.S. Pat. No. 5,350,671, to which has been added the sequence of 5'-clone32. The other clones from which FIG. 1 has been derived are b114a, 18g, ag30a, CA205a, CA290a, CA216a, pi14a, CA167b, CA156e, CA84a, CA59a, K9-1 (also called k9-1), 26j, 13i, 12f, 14i, 11b, 7f, 7e, 8h, 33c, 40b, 37b, 35, 36, 81, 32, 33b, 25c, 14c, 8f, 33f, 33g, 39c, 35f, 19g, 26g, 15e, b5a, 16jh, C6k and p131jh. The methods for isolation of these clones, as well as their sequences, are discussed in U.S. Ser. No. 07/456,637, which is incorporated herein by reference. In FIG. 1, the three dashes above the sequence indicate the position of the putative initiator methionine codon.

Clone b114a overlaps with clones 18g, ag30a, and CA205a, except that clone b114a contains an extra two nucleotides upstream of the sequence in clone 18g (i.e., 5'-CA). These extra two nucleotides have been included in the HCV genomic sequence shown in FIG. 1.

It should be noted that although several of the clones described supra, have been obtained from libraries other than the original HCV cDNA lambda-gt11 C library (ATCC No. 40394), these clones contain HCV cDNA sequences which overlap HCV cDNA sequences in the original library. Thus, essentially all of the HCV sequence is derivable from the original lambda-gt11 C library (ATCC No. 40394) which was used to isolate the first HCV cDNA clone (5-1-1). The isolation of clone 5-1-1 is described in U.S. Ser. No. 07/456,637, which is incorporated herein by reference.

The putative sequence of the major HCV polyprotein encoded in the composite of HCV1 cDNA is also shown. The first amino acid in the sequence is the putative initiator methionine of the large ORF. The variant amino acids, due to the clonal heterogeneities, are indicated above the sequence. Since the lambda gt11 library was created from serum obtained from one individual (see U.S. Ser. No. 07/456,637), the results suggest that variant viral sequences (both nucleotide and amino acid) are present in that individual.

An examination of the composite HCV cDNA sequence shows that besides the large ORF, there are a number of ORFs upstream of that encoding the polyprotein, and within the sequence encoding the polyprotein there are a large number of smaller ORFs in the other two translational frames. The ORFs upstream of the HCV polyprotein are shown in the Table immediately below.

TABLE

| ORFs Upstream of that Encoding the Large HCV Polyprotein | | |
|---|---|---|
| Nucl. # | Translation Frame | Amino Acid Sequence |
| −310 | 1 | MNHSPVRNYCLHAESV |
| −329 | 3 | MGATLHHESLPCEELL SSRRKRLAMALV |
| −246 | 2 | MSVVQPPGPPLPGEP |
| −127 | 1 | MPGDLGVPPQDC |

The reading frame, position, and size of the ORFs downstream of the sequence encoding the putative initiator MET of the polyprotein are shown in the Table below. The major polyprotein is that translated from reading frame 2.

TABLE

| ORFs Downstream of the Putative Initiator MET Encoding Sequence | | |
|---|---|---|
| Reading Frame | Size (aa) | Position (bp) |
| 1 | 168 | 696 |
| 1 | 105 | 2343 |
| 1 | 119 | 5616 |
| 2 | 3025 | −42 |
| 3 | 160 | 5 |
| 3 | 111 | 1667 |
| 3 | 148 | 6893 |

In addition to the above, an examination of the sequence which is complementary to the genomic strand of HCV RNA also contains several small ORFs. One of these ORFs, which is complementary to nucleotides −341 to +837 in the HCV RNA sequence, encodes a polypeptide of 385 amino acids.

Comparison of the Sequences of 5'-Regions
Obtained from HCV Isolates from Different
Geographical Locations Nucleotide sequences from the 5'-regions of HCV isolates from the U.S.A. (HCV18, HCV27), from Italy (HCVI1, HCVI24), and from Korea (HCVK1) were compared.

Isolation of the HCV cDNA sequences was essentially as described supra., for the isolation of 5'-clone32, except for the following. The extracted RNA was reverse-transcribed into cDNA using as primers either JH51 or r16, which are complementary to HCV nucleotides −90 to −73 and 366 to 383, respectively. The sequences of these primers are as follows.

| Primer | Sequence |
|---|---|
| JH51 | 5' CCC AAC ACT ACT CGG CTA 3' |
| r16 | 5' CAC GTA AGG GTA TCG ATG 3' |

Amplification of the HCV dsDNA was by the PCR method using JH93 and JH52 as 5'- and 3'-primers, respectively. The HCV sequence in JH93 is derived from HCV nucleotides −317 to −296, that in JH52 is from HCV nucleotides −93 to −117; the nucleotide numbers are indicated in parentheses below the sequences. In JH52 the underlined dinucleotide has been mutated to create the NotI site. The sequences of these primers are the following.

| (Primer) | Stuffer | NotI | HCV sequence | |
|---|---|---|---|---|
| (JH93) 5' TTC | | GCGGCCGC | ACTCCATGAATCACTCCCC | 3' |
| | | (−317) | | (−296) |
| (JH52) 5' AGTCTT | GCGGCCGC | | ACGCCCAAATC | 3' |
| (−93) | | | (−117) | |

After amplification, the PCR products were cleaved by NotI, and cloned into pUC18S. The HCV cDNAs were sequenced either by direct sequencing after amplification by PCR, or alternatively, the cloned HCV cDNAs were sequenced by the primer extension and the dideoxy method. Primer extension and the dideoxy method of sequencing were performed as described supra., for the sequence of 5'-clone32.

The PCR method for direct sequencing used Alex90 (see supra. for the sequence) as the 5'-primer, and r25 as the 3'-primer. Alex90 is derived from HCV nucleotides −312 to −283, and r25 is derived from nucleotides 365 to 342 (See FIG. 1). The sequence of r25 is:

5' ACC TTA CCC AAA TTG CGC GAC CTA 3'.

A comparison of the sequences of the 5'-region of HCV27, HCVK1, HCVI1, HCVI24, and HCV18 with the sequence of the prototype HCV, HCV1, showed the following. The examined 5'-region is highly conserved amongst the 5 HCV isolates. The sequences appeared to be identical except for one nucleotide which was deleted at position −171 in HCVI24, and for the ambiguity in four nucleotides at positions −222 to −219 in isolate HCVK1.

The high levels of sequence conservation in this region may reflect the role of this region in viral replication, and/or transcription, and/or translation.

Detection of Positive and Negative Strand 5'-HCV RNA in Serum

The RNA in HCV27, isolated from serum, was analyzed for the presence of positive and negative strands using the PCR method. The PCR method was performed essentially as described above, except for the following. The extracted HCV27 RNA was reverse transcribed into single-stranded cDNA using as a primer either Alex90 or JH52 (see supra. for the sequences). The sequence of Alex90 matches that in nucleotides −312 to −283 of the positive strand of HCV RNA, whereas JH52 matches that of nucleotides −117 to −93 of the negative strand. the resulting single-stranded HCV cDNAs were each separately amplified by PCR using Alex90 and JH52. Detection of the amplified products was accomplished by Southern blotting, using Alex89 as the probe. Alex89 matches nucleotide numbers −203 to −175 of HCV RNA. The sequence of Alex89 is:

5' CCA TAG TGG TCT GCG GAA CCG GTG AGT ACA 3'.

The analysis indicated that, by this method, the signals of the amplified products of both RNA strands were of equal intensity. These results are suggestive that HCV RNA in the 5'-region may exist as double-stranded RNA.

Probes for Sandwich Hybridization for HCV

This example exemplifies the sets of label and capture probes useful to detect HCV RNA in biological samples, using essentially the assay described in U.S. Pat. No. 4,868, 105. The method is a solution-phase sandwich hybridization assay which utilizes both capture and label probes which hybridize to target sequences in an analyte nucleic acid. In the screening of biological samples for HCV, the probes used bind to conserved regions of the HCV genome, and the HCV binding regions are selected for their uniqueness to the HCV genome. The regions which bind to the binding partner of the capture probe, or the portion of the label probe which binds to the labeling moiety (or to an amplifying multimer if the method described in EPO Publication No. 317.077 is used), are selected such that they do not bind to any of the known sequences in the databank or in HCV, and which have the appropriate content of Gs and Cs to allow stable duplex formation with their complements under the selection conditions. The capture and label probes are in sets, and the probes of one set do not intersperse with the probes of another set. These probes are comprised of sequences which are complementary to the following nucleotide sequences in the coding strand of the prototype HCV cDNA sequence shown in FIG. 1.

Set 1

| Probe type | Probe Number | Complement of Nucleotide Numbers |
|---|---|---|
| Capture | 42.XT1.1 | −318 to −289 |
| Capture | 42.XT1.2 | −285 to −256 |
| Capture | 42.XT1.3 | −252 to −223 |
| Capture | 42.XT1.4 | −219 to −190 |
| Label | 42.LLA2C.5 | −186 to −157 |
| Label | 42.LLA2C.6 | −153 to −124 |
| Label | 42.LLA2C.7 | −120 to −91 |
| Label | 42.LLA2C.8 | −87 to −58 |
| Label | 42.LLA2C.9 | −54 to −25 |
| Label | 42.LLA2C.10 | −21 to 9 |
| Label | 42.LLA2C.11 | 13 to 42 |
| Label | 42.LLA2C.12 | 46 to 75 |
| Label | 42.LLA2C.13 | 79 to 108 |
| Label | 42.LLA2C.14 | 112 to 141 |
| Label | 42.LLA2C.15 | 145 to 174 |

Set 2

| Probe type | Probe Number | Complement of Nucleotide Numbers |
|---|---|---|
| Capture | 42.16.XT1 | 4378 to 4407 |
| Capture | 42.17.XT1 | 4411 to 4440 |
| Capture | 42.18.XT1 | 4444 to 4473 |
| Capture | 42.19.XT1 | 4477 to 4506 |
| Capture | 42.20.XT1 | 4510 to 4539 |
| Label | 42.21.LLA2C | 4543 to 4572 |
| Label | 42.22.LLA2C | 4576 to 4605 |
| Label | 42.23.LLA2C | 4609 to 4638 |
| Label | 42.24.LLA2C | 4642 to 4671 |
| Label | 42.25.LLA2C | 4675 to 4704 |
| Label | 42.26.LLA2C | 4708 to 4737 |
| Label | 42.27.LLA2C | 4771 to 4770 |
| Label | 42.28.LLA2C | 4774 to 4803 |
| Label | 42.29.LLA2C | 4807 to 4836 |
| Label | 42.30.LLA2C | 4840 to 4869 |
| Label | 42.31.LLA2C | 4873 to 4902 |

Set 3

| Probe type | Probe Number | Complement of Nucleotide Numbers |
|---|---|---|
| Capture | 42.32.XT1 | 4056 to 4085 |
| Capture | 42.33.XT1 | 4089 to 4085 |
| Capture | 42.34.XT1 | 4122 to 4151 |
| Capture | 42.35.XT1 | 4155 to 4184 |
| Label | 42.36.LLA2C | 4188 to 4217 |

-continued

Set 3

| Probe type | Probe Number | Complement of Nucleotide Numbers |
|---|---|---|
| Label | 42.37.LLA2C | 4221 to 4250 |
| Label | 42.38.LLA2C | 4254 to 4283 |
| Label | 42.39.LLA2C | 4287 to 4316 |
| Label | 42.40.LLA2C | 4230 to 4349 |
| Label | 42.41.LLA2C | 4353 to 4382 |
| Label | 42.42.LLA2C | 4386 to 4415 |
| Label | 42.43.LLA2C | 4419 to 4448 |

In the above sets, each capture probe contains, in addition to the sequences complementary to the HCV sequences, the following sequence downstream of the HCV sequence (i.e., at the 3'-end):

5' CTT CTT TGG AGA AAG TGG TG 3'.

The sequence common to each capture probe is complementary to a sequence in the binding partner(s), so that after hybridization, the duplex can be captured via affixation to the solid phase.

Also, in each set, each label probe contains, in addition to the sequences complementary to the HCV sequences, the following sequence downstream of the HCV sequence:

5' TTA GGC ATA GGA CCC GTG TC 3'.

If the method described in EPO Publication No. 317,077 is used, the sequence common to each label probe is complementary to a sequence in a multimer, to allow hybrid duplex formation with that multimer.

Figure 9A:
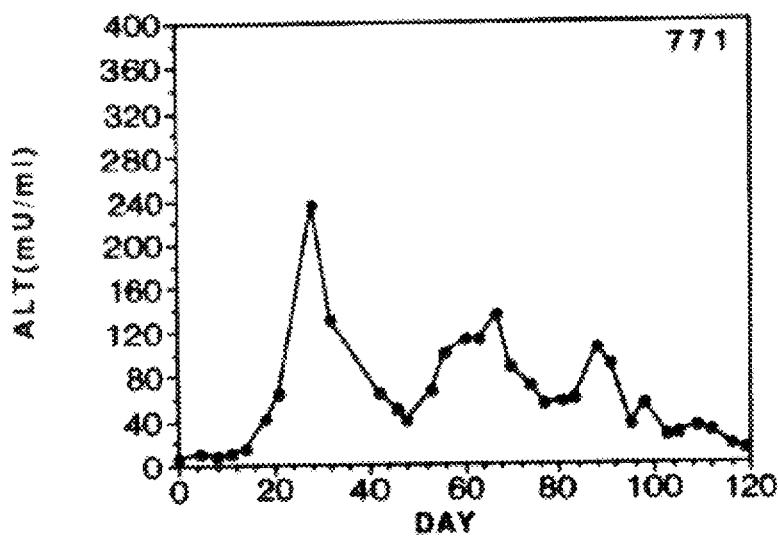
FIG. 9A and 9B are graphs showing the temporal relationship between the display of liver damage, the presence of HCV RNA, and the presence of anti-HCV antibodies for two chimpanzees with NANBH.
Figures 1, 9B:
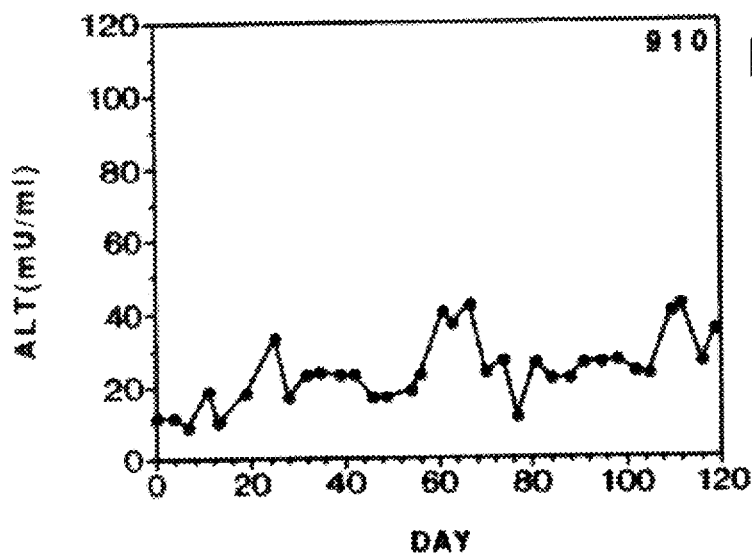
FIG. 1 shows the the compiled HCV cDNA sequence derived from the clone described herein and from the compiled HCV cDNA sequence presented in U.S. Ser. No. 07/456,637. The clones from which the sequence was derived are 5'-clone32, b114a, 18g, ag30a, CA205a, CA290a, CA216a, pi14a, CA167b, CA156e, CA84a, CA59a, K9-1 (also called k9-1), 26j, 13i, 12f, 14i, 11b, 7f, 7e, 8h, 33c, 40b, 37b, 35, 36, 81, 32, 33b, 25c, 14c, 8f, 33f, 33g, 39c, 35f, 19g, 26g, 15e, b5a, 16jh, 6k, and p131jh. In the figure the three horizontal dashes above the sequence indicate the position of the putative initiator methionine codon. Also shown in the figure is the amino acid sequence of the putative polyprotein encoded in the HCV cDNA. Heterogeneities in cloned DNAs of HCV1 are indicated by the amino acids indicated above the putatively encoded sequence of the large ORF; the parentheses indicate that the heterogeneity was detected at or near to the 5'- or 3'-end of the HCV cDNA in the clone.
Figures 2, 9B:
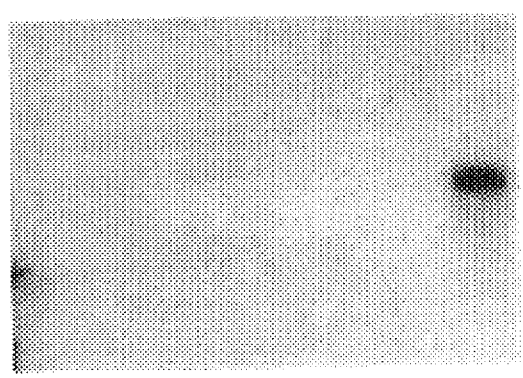
FIG. 2 shows the sequences of capture and label probes for the detection of HCV RNA in biological samples.

The sequences of the probes in the above sets are shown in FIG. 2.

Detection of HCV Polynucleotide Sequences Using PCR Amplification

The generalized method for amplification of HCV RNA by cPCR is shown in FIG. 4. In the diagram it is contemplated that the RNA strand is a virion or mRNA strand, which is a "sense" strand. However, it is also possible that replicative intermediate forms may also be detected which would be "anti-sense"; in this case the primer would be "sense". An RNA sense strand containing the target region is hybridized with an anti-sense primer which primes the synthesis of the replicate strand containing the target. cDNA to the RNA template is synthesized with a primer- and template-dependent reverse transcriptase. The cDNA in the resulting RNA:cDNA hybrid is released by denaturation and treatment with RNAse. Primers are annealed to the cDNA, and extended with a primer- and template-dependent DNA polymerase. The products are denatured, re-annealed to primers, and a second round of synthesis is conducted. A number of cycles are run until the amplified product containing the target region is in a desired amount, which is at least a detectable level.

Detection of Amplified HCV Nucleic Acid Sequences derived from HCV Nucleic Acid Sequences in Liver and Plasma Specimens from Chimpanzees with NANBH HCV nucleic acids present in liver and plasma of chimpanzees with NANBH, and not in control chimpanzees, were amplified using essentially the polymerase chain reaction (PCR) technique described by Saiki et al. (1986). The primer oligonucleotides were derived from the HCV cDNA sequences in clone 81, or clones 36 and 37b. The amplified sequences were detected by gel electrophoresis and a modified Southern blotting method, using as probes the appropriate cDNA oligomer or nick-translated cDNA sequence with a sequence from the region between, but not including, the two primers.

Samples of RNA containing HCV sequences to be examined by the amplification system were isolated from liver biopsies of three chimpanzees with NANBH, and from two control chimpanzees. The isolation of the poly $A^+$ RNA fraction was by the guanidinium thiocyanate procedure described in Maniatis et al. (1982).

Samples of RNA which were to be examined by the amplification system were also isolated from the plasmas of two chimpanzees with NANBH, and from one control chimpanzee, as well as from a pool of plasmas from control chimpanzees. One infected chimpanzee had a titer equal to or greater than $10^6$ CID/ml, and the other infected chimpanzee had a titer equal to or greater than $10^5$ CID/ml.

The nucleic acids were extracted from the plasma as follows. Either 0.1 ml or 0.01 ml of plasma was diluted to a final volume of 1.0 ml, with a TENB/proteinase K/SDS solution (0.05M Tris-HCL, pH 8.0, 0.001M EDTA, 0.1M NaCl, 1 mg/ml Proteinase K, and 0.5% SDS) containing 10 micrograms/ml polyadenylic acid, and incubated at 37° C. for 60 minutes. After this proteinase K digestion, the resultant plasma fractions were deproteinized by extraction with TE (10.0 mM Tris-HCl, pH 8.0, 1 mM EDTA) saturated phenol. The phenol phase was separated by centrifugation, and was reextracted with TENB containing 0.1% SDS. The resulting aqueous phases from each extraction were pooled, and extracted twice with an equal volume of phenol/chloroform/isoamyl alcohol [1:1(99:1)], and then twice with an equal volume of a 99:1 mixture of chloroform/isoamyl alcohol. Following phase separation by centrifugation, the aqueous phase was brought to a final concentration of 0.2M Na Acetate, and the nucleic acids were precipitated by the addition of two volumes of ethanol. The precipitated nucleic acids were recovered by ultracentrifugation in a SW 41 rotor at 38K, for 60 minutes at 4° C.

In addition to the above, the high titer chimpanzee plasma and the pooled control plasma alternatively were extracted with 50 micrograms of poly A carrier by the procedure of Chomcyzski and Sacchi (1987). This procedure uses an acid guanidinium thiocyanate extraction. RNA was recovered by centrifugation at 10,000 RPM for 10 minutes at 4° C. in an Eppendorf microfuge.

On two occasions, prior to the synthesis of cDNA in the PCR reaction, the nucleic acids extracted from plasma by the proteinase K/SDS/phenol method were further purified by binding to and elution from S and S Elutip-R Columns. The procedure followed was according to the manufacturer's directions.

The cDNA used as a template for the PCR reaction was derived from the nucleic acids (either total nucleic acids or RNA) prepared as described above. Following ethanol precipitation, the precipitated nucleic acids were dried, and resuspended in DEPC treated distilled water. Secondary structures in the nucleic acids were disrupted by heating at 65° C. for 10 minutes, and the samples were immediately cooled on ice. cDNA was synthesized using 1 to 3 micrograms of total chimpanzee RNA from liver, or from nucleic acids (or RNA) extracted from 10 to 100 microliters of plasma. The synthesis utilized reverse transcriptase, and was in a 25 microliter reaction, using the protocol specified by the manufacturer, BRL. The primers for cDNA synthesis were those also utilized in the PCR reaction, described below. All reaction mixtures for cDNA synthesis contained 23 units of the RNAase inhibitor, RNASIN™ (Fisher/Promega). Following cDNA synthesis, the reaction mixtures were diluted with water, boiled for 10 minutes, and quickly chilled on ice.

The PCR reactions were performed essentially according to the manufacturer's directions (Cetus-Perkin-Elmer), except for the addition of 1 microgram of RNase A. The reactions were carried out in a final volume of 100 microliters. The PCR was performed for 35 cycles, utilizing a regimen of 37° C. (2 min), 72° C. (3 min), and 94° C. (1 min).

The primers for cDNA synthesis and for the PCR reactions were derived from the HCV cDNA sequences in either clone 81, clone 36, or clone 37b. (The HCV cDNA sequences of clones 81, 36, and 37b are shown in FIGS. 5, 6, and 7, respectively.) The sequences of the two 16-mer primers derived from clone 81 were:

5' CAA TCA TAC CTG ACA G 3' and

5' GAT AAC CTC TGC CTG A 3'.

The sequence of the primer from clone 36 was:

5' GCA TGT CAT GAT GTA T 3'.

The sequence of the primer from clone 37b was:

5' ACA ATA CGT GTG TCA C 3'.

In the PCR reactions, the primer pairs consisted of either the two 16-mers derived from clone 81, or the 16-mer from clone 36 and the 16-mer from clone 37b.

The PCR reaction products were analyzed by separation of the products by alkaline gel electrophoresis, followed by Southern blotting, and detection of the amplified HCV-cDNA sequences with a $^{32}$P-labeled internal oligonucleotide probe derived from a region of the HCV cDNA which does not overlap the primers. The PCR reaction mixtures were extracted with phenol/chloroform, and the nucleic acids precipitated from the aqueous phase with salt and ethanol. The precipitated nucleic acids were collected by centrifugation, and dissolved in distilled water. Aliquots of the samples were subjected to electrophoresis on 1.8% alkaline agarose gels. Single stranded DNA of 60, 108, and 161 nucleotide lengths were co-electrophoresed on the gels as molecular weight markers. After electrophoresis, the DNAs in the gel were transferred onto Biorad Zeta Probe™ paper. Prehybridization and hybridization, and wash conditions were those specified by the manufacturer (Biorad).

The probes used for the hybridization-detection of amplified HCV cDNA sequences were the following. When the pair of PCR primers were derived from clone 81, the probe was an 108-mer with a sequence corresponding to that which is located in the region between the sequences of the two primers. When the pair of PCR primers were derived from clones 36 and 37b, the probe was the nick-translated HCV cDNA insert derived from clone 35. The primers are derived from nucleotides 155–170 of the clone 37b insert, and 206–268 of the clone 36 insert. The 3'-end of the HCV cDNA insert in clone 35 overlaps nucleotides 1–186 of the insert in clone 36; and the 5'-end of clone 35 insert overlaps nucleotides 207–269 of the insert in clone 37b. (Compare FIGS. 6, 17 and 7.) Thus, the cDNA insert in clone 35 spans part of the region between the sequences of the clone 36 and 37b derived primers, and is useful as a probe for the amplified sequences which include these primers.

Analysis of the RNA from the liver specimens was according to the above procedure utilizing both sets of primers and probes. The RNA from the liver of the three chimpanzees with NANBH yielded positive hybridization results for amplification sequences of the expected size (161 and 586 nucleotides for 81 and 36 and 37b, respectively), while the control chimpanzees yielded negative hybridization results. The same results were achieved when the experiment was repeated three times.

Analysis of the nucleic acids and RNA from plasma was also according to the above procedure utilizing the primers and probe from clone 81. The plasmas were from two chimpanzees with NANBH, from a control chimpanzee, and pooled plasmas from control chimpanzees. Both of the NANBH plasmas contained nucleic acids/RNA which yielded positive results in the PCR amplified assay, while both of the control plasmas yielded negative results. These results have been repeatedly obtained several times.

Defective viruses have been known to occur in RNA viruses. By using PCR technology it is possible to design primers to amplify sequences of the HCV genome. By analysis of the amplified products, it is expected to be able to identify both defective versions of the viral genome as well as wild-type viral species. Accordingly, using two primers based on known HCV sequence, one can predict accurately the expected size of the PCR product. Any larger species observed by gel electrophoresis and hybridization analysis could represent potential variant genomes. Alternatively, any smaller species observed in this fashion might represent defective agents. Analyses of these types would be useful in confirming the exact origin of the known HCV sequence, whether it is indeed a wild-type viral sequence or a defective genome. Techniques and methods for these analyses are well known in the art and have been previously described. This methodology will enable one skilled in the art to obtain related (wild-type or defective) forms of the viral genome.

Detection of Sequences in Captured Particles Which When Amplified by PCR Hybridize to HCV cDNA Derived from Clone 81

The RNA in captured particles was obtained as described below. The analysis for sequences which hybridize to the HCV cDNA derived from clone 81 was carried out utilizing the PCR amplification procedure, as described supra., except that the hybridization probe was a kinased oligonucleotide derived from the clone 81 cDNA sequence. The results showed that the amplified sequences hybridized with the HCV cDNA probe.

Particles were captured from HCV infected chimpanzee plasma using polystyrene beads coated with an immunopurified antibody directed against the polypeptide encoded in clone 5-1-1. The procedure for producing the immunopurified antibody preparation is described in U.S. Ser. No. 07/456,637, which is commonly owned by the herein assignee, and which is incorporated herein by reference. Briefly, the HCV polypeptide encoded within clone 5-1-1 was expressed as a fusion polypeptide with superoxide dismutase (SOD). This was accomplished by subcloning the clone 5-1-1 cDNA insert into the expression vector pSODcf1 (Steimer et al. (1986)). DNA isolated from pSODcf1 was treated with BamHI and EcoRI, and the following linker was ligated into the linear DNA created by the restriction enzymes:

5' GAT CCT GGA ATT CTG ATA AGA
CCT TAA GAC TAT TTT AA 3'

After cloning, the plasmid containing the insert was isolated. Plasmid containing the insert was restricted with EcoRI. The HCV cDNA insert in clone 5-1-1 was excised with EcoRI, and ligated into this EcoRI linearized plasmid DNA. The DNA mixture was used to transform *E. coli* strain D1210 (Sadler et al. (1980)). Recombinants with the 5-1-1 cDNA in the correct orientation for expression of the ORF were identified by restriction mapping and nucleotide sequencing. Recombinant bacteria from one clone were induced to express the SOD-NANB$_{5-1-1}$ polypeptide by growing the bacteria in the presence of IPTG. The fusion polypeptide was purified from the recombinant *E. coli* by differential extraction of the cell extracts with urea, followed by chromatography on anion and cation exchange columns. The purified SOD-NANB$_{5-1-1}$ polypeptide was attached to a nitrocellulose membrane. Antibody in samples of HCV infected serum was absorbed to the matrix-bound polypeptide. After washing to remove non-specifically bound materials and unbound materials, the bound antibody was released from the bound polypeptide.

cPCR Method to Detect HCV RNA in Liver and in Serum from Individuals with NANBH.

The reliability and utility of a modified form of the PCR assay, i.e., a cPCR assay, for detecting HCV infection was determined by performing the assay on total liver RNA and on serum from infected individuals. In the cPCR assay, putative viral RNA in the sample is reverse transcribed into cDNA with reverse transcriptase; a segment of the resulting cDNA is then amplified utilizing a modified version of the PCR technique described by Saiki et al. (1986). The primers for the cPCR technique are derived from HCV RNA, which can be identified by the family of HCV cDNAs provided herein. Amplified product corresponding to the HCV-RNA is detected utilizing a probe derived from the family of HCV cDNAs provided herein.

The cPCR/HCV assay used in these studies were performed utilizing the following methods for the preparation of RNA, the reverse transcription of the RNA into cDNA, the amplification of specific segments of the cDNA by PCR, and the analysis of the PCR products.

RNA was extracted from liver utilizing the guanidium isothiocyanate method for preparing total RNA described in Maniatis et al. (1982).

In order to isolate total RNA from plasma, the plasma was diluted five- to ten-fold with TENB (0.1M NaCl, 50 mM Tris-HCl, pH 8.0, 1 mM EDTA) and incubated in a Proteinase K/SDS solution (0.5% SDS, 1 mg/ml Proteinase K, 20 micrograms/ml Poly A carrier) for 60 to 90 minutes at 37° C. The samples were extracted once with phenol (pH 6.5), the resulting organic phase was re-extracted once with TENB containing 0.1% SDS, and the aqueous phases of both extractions were pooled and extracted twice with an equal volume of phenol/CHCl$_3$/isoamyl alcohol [1:1(99:1)]. The resulting aqueous phases were extracted with an equal volume of ChCl$_3$/isoamyl alcohol (99:1) twice, and ethanol precipitated using 0.2M sodium acetate, pH 6.5, and 2.5 volumes of 100% ethanol; precipitation was overnight at −20° C.

The cDNA used as a template for the PCR reaction was prepared utilizing the designated samples for preparation of the corresponding cDNAs. Each RNA sample (containing either 2 micrograms of heat denatured total chimpanzee liver RNA, RNA from 2 microliters of plasma, or 10% of the RNA extracted from 10 mm×4 mm cylindrical human liver biopsies) was incubated in a 25 microliter reaction containing 1 micromolar of each primer, 1 millimolar of each deoxyribonucleotide triphosphate (dNTP), 50 millimolar Tris-HCL, pH 8.3, 5 millimolar MgCl$_2$, 5 millimolar dithiothreitol (DTT), 73 millimolar KCl, 40 units of RNase inhibitor (RNASIN), and 5 units of AMV reverse transcriptase. The incubation was for 60 minutes at 37° C.

Following cDNA synthesis, the reactions were diluted with 50 microliters of deionized water (DIW), boiled for 10 minutes, and cooled on ice.

Amplification of a segment of the HCV cDNA was performed utilizing two synthetic oligomer 16-mer primers whose sequences were derived from HCV cDNA clones 36 (anti-sense) and 37b (sense). The sequence of the primer from clone 36 was:

5' GCA TGT CAT GAT GTA T 3'.

The sequence of the primer from clone 37b was:

5' ACA ATA CGT GTG TCA C 3'.

The primers were used at a final concentration of 1 micromolar each. In order to amplify the segment of HCV cDNA which is flanked by the primers, the cDNA samples were incubated with 0.1 microgram of RNAse A and the PCR reactants of the Perkin Elmer Cetus PCR kit (N801-0043 or N801-0055) according to the manufacturer's instructions. The PCR reaction was performed for either 30 cycles or 60 cycles in a Perkin Elmer Cetus DNA thermal cycler. Each cycle consisted of a 1 minute denaturation step at 94° C., an annealing step of 2 minutes at 37° C., and an extension step of 3 minutes at 72° C. However, the extension step in the final cycle (30 or 60) was 7 minutes rather than 3 minutes. After amplification the samples were extracted with an equal volume of phenol:chloroform (1:1), followed by extraction with an equal volume of chloroform, and then the samples were precipitated with ethanol containing 0.2M sodium acetate.

The cPCR products were analyzed as follows. The products were subjected to electrophoresis on 1.8% alkaline agarose gels according to Murakawa et al. (1988), and transferred onto Zeta™ Probe paper (BioRad Corp.) by blotting gels overnight in 0.4M NaOH. The blots were neutralized in 2×SSC (1×SSC contains 0.15M NaCl, 0.015M sodium citrate), prehybridized in 0.3M NaCl, 15 mM sodium phosphage buffer, pH 6.8, 15 mM EDTA, 1.0% SDS, 0.5% nonfat milk (Carnation Co.), and 0.5 mg/ml sonicated denatured salmon sperm DNA. The blots to be analyzed for HCV cDNA fragments were hybridized to a $^{32}$P-labeled probe generated by nick translation of the HCV cDNA insert sequence in clone 35, described in U.S. Ser. No. 07/456,637. After hybridization, the blots were washed in 0.1×SSC (1×SSC contains 0.15M NaCl, 0.01M Na citrate) at 65° C., dried, and autoradiographed. The expected product size is 586 nucleotides in length; products which hybridized with the probe and migrated in the gels in this size range were scored as positive for viral RNA.

As a control, cPCR primers designed to amplify alpha-1 anti-trypsin mRNA was performed to verify the presence of RNA in each sample analyzed. The coding region of the alpha-1 anti-trypsin gene is described in Rosenberg et al. (1984). Synthetic oligomer 16-mer primers designed to amplify a 365 nucleotide fragment of the coding region of the alpha-1 antitrypsin gene were derived from nucleotides 22–37 (sense) and nucleotides 372–387 (antisense). The PCR products were detected using a $^{32}$P nick-translated probe which lies between, and not including, the cDNA/PCR primer sequences.

Due to the extreme sensitivity of the PCR reaction, all samples were run a minimum of three times. All false positive signals were eliminated when the following precautions were taken: 1) eliminating aerosols by using screw capped tubes with rubber O-ring seals; 2) pipetting with Ranin Microman™ positive displacement pipetters with disposable pistons/capillaries; and 3) selecting the oligonucleotide sequences for the cDNA and PCR primers from two non-contiguous cDNA clones.

Detection of HCV RNA in Liver Samples by a cPCR Method

The cPCR assay was performed on total RNA isolated from livers of three chimpanzees experimentally infected with a NANBH agent, and from liver biopsies of Italian patients diagnosed as having chronic NANBH.

Figure 8A:
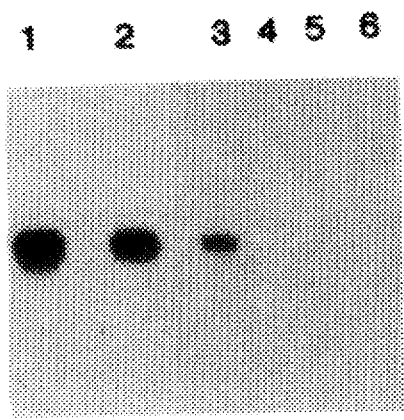
FIG. 8 shows autoradiographs of the HCV cPCR assay on RNA derived from liver samples of chimpanzees with NANBH (FIG. 8A) and on Italian patients with NANBH (FIG. 8B).

FIG. 8A shows the results of the cPCR assay using 1 microgram of each preparation of total liver RNA. The RNA was isolated from liver samples of a chimpanzee in the chronic phase of NANBH (910) (lane 1), two chimpanzees in the acute phase of infection (1028 and 508) (lanes 2 and 3, respectively). PCR was performed on the samples in lanes 1–3 for 30 cycles and the autoradiogram of the blot containing those lanes was exposed for 5 hours. cDNA from 1 microgram of total RNA from acutely infected animal 1028 (lane 4), and three uninfected chimpanzees (lanes 5–7), were amplified for 60 cycles and the autoradiograms containing those lanes were exposed for 7 days. $^{32}P$ labeled MspI-digested pBR322 DNA served as markers on all the autoradiograms. It may be seen from the results that cDNA corresponding to HCV RNA was seen only in the samples from chimpanzees with NANBH, whether acute or chronic (lanes 1, 3, and 4). The cPCR products in these lanes migrated between marker fragments of 527 and 622 nucleotides (not shown).

Figure 8B:
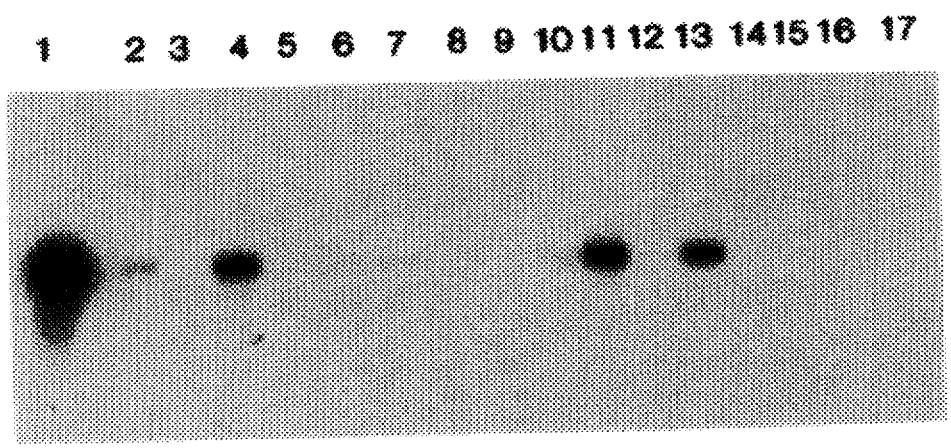

FIG. 8B shows the results of the cPCR assay using 10% of the RNA extracted from 10 mm×4 mm liver biopsy cylinders from 15 chronic NANB patients (lanes 1–15), one patient with cryptogenic liver disease (lane 16) and one control sample from a patient with chronic Hepatitis B (lane 17). Amplification by PCR was for 30 cycles and the autoradiogram for the blots were exposed for 4 days, except that lane 1 was exposed for 15 hours. As seen from the results, 9/15 (60%) of the human samples were positive for HCV RNA (lanes 1,2,4,6,7,10–13). One patient diagnosed with cryptogenic liver disease (lane 16) and one patient with a chronic HBV infection (lane 17) were repeatedly negative in the cPCR assay.

Comparison of the HCV/cPCR Assay on Human Liver Biopsies and RIA of Serum Using HCV C100-3 Polypeptide SOD/HCV C100-3 polypeptide (also called C100) is a recombinant fusion polypeptide which contains 363 viral amino acids. The polypeptide is useful for detecting antibodies to HCV (See Kuo et al. (1989)).

Radioimmune assay using C100 was performed on the sera collected from the same 17 human patients whose liver samples were subjected to HCV/cPCR assay as described in supra. The sera was collected on the same day as the liver biopsies. The assay was performed essentially as described in U.S. Ser. No. 07/456,637, which is commonly owned and incorporated herein by reference. Briefly, Microtiter plates (Immulon 2, Removeawell strips) were coated with 0.1 microgram of purified C100. The coated plates were incubated for 1 hour at 37° C. with the serum samples (100 microliters of a 1:100 dilution) or appropriate controls. After incubation, the unbound material was removed, the plates were washed, and complexes of human antibody-C100 were detected by incubation with $^{125}I$-labeled sheep anti-human immunoglobulin. Unbound labeled antibody was removed by aspiration, and the plates were washed. The radioactivity in individual wells was determined.

The results of the RIA showed that sixty-seven percent of these samples were positive for anti-C100 antibodies. Sera from the patient diagnosed with cryptogenic liver disease was positive for anti-C100 antibodies, although the levels of viral RNA were undetectable in the patient's liver in this sample. The level of correlation between the presence of anti-C100 antibodies and HCV RNA was seventy percent; two patients who were negative for antibodies by RIA had significant levels of HCV RNA in their livers (data not shown).

The results indicate that virus is frequently present in the liver of patients with circulating anti-C100 antibodies, and confirms claims that the presence of anti-C100 antibodies accurately reflects exposure to HCV. Moreover, taken together, these results indicate that HCV of this type accounts for NANBH in at least 75% of the patients in this study, and that the predominant strain of HCV in Italy appears to be closely related to the strain of HCV prevalent in the United States.

HCV/cPCR Assay of Sera: Detection of Viral RNA in Acute Phase Infection in Chimpanzees The temporal relationship between the display of liver damage, the presence of HCV RNA, and the presence of anti-HCV antibodies was monitored in serum from two experimentally infected chimpanzees with NANBH (nos. 771 and 910). Liver damage was determined by alanine amino transferase (ALT) levels; the presence of HCV RNA was determined by the HCV cPCR assay described above; anti-HCV antibodies were detected utilizing the C100 RIA.

The HCV/cPCR analysis was performed on RNA extracted from 1 microliter of chimpanzee plasma. Serum was taken from chimpanzee 771 on days 25, 32, 70 and 88 post-infection; cPCR was performed for 30 cycles and the autoradiogram was exposed for 18 days. Serum was taken from chimpanzee 910 on days 11, 28, and 67 post-infection; cPCR was performed for 60 cycles and the autoradiogram was exposed for 5 days.

The results of the assays are shown in FIG. 9A for chimpanzee 771, and FIG. 9B for chimpanzee 910. From a comparison of FIGS. 9A and 9B, it appears that an early, well defined peak of ALT values during acute hepatitis correlates with the presence of viral RNA in the infected individual.

The data also indicate that the presence of HCV RNA, which is indicative of a state of viremia, precedes the presence of anti-HCV antibodies. Chimpanzee 771 (FIG. 9A) exhibited a clearly defined acute episode of post-transfusion NANBH at 28 days, as characterized by an initial peak of ALT levels. HCV RNA was detected in the serum collected at day 25, and at day 32. However, during this acute phase, anti-HCV antibodies were absent. In contrast, at day 70 HCV RNA was below the experimental level of detection, and anti-HCV antibodies were rising. At day 88, HCV RNA remained undetectable, while anti-HCV antibodies were significantly increased over that of day 70.

The results obtained from the sera of chimpanzee 910 were somewhat similar in pattern, although the time of HCV antibodies induced by the infection were not detected during the acute phase of the disease, which extended to at least day 67; the anti-HCV antibodies detected by RIA at day 11 were due to passive immunization of animal 910 with antibodies from the plasma used to inoculate the animal. Anti-HCV antibodies were found in chimpanzee 910 serum during the later, chronic phase of the infection (data not shown).

It should be noted that low ALT values in plasma from individuals with chronic NANBH do not necessarily correlate with weak virus production. A pool of 17 different plasma samples taken from chimpanzee 910 over a period of two to three and one-half years post inoculation was monitored for ALT levels and for HCV RNA. The ALT values of the samples did not exceed 45 mU/ml; nevertheless, titration studies indicated high titers of HCV ($3 \times 10^6$ CID/ml). cPCR was carried out for 30 cycles, and the autoradiogram was exposed for 15 hours; the cPCR analysis clearly showed the presence of viral RNA (data not shown).

HCV/cPCR Assay of Sera: Detection of Viral RNA in Acute Phase Infection in Humans Plasma from a human surgical patient collected during early acute NANBH was examined for HCV RNA and for anti-HCV antibodies, utilizing the HCV/cPCR assay and C100-RIA, respectively. The HCV/cPCR assay was conducted utilizing 1 microliter of plasma from the patient, and from four human controls with known pedigrees; cPCR was performed for thirty cycles, and after hybridization and washing the autoradiogram was exposed for eight hours.

The results showed that the serum collected from the surgical patient during the acute phase of infection contained a high level of viral RNA, and that anti-HCV antibodies were not detectable by the C100-RIA (data now shown). (The acute phase plasma from the surgical patient was known to have a high titer of NANBH infectious agent [$10^{6.5}$ CID/ml, as determined by Feinstone et al. (1981); Feinstone et al. (1983)]). It should be noted, however, that this patient did sero-covert to anti-HCV antibodies by the C100-RIA approximately 9 months after infection. The serum from the pedigreed human control plasmas were negative in both the HCV/cPCR assay and C100-RIA.

Sensitivity of HCV/cPCR Assay

Figure 12:
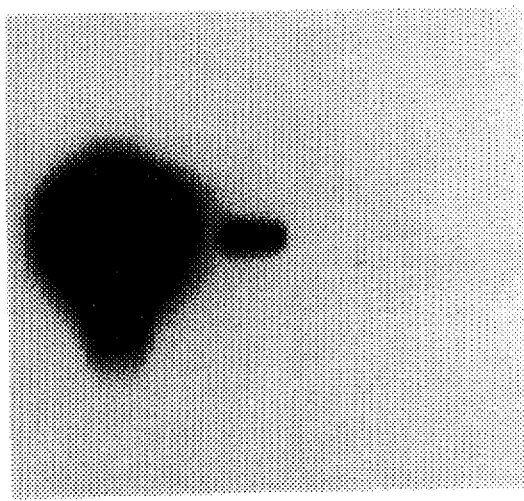
FIG. 12 is an autoradiograph showing the labeled amplified products of approximately 300, 30, and 3 CID of HCV genomes.

The sensitivity of the HCV/cPCR assay was determined by analyzing ten-fold serial dilutions of a plasma pool of known titer. The chimpanzee plasma had a titer of ~$3 \times 10^5$ CID/ml, and RNA was extracted from ten-fold dilutions of 1 microliter of the plasma. cPCR was performed for 30 cycles, and after hybridization and washing, the autoradiogram was exposed for 15 hours. The cPCR products resulting from amplification of ~300, ~30, and ~3 CID of HCV genomes are shown in lanes 1-3, respectively of FIG. 12. The samples in lanes 1 and 2 were detectable on autoradiograms exposed for 2 hours.

Since the average titer of HCV in infected individuals is believed to be between approximately 100 to 10,000 CID/ml of plasma, this data suggests that the HCV/cPCR assay may be clinically useful.

HCV/cPCR Assay for Variant HCV Strains

Primers, consisting of a set of oligomer 44-mers and a set of oligomer 45-mers, were designed to amplify strains of HCV which are similar or identical to the HCV isolate from which the cDNA sequence in FIG. 10 is derived. The premise underlying the design of these primers is our discovery that HCV is a Flavi-like virus. Members of the Flaviviridae family, when compared to HCV, have two major conserved sets of amino acid sequences, TATPPG and QRRGR, in the putative NS3 region of these viruses. Several other smaller sets may be seen, for example, GDD in the putative NS5 region. Other sets are determinable by comparison of the known amino acid sequences with that of HCV. This information was deduced from the sequences for several members of Flaviviridae which have been described, including Japanese Encephalitis Virus (Sumiyoshi et al. (1987)), Yellow Fever Virus (Rice et al. (1985)), Dengue Type 2 Virus (Hahn et al. (1988)), Dengue Type 4 Virus (Mackow (1987)), and West Nile Virus (Castle et al. (1986)). The conserved amino acid sequences and codon utilization are in the table immediately following.

| Conserved Amino ACid (A.A.) Sequences among Flaviviruses and HCV ||||||
|---|---|---|---|---|---|
| | | A.A. = |||||
| Virus | # of 1st A.A. | T  A | T | P  P | G |
| HCV | 1348 | 5' ACC GCC | ACC | CCT CCG | GGC 3' |
| Yellow Fever | 1805 | ACA GCC | ACA | CCG CCT | GGG |
| West Nile | 1818 | ACG GCA | ACG | CCA CCC | GGG |
| Dengue-4 | 1788 | ACC GCA | ACC | CCT CCC | GGA |
| JEV | 1957 | ACA GCG | ACC | CCG CCT | GGA |
| HCV sense primer (44mer) = | | 5'...ACC GCC | ACC | CCX CC 3' | (X = A,T,C,G) |
| | | A.A = |||||
| Virus | # of 1st A.A. | Q  R | R | G  R | |
| HCV | 1486 | 5' CAA CGT | CGG | GGC AGG 3' | |
| Yellow Fever | 1946 | CAA AGG | AGG | CGG CGC | |
| West Nile | 1959 | CAG CGG | AGA | GGA CGC | |
| Dengue-4 | 1929 | CAG AGA | AGA | GGG CGA | |
| JEV | 1820 | CAA CGG | AGG | GGC AGA | |
| HCV antisense primer (45mer) = | | 3' GTX GCA | GCC | CCG TCC...5' | (X = T,C) |

Note: the primer sequence was chosen to minimize the number of nucleotide degeneracies at the 3' end of the primer sequence and maximize of the number of nucleotides at the 3' end of each primer which exactly match any of the possible nucleotide sequences, or the complement thereof, encoding the conserved amino acids indicated above.

The 44-mer and 45-mer oligomer primers were designed so that the sequences encoding these amino acids were incorporated within the primer. Moreover, they contain degeneracies at the 3'-end of each primer, and are derived from two different regions of the HCV genome which are present in clone 40b (See FIG. 11), and which are derived from the region encoding putative NS3 of HCV. The formulae for the oligonucleotide primers in the sets are:

5' GAC TGC GGG GGC GAG ACT GGT TGT GCT CGC
ACC GCC ACC CCX CC 3' where X is A, T, G, or C; and

5' TCT GTA GAT GCC TGG CTT CCC CCT GCC AGT CCT GCC CCG ACT YTG 3' where Y is T or C.

The HCV/cPCR assay was carried out utilizing these primers to amplify HCV RNA in chimpanzee 910 plasma. The assay method was essentially as described in Section supra., except that the 44-mer and 45-mer sets of oligomer primers were substituted for the primers derived from clone 36 and clone 37b. In addition, detection of amplified HCV cDNA was by hybridization with a probe derived from clone 40a, the sequence of which is shown in FIG. 13.

The probe was prepared by amplifying the segment of clone 40a indicated in the figure utilizing the PCR method described supra., and 18-mer primers containing the following sequences:

5' GAG ACA TCT CAT CTT CTG 3' and

5' GAG CGT GAT TGT CTC AAT 3'.

After amplification, the probe preparation was labeled with $^{32}$P by nick translation.

FIG. 14 shows an autoradiograph of the Southern blots probed with the sequence derived from Clone 40a. $^{32}$P labeled MspI digested pBR322 DNA fragments served as markers (lane 1). The predicted size of the PCR product resulting from amplification using these primers is 490 nucleotides (nt). Duplicate reactions are shown in lanes 2 and 3.

Analysis for Variants of the 5'-Region of HCV

Based upon the Flavivirus model, the 5'-region HCV cDNA which is flanked by the regions represented in clones ag30a and k9-1 encodes a segment of putative envelope and/or matrix protein(s) (E/M). Serum obtained from the chimpanzee from which the HCV cDNA "c" library, was constructed was analyzed by HCV/cPCR to determine whether variants within this target region were present.

The HCV/cPCR assay was performed essentially as described supra., except for the primers and probes used. FIG. 15 shows the relationship of the primers and probes, and clones from which they were derived, to that of the target region of HCV cDNA. One set of PCR primers, ag30a16A and K91Env16B, were derived from clones ag30a and k9-1, which are upstream and downstream, respectively, of the target sequence. The expected size of the cPCR product primed by ag30a16A and K91Env16B is 1.145 kb based upon the confirmed sequence of HCV cDNA. Two other sets of PCR primers covering the region amplified using ag30a16A and K91Env16B, and overlapping each other were also used for PCR amplification of HCV RNA in the serum. Thus, in this case the PCR reactions were run using as one set of primers ag30a16A and CA156e16B, and as the second set of primers CA156e16A and k91Env16B. The expected PCR product sizes for these pairs were 615 nucleotides (NT) and 683 NT, respectively. The table immediately following lists the primer, the clone from which it was derived, and the primer sequence.

TABLE

| Primer | Clone | Sequence |
| --- | --- | --- |
| ag30a16A | ag30a | 5' CTC TAT GGC AAT GAG G 3' |
| K91Env16B | k9-1 | 5' CGT TGG CAT AAC TGA T 3' |
| CA156e16B | 156 | 5' CGA CAA GAA AGA CAG A 3' |
| CA156e16A | 156 | 5' AGC TTC GAC GTC ACA T 3' |
| CA216a16A | 216 | 5' TGA ACT ATG CAA CAG G 3' |
| CA216a16B | 216 | 5' GGA GTG TGC AGG ATG G 3' |
| CA84a16A | 84 | 5' AAG GTT GCA ATT GCT C 3' |
| CA84a16B | 84 | 5' ACT AAC AGG ACC TTC G 3' |

The probes for all of the HCV/cPCR products consisted of $^{32}$P labeled sections of HCV cDNA which had been prepared by PCR amplification of a region of clone 216 (using CA216a16A and 216a16B as primers), and of clone 84 (using CA84a16A and CA84a16B as primers); $^{32}$P was introduced into the PCR products by nick translation. These probes did not overlap the primers used in the HCV/cPCR reactions.

Figure 16:
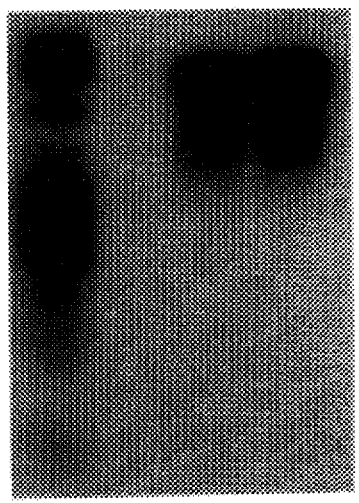
FIG. 16 is an autoradiograph showing amplified products extended from primers derived from conserved regions of the HCV genome.

FIG. 16 shows an autoradiograph of a Southern blot in which the HCV/cPCR products were hybridized with the $^{32}$P-labeled probes. The HCV/cPCR product extended from primers ag30a16A and K91Env16B (lane 1) was approximately 1.1 Kb; no other PCR products were observed in a 15 hour exposure. The HCV products extended from the primer sets ag30a15A/CA156e16B (lane 2) and CA156e16A/K91Env16B (lane 3) were approximately 625 NT and approximately 700 NT, respectively. The size of the PCR products were determined by comparison with the relative migrations of fragments resulting from the digestion of pBR322 with MspI and of PhiX 174 digested with HaeIII (lane 5).

The above study will detect insertions or deletions as small as approximately 20 NT to 50 NT and DNA rearrangements altering the size of the target DNA. The results in FIG. 16 confirm that there is only 1 major species of cDNA derived from the E/M region of the HCV in the chimpanzee serum.

Amplification for Cloning of HCV cDNA Sequences Utilizing the PCR and Primers Derived from Conserved Regions of Flavivirus Genomic Sequences Our discovery that HCV is a flavi-like virus, allows a strategy for cloning uncharacterized HCV cDNA sequences utilizing the PCR technique, and primers derived from the regions encoding conserved amino acid sequences in flaviviruses. Generally, one of the primers is derived from a defined HCV genomic sequence, and the other primer which flanks a region of unsequenced HCV polynucleotide is derived from a conserved region of the flavivirus genome. The flavivirus genomes are known to contain conserved sequences within the NS1, and E polypeptides, which are encoded in the 5'-region of the flavivirus genome. Thus, to isolate cDNA sequences derived from putatively comparable regions of the HCV genome, upstream primers are designed which are derived from the conserved sequences within these flavivirus polypeptides. The downstream primers are derived from an upstream end of the known portion of the HCV cDNA.

Because of the degeneracy of the code, it is probable that there will be mismatches between the flavivirus probes and the corresponding HCV genomic sequence. Therefore a strategy which is similar to the one described by Lee (1988) is used. The Lee procedure utilizes mixed oligonucleotide primers complementary to the reverse translation products of an amino acid sequence; the sequences in the mixed primers takes into account every codon degeneracy for the conserved amino acid sequence.

Three sets of primer mixes are generated, based on the amino acid homologies found in several flaviviruses, including Dengue-2,4 (D-2,4), Japanese Encephalitis Virus (JEV), Yellow Fever (YF), and West Nile Virus (WN). The primer mixture derived from the most upstream conserved sequence (5'-1), is based upon the amino acid sequence gly-trp-gly, which is part of the conserved sequence asp-arg-gly-trp-gly-aspN found in the E protein of D-2, JEV, YF, and WN. The next primer mixture (5'-2) is based upon a downstream conserved sequence in E protein, phe-asp-gly-asp-ser-tyr-ileu-phe-gly-asp-ser-tyr-ileu, and is derived from phe-gly-asp; the conserved sequence is present in D-2, JEV, YF, and WN. The third primer mixture (5'-3), is based on the amino acid sequence arg-ser-cys, which is part of the conserved sequence cys-cys-arg-ser-cys in the NS1 protein of D-2, D-4, JEV, YF, and WN. The individual primers which form the mixture in 5'-3 are shown in FIG. 13. In addition to the varied sequences derived from conserved region, each primer in each mixture also contains a constant region at the 5'-end which contains a sequence encoding sites for restriction enzymes, HindIII, MboI, and EcoRI.

The downstream primer, ssc5h20A, is derived from a nucleotide sequence in clone 5h, which contains HCV cDNA with sequences with overlap those in clones 14i and 11b. The sequence of ssc5h20A is

5' GTA ATA TGG TGA CAG AGT CA 3'.

An alternative primer, ssc5h34A, may also be used. This primer is derived from a sequence in clone 5h, and in addition contains nucleotides at the 5'-end which create a restriction enzyme site, thus facilitating cloning. The sequence of ssc5h34A is

5' GAT CTC TAG AGA AAT CAA TAT GGT GAC AGA GTC A 3'.

The PCR reaction, which was initially described by Saiki et al. (1986), is carried out essentially as described in Lee et al. (1988), except that the template for the cDNA is RNA isolated from HCV infected chimpanzee liver, or from viral particles isolated from HCV infected chimpanzee serum. In addition, the annealing conditions are less stringent in the first round of amplification (0.6M NaCl, and 25° C.), since the part of the primer which will anneal to the HCV sequence is only 9 nucleotides, and there could be mismatches. Moreover, if ssc5h34A is used, the additional sequences not derived from the HCV genome tend to destabilize the primer-template hybrid. After the first round of amplification, the annealing conditions can be more stringent (0.066M NaCl, and 32° C.–37° C.), since the amplified sequences now contain regions which are complementary to, or duplicates of the primers. In addition, the first 10 cycles of amplification are run with Klenow enzyme I, under appropriate PCR conditions for that enzyme. After the completion of these cycles, the samples are extracted, and run with Taq polymerase, according to kit directions, as furnished by Cetus/Perkin-Elmer.

After the amplification, the amplified HCV cDNA sequences are detected by hybridization using a probe derived from clone 5h. This probe is derived from sequences upstream of those used to derive the primer, and does not overlap the sequences of the clone 5h derived primers. The sequence of the probe is 5' CCC AGC GGC GTA CGC GCT GGA CAC GGA GGT GGC CGC GTC GTG TGG CGG TGT TGT TCT CGT CGG GTT GAT GGC GC 3'.

Detection of HCV RNA in Plasma Using HCV/cPCR, Using Primers and Probes Derived from the 5'-Region of HCV RNA Extraction of HCV RNA from plasma Frozen plasma was thawed in a P3 hood. A 0.2 ml aliquot of digestion mix (100 millimolar Tris-HCl, 2 millimolar EDTA, 200 millimolar NaCl, 20 microgram/milliliter MS2 RNA, 0.5% SDS, and 2 milligram/milliliter Proteinase K, pH 8) was added to a 2 milliliter microfuge tube and prewarmed to 37° C. The plasma (0.2 milliliter) was then added, and the mixture allowed to incubate at 60° C. for 1 hour. Next, phenol (0.4 milliliter) was added, and the mixture vortexed 3× for 30 seconds, allowing 30 seconds between each vortexing. The mixture was then centrifuged for 5 minutes, and the aqueous phase recovered. The organic phase was back-extracted with 0.1 milliliter TES, and the pooled aqueous phases extracted 2× with 1 volume phenol/chloroform/IAA, then with 1 volume chloroform. To the extract was added 1 microliter (2 micrograms) glycogen (Boehringer Mannheim Corp.) and 25 microliter NaOAc (3 molar, pH 5.4) and 1.25 ml cold EtOH, and the product frozen on dry ice and spun 10 min. The pellet was dissolved in 100 microliter distilled water, and 5 microliters NaOAc (pH 5.4) added with 250 microliters cold EtOH. The solution was frozen and spun again, and the resulting pellet dissolved in 10 microliters $dH_2O$.

cDNA Synthesis

In order to synthesize cDNA from the extracted RNA, initially 5 microliters of the dissolved RNA was incubated with 4 microliters water and 1 microliter (1 microgram or 166 pmols of 18-mer) of RT primer. The incubation was at 70° C. for 3 minutes, followed by chilling on ice. The sequence of the RT primer was:

5' CCC AAC ACT ACT CGG CTA 3'.

After the initial incubation, the following were added to the incubation mixture: 10 microliters of 5× first strand buffer (250 mM Tris HCl, pH 8.3, 375 mM KCl, 15 mM $MgCl_2$, 50 mM dithiothreitol); 2.5 microliters deoxynucleoside triphosphates (10 mM each); 2.5 microliters reverse transcriptase (MMLV from BRL, 200 units per microliter), and distilled water to bring the volume to 50 microliters. The mixture was incubated at 37° C. for 1 hour, heated at 90° C. for 3 minutes, and chilled on ice.

PCR Amplification

PCR amplification of the HCV cDNA produced above was conducted using the control and test reagents listed below, in the Table. In the Table, "RNA" indicates a control sample in which the RNA was extracted from an individual which was uninfected with HCVl; this sample was carried through the steps of cDNA synthesis and PCR amplification. "cDNA" indicates a control sample which was carried through the steps of cDNA synthesis and PCR amplification; however, in this case the aliquot of RNA was replaced with water during cDNA synthesis. "Template⁻" was a control for the PCR reaction from which the template was omitted. "Sample" indicates the serum which was tested for the presence of HCV RNA.

TABLE

|             | RNA (ul) | cDNA (ul) | Template⁻ (ul) | Sample (ul) |
|-------------|----------|-----------|----------------|-------------|
| water       | 100.0    | to 100.0  | to 100.0       | to 100.0    |
| 10x buffer  | 10.0     | 10.0      | 10.0           | 10.0        |
| dNTPs       | 16.0     | 16.0      | 16.0           | 16.0        |
| primer 1    | 0.5      | 0.5       | 0.5            | 0.5         |
| primer 2    | 0.5      | 0.5       | 0.5            | 0.5         |
| template    | 2.5      | 2.5       | —              | 2.5         |
| Taq Pol 0.3 | 0.5      | 0.5       | 0.5            | 0.5         |

Primer 1 and Primer 2 were 0.5 micrograms/microliter and 0.42 micrograms/microliter, respectively, and had the following sequences.

Primer 1: 5' ACC ATG AAT CAC TCC CCT GTG AGG AAC TAC 3'

Primer 2: 5' AGT CTT GCG GGG GCA CGC CCA AAT C 3'

These primers hybridize to a conserved region in the 5' end of the HCV genome. The samples contained 12.5 microliter serum equivalents of HCV cDNA. The amplification cycle conditions used were as follows:
35 cycles:

Melting—94° C. for 1.5 min

Annealing—60° C. for 2 min

Elongation—72° C. for 3 min
Final Elongation:

72° C. for 30 min
Soak at 4° C. until removed.

The amplified product was probed using a labeled DNA. The sequence of the probe was the following.

Probe: 5' TTT CTT GGA TCA ACC CGC TCA ATG CCT GGA 3'

The detection of amplified DNA which hybridized with the probe was as described in the Examples described supra.

Over 200 HCV sera-positive samples were examined by the above procedure. Only results in which the controls were negative were considered. In this case, all sera-positive samples were also positive in the PCR assay.

Probes Derived from the Putative "Core" Region of HCV RNA

An analysis of the nucleotide sequences of cDNAs to different HCV isolates shows that a high degree of sequence conservation exists in the region from about nucleotide 1 to about nucleotide 570, using the numbering system for nucleotides shown in FIG. 1. This region putatively encodes a "core" polypeptide of HCV. The consensus sequences for five different isolates from different geographic locations (Japan and the U.S.) is shown in FIG. 18, where HCV1 is the prototype HCV; the amino acids encoded in the large ORF of HCV1 are shown above the consensus nucleotide sequences. In the sequences shown in FIG. 18, HCV-JH is from a personal communication from Dr. Tetsu Miyamura (National Institute of Health of Japan), and JC-J1 and JC-J4 are from Mayumi et al. (1990). It may be seen in FIG. 18 that between the consensus sequences in the putative "core" region, there is at least 90% homology relative to the sequence in HCV1. In view of the high degree of homology in the region between nucleotides +1 to +571, probes to this area would be useful in screening for HCV positive biological specimens.

A set of label probes which may be used for the detection of HCV RNA from the region which putatively encodes an HCV "core" polypeptide are shown in FIG. 19. In FIG. 19, a "probe number" in the set includes a series of polynucleotides with heterogeneities indicated by the by the IUB Group Code listed in FIG. 19. The heterogeneities are to accomodate nucleotide sequence differences found in the consensus sequences of the different isolates. The regions of the HCV sequence to which the probes in the probe set of FIG. 19 are complementary are shown in FIG. 20, in which the nucleotide numbers correspond to the numbering in FIG. 1.

Industrial Applicability

The methods described herein, as well as the oligomers, both probes and primers, derived from HCV cDNA, and kits containing them, are useful for the accurate, relatively simple, and economic determination of the presence of HCV in biological samples, more particularly in blood which may be used for transfusions, and in individuals suspected of having HCV an infection. Moreover, these methods and oligomers may be useful for detecting an earlier stage of HCV infection than are immunological assays based upon the use of a recombinant HCV polypeptides. Also, an amplified polynucleotide hybridization assay detects HCV RNA in occasional samples which are anti-HCV antibody negative. Thus, the probes and primers described herein may be used amplified hybridization assays, in conjunction with an immunoassays based on HCV polypeptides to more completely identify infections due to HCV, and HCV-infected biological specimens, including blood.

The information provided herein allows the design of primers and/or probes which are derived from conserved regions of the HCV genome. The provision of these primers and probes makes available a general method which will detect variant HCV strains, and which will be of use in the screening of blood and blood products.

If the primers used in the method are derived from conserved regions of the HCV genome, the method should aid in the detection and/or identification of variant strains of HCV. This, in turn, should lead to the development of additional immunological reagents for the detection and diagnosis of HCV, as well as the development of additional polynucleotide reagents for detection and or treatment of HCV.

In addition, sets of primers and probes designed from the conserved amino acid sequences of Flaviviruses and HCV allow for a universal detection method for these infectious agents.

The following listed materials are on deposit under the terms of the Budapest Treaty with the American Type Culture Collection (ATCC), 12301 Parklawn Dr., Rockville, Md. 20852, and have been assigned the following Accession Numbers.

| lambda-gt11      | ATCC No. | Deposit Date |
|------------------|----------|--------------|
| HCV cDNA library | 40394    | 1 Dec. 1987  |
| clone 81         | 40388    | 17 Nov. 1987 |
| clone 91         | 40389    | 17 Nov. 1987 |
| clone 1-2        | 40390    | 17 Nov. 1987 |
| clone 5-1-1      | 40391    | 18 Nov. 1987 |

51

-continued

| lambda-gt11 | ATCC No. | Deposit Date |
|---|---|---|
| clone 12f | 40514 | 10 Nov. 1988 |
| clone 35f | 40511 | 10 Nov. 1988 |
| clone 15e | 40513 | 10 Nov. 1988 |
| clone K9-1 | 40512 | 10 Nov. 1988 |
| JSC 308 | 20879 | 5 May 1988 |
| pS356 | 67683 | 29 April 1988 |

In addition, the following deposits were made on 11 May 1989.

| Strain | Linkers | ATCC No. |
|---|---|---|
| D1210 (Cf1/5-1-1) | EF | 67967 |
| D1210 (Cf1/81) | EF | 67968 |
| D1210 (Cf1/CA74a) | EF | 67969 |
| D1210 (Cf1/35f) | AB | 67970 |
| D1210 (Cf1/279a) | EF | 67971 |
| D1210 (Cf1/C36) | CD | 67972 |
| D1210 (Cf1/13i) | AB | 67973 |
| D1210 (Cf1/C33b) | EF | 67974 |
| D1210 (Cf1/CA290a) | AB | 67975 |
| HB101 (AB24/C100 #3R) |  | 67976 |

The following derivatives of strain D1210 were deposited on 3 May 1989.

| Strain Derivative | ATCC No. |
|---|---|
| pCF1CS/C8f | 67956 |
| pCF1AB/C12f | 67952 |
| pCF1EF/14c | 67949 |
| pCF1EF/15e | 67954 |
| pCF1AB/C25c | 67958 |
| pCF1EF/C33c | 67953 |
| pCF1EF/C33f | 67050 |
| pCF1CD/33g | 67951 |
| pCF1CD/C39c | 67955 |
| pCF1EF/C40b | 67957 |
| pCF1EF/CA167b | 67959 |

The following strains were deposited on May 12, 1989.

| Strain | ATCC No. |
|---|---|
| Lambda gt11 (C35) | 40603 |
| Lambda gt10 (beta-5a) | 40602 |
| D1210 (C40b) | 67980 |
| D1210 (M16) | 67981 |

The following biological materials were deposited on Mar. 23, 1990.

| Material | ATCC No. |
|---|---|
| 5'-clone32 (in pUC18S) | 68276 |

Upon allowance and issuance of this application as a United States Patent, all restriction on availability of these deposits will be irrevocably removed; and access to the designated deposits will be available during pendency of the above-named application to one determined by the Commissioner to be entitled thereto under 37 CFR 1.14 and 35 USC 1.22. Moreover, the designated deposits will be maintained for a period of thirty (30) years from the date of deposit, or for five (5) years after the last request for the deposit; or for the enforceable life of the U.S. patent, whichever is longer. The deposited materials mentioned herein are intended for convenience only, and are not required to practice the present invention in view of the descriptions herein, and in addition these materials are incorporated herein by reference.

What is claimed is:

1. A purified preparation of an oligonucleotide, wherein the oligonucleotide is capable of selectively hybridizing to the genome of a hepatitis C virus (HCV), or its complement, relative to other viral agents, and further wherein the oligonucleotide comprises a contiguous sequence of at least 10 nucleotides fully complementary to either strand of the nucleotide residue sequence depicted in FIG. 1.

2. The purified preparation of claim 1 wherein the oligonucleotide comprises a contiguous sequence of at least 12 nucleotides fully complementary to either strand of the nucleotide residue sequence depicted in FIG. 1.

3. The purified preparation of claim 2 wherein the oligonucleotide is a primer for a DNA polymerase or a reverse transcriptase.

4. The purified preparation of claim 1 wherein the oligonucleotide comprises a contiguous sequence of at least 15 nucleotides fully complementary to either strand of the nucleotide residue sequence depicted in FIG. 1.

5. The purified preparation of claim 1 wherein the oligonucleotide comprises a contiguous sequence of at least 20 nucleotides fully complementary to either strand of the nucleotide residue sequence depicted in FIG. 1.

6. The purified preparation of claim 1 wherein the oligonucleotide is a primer for DNA polymerase or a reverse transcriptase.

7. The purified preparation of claim 1 wherein the contiguous sequence is a conserved HCV nucleotide sequence.

8. The purified preparation of claim 7 wherein the conserved sequence is located in the sequence of nucleotide numbers from the 5' terminus to 200 in FIG. 1.

9. The purified preparation of claim 7 wherein the conserved sequence is located in the sequence of nucleotide numbers from 4000 to 5000 in FIG. 1.

10. The purified preparation of claim 7 wherein the conserved sequence is located in the sequence of nucleotide numbers from 8000 to 9040 in FIG. 1.

11. The purified preparation of claim 7 wherein the conserved sequence is located in the sequence of nucleotide numbers from −318 to 174 in FIG. 1.

12. The purified preparation of claim 7 wherein the conserved sequence is located in the sequence of nucleotide numbers from 4056 to 4448 in FIG. 1.

13. The purified preparation of claim 7 wherein the conserved sequence is located in the sequence of nucleotide numbers from 4378 to 4902 in FIG. 1.

14. The purified preparation of claim 7 wherein the conserved sequence is located in the sequence of nucleotide numbers from 4042 to 4059 in FIG. 1.

15. The purified preparation of claim 7 wherein the conserved sequence is located in the sequence of nucleotide numbers from 4456 to 4470 in FIG. 1.

16. The purified preparation of claim 7 wherein the conserved sequence is located in the sequence of nucleotide numbers from 8209 to 8217 in FIG. 1.

17. The purified preparation of claim 1, wherein the oligonucleotide hybridizes to the sequence of nucleotide numbers from −313 to −282 in FIG. 1.

18. The purified preparation of claim 1 wherein the oligonucleotide hybridizes to the sequence of nucleotide numbers from −203 to −173 in FIG. 1.

19. The purified preparation of claim 1, wherein the oligonucleotide hybridizes to the sequence of nucleotide numbers from −252 to −221 in FIG. 1.

20. The purified preparation of claim 1, wherein the oligonucleotide hybridizes to a sequence located between nucleotide 16 and nucleotide 486 in FIG. 1.

21. The purified preparation of claim 1 wherein the oligonucleotide comprises a sequence selected from the group consisting of:

5' - TCC CTT GCT CGA TGT ACG GTA AGT GCT GAG AGC ACT CTT CCA TCT CAT CGA ACT CTC GGT AGA GGA CTT CCC TGT CAG GT - 3',
5' - CTG TCA GGT ATG ATT GCC GGC TTC CCG GAC - 3',
5' - TTT GGC TAG TGG TTA GTG GGC TGG TGA CAG - 3',
5' - AAG CCA CCG TGT GCG CTA GGG CTC AAG CCC- 3',
5' - CAG GAT GCT GTC TCC CGC ACT CAA CGT - 3',
5' - AGT GCA GTG GAT GAA CCG GCT GAT AGC CTT - 3',
5' - TCC TGA GGC GAC TGC ACC AGT GGA TAA GCT - 3',
5' - CAG GAT GCT GTC TCC CGC ACT CAA CGT C - 3',
5' - ATC AGG ACC GGG GTG AGA ACA ATT ACC ACT - 3',
5' - AGA GAC AAC CAT GAG GTC CCC GGT GTT C - 3',
5' - TCG GAC CTT TAC CTG GTC ACG AGG CAC - 3',
5' - ACC TTC CCC ATT AAT GCC TAC ACC ACG GGC - 3',
5' - TCC ATC TCT CAA GGC AAC TTG CAC CGC TAA - 3',
5' - TCC ATG GCT GTC CGC TTC CAC CTC CAA AGT - 3',
5' - GCG ACA ATA CGA CAA CAT CCT CTG AGC CCG - 3',
5' - AGC AGA CAA GGG GCC TCC TAG GGT GCA TAA T - 3',
5' - CAC CTA TGT TTA TAA CCA TCT CAC TCC TCT - 3',
5' - CTC TGT CAC CAT ATT ACA AGC GCT ATA TCA - 3',
5' - CTC GTT GCT ACG TCA CCA CAA TTT GGT GTA - 3',
5' - TGC TTG TGG ATG ATG CTA CTC ATA TCC CAA - 3',
5' - AGC AGC GGC GTC AAA AGT GAA GGC TAA CTT - 3',
5' - TTC TCG TAT GAT ACC CGC TGC TTT GAC TCC - 3',
5' - TGT GTG GCG ACG ACT TAG TCG TTA TCT GTG - 3',
5' - CAC ACT CCA GTC AAT TCC TGG CTA GGC AAC - 3',
5' - CTG GCT TGA AGA ATC - 3',
5' - AGT TAG GCT GGT GAT TAT GC - 3',
5' - GAA CGT TGC GAT CTG GAA GAC AGG GAC AGG - 3',
5' - TAT CAG TTA TGC CAA CGG AAG CGG CCC CGA - 3',
5' - CTG GTT AGC AGG GCT TTT CTA TCA CCA CAA - 3',
5' - AAG GTC CTG GTA GTG CTG CTG CTA TTT GCC - 3',
5' - ACT GGA CGA CGC AAG GTT GCA ATT GCT CTA - 3',
5' - TTC GAC GTC ACA TCG ATC TGC TTG TCG GGA - 3',
5' - GGT GAC GTG GGT TTC - 3',
5' - GGC TTT ACC ACG TCA CCA ATG ATT GCC CTA - 3',
5' - TTT GGG TAA GGT CAT CGA TAC CCT TAC GTG - 3',
5' - GAA GCC GCA CGT AAG - 3',
5' - CCG GCG TAG GTC GCG CAA TTT GGG TAA - 3',
5' - TCA GAT CGT TGG TGG AGT TTA CTT GTT GCC - 3',
5' - CCA TAG TGG TCT GCG GAA CCG GTG AGT ACA - 3',
5' - ATT GCG AGA TCT ACG GGG CCT GCT ACT CCA - 3',
5' - ATA GCG GCC GCC CTC GAT TGC GAG AGC TAC - 3',
5' - AAT TCG GGC GGC CGC CAT ACG A-3',
5' - CTT GAT CTA CCT CCA ATC ATT CAA AGA CTC - 3',
5' - TCT TCA ACT GGG CAG TAA GAA CAA AGC TCA - 3',
5' - AAT TCG CGG CCG CCA TAC GAT TTA GGT GAC ACT ATA GAA T$_{15}$-3',
5' - TTC GCG GCC GCT ACA GCG GGG GAG ACA T - 3',
5' - AAT TCG CGG CCG CCA TAC GA - 3',
5' - CGA TGA AGG TTG GGG TAA ACA CTC CGG CCT - 3',
5' - GAT CCT GGA ATT CTG ATA AGA CCT TAA GAC TAT TTT AA - 3',
5' - AAT TTG GGA ATT CCA TAA TGA GAC CCT TAA GGT ATT ACT CAG CT - 3',
5' - GAG TGC TCA AGC TTC AAA ACA AAA TGG CTC ACT TTC TAT CCC AGA CAA AGC AGA GT - 3',
5' - GAG TGC TCG ACT CAT TAG GGG GAA ACA TGG TTC CCC CGG GAG GCG AA-3',
5' - GAG TGC TCA AGC TTC AAA ACA AAA TGG GGC TCT ACC ACG TCA CCA ATG ATT GCC CTA AC - 3',
5' - GAG TGC TCG TCG ACT CAT TAA GGG GAC CAG TTC ATC ATC ATA TCC CAT GCC AT - 3',
5' - GAG TGC AGC TTC AAA ACA AAA TGA GCA CGA ATC CTA AAC CTC AAA AAA AAA AC- 3',
5' - GAG TGC TCG TCG ACT CAT TAA CCC AAA TTG CGC GAC CTA CGC CGG GGG TCT GT - 3'
5' - GAG TGC TCA AGC TTA CAA AAC AAA ATG GCA CCA GGC GCC AAG CAG AAG GTC CAG CTG ATC - 3',
5' - GAG TGC TCC TCG AGG TCG ACT CAT TAC TCG GAC CTG TCC CTA TCT TCC AGA TCG CAA CG - 3',
5' - GGA TCC GCT AGC GGC GCC AAG CAG AAC GTC CAG CTG ATC AAC ACC-3',
5' - GGA TCC AAG CTT TTA CTC GGA CCT GTC CCT ATC TTC CAG ATC GCA ACG - 3',

-continued

5' - CAA TCA TAC CTG ACA G - 3',
5' - GAT AAC CTC TGC CTG A - 3',
5' - GCA TGT CAT GAT GTA T - 3',
5' - ACA ATA CTG GTG TCA C - 3',
5' - CCA GCG GTG GCC TGG TAT TG - 3',
5' - TTT GGG TAA GGT CAT CGA TAC CCT TAC GTG - 3',
5' - ATA TGC GGC CGC CTT CCG TTG GAC TAA - 3',
5' - AAT TCG CGG CCG CCA TAC GAT TTA GGT GAC ACT ATA GAA CCC CCC CCC CCC CCC - 3',
5' - CGA CAA GAA AGA CAG A - 3',
5' - CGT TGG CAT AAC TGA T - 3',
5' - CTC TAT GGC AAT GAG G - 3',
5' - AGC TTC GAC GTC ACA T - 3',
5' - CTT GAA TTC GCA ATT TGG GTA AGG TCA TCG ATA CCC TTA CG-3',
5' - CTT GAA TTC GAT AGA GCA ATT GCA ACC TTG CGT CGT CC - 3',
5' - CTT GAA TTC GGA CGA CGC AAG GTT GCA ATT GCT CTA TC - 3',
5' - CTT GAA TTC CAG CCG GTG TTG AGG CTA TCA TTG CAG TTC - 3',
5' - TGA ACT ATG CAA CAG G - 3',
5' - GGA GTG TGC AGG ATG G - 3',
5' - AAG GTT GCA ATT GCT C - 3',
5' - ACT AAC AGG ACC TTC G - 3',
5' - TAA CGG GTC ACC GCA T - 3',
5' - GTA ATA TGG TGA CAG AGT CA - 3',
5' - GAT CTC TAG AGA AAT CAA TAT GGT GAC AGA GTC A - 3', and
5' - CCC AGC GGC GTA CGC GCT GGA CAC GGA GGT GGC CGC GTC GTG TGG CGG TGT TGT TCT CGT CGG GTT GAT GGC GC - 3'.

22. The purified preparation of claim 1 wherein the oligonucleotide comprises a contiguous sequence of at least 10 nucleotides fully complementary to a unique nucleotide residue sequence in either strand of the nucleotide residue sequence depicted in FIG. 1.

23. The purified preparation of claim 22 wherein the oligonucleotide is a primer for a DNA polymerase or a reverse transcriptase.

24. The purified preparation of claim 1 wherein the oligonucleotide comprises a contiguous sequence of at least 12 nucleotides fully complementary to a unique nucleotide residue sequence in either strand of the nucleotide residue sequence depicted in FIG. 1.

25. The purified preparation of claim 24 wherein the oligonucleotide is a primer for a DNA polymerase or a reverse transcriptase.

26. The purified preparation of claim 1 wherein the oligonucleotide comprises a contiguous sequence of at least 15 nucleotides fully complementary to a unique nucleotide residue sequence in either strand of the nucleotide residue sequence depicted in FIG. 1.

27. The purified preparation of claim 1 wherein the oligonucleotide comprises a contiguous sequence of at least 20 nucleotides fully complementary to a unique nucleotide residue sequence in either strand of the nucleotide residue sequence depicted in FIG. 1.

* * * * *